US008614069B2

(12) United States Patent
Cossins et al.

(10) Patent No.: US 8,614,069 B2
(45) Date of Patent: Dec. 24, 2013

(54) NON-CYTOTOXIC FUSION PROTEINS COMPRISING EGF MUTEINS

(75) Inventors: Aimee Cossins, Abingdon (GB); Ian Birch-Machin, Abingdon (GB); Patrick Stancombe, Abingdon (GB)

(73) Assignee: Syntaxin Limited, Abingdon, Oxfordshire (GB)

( * ) Notice: Subject to any disclaimer, the term of this patent is extended or adjusted under 35 U.S.C. 154(b) by 0 days.

(21) Appl. No.: 13/059,695

(22) PCT Filed: Aug. 19, 2009

(86) PCT No.: PCT/GB2009/051036
§ 371 (c)(1),
(2), (4) Date: Mar. 31, 2011

(87) PCT Pub. No.: WO2010/020811
PCT Pub. Date: Feb. 25, 2010

(65) Prior Publication Data
US 2011/0177056 A1 Jul. 21, 2011

(30) Foreign Application Priority Data
Aug. 21, 2008 (GB) .................................. 0815264.7

(51) Int. Cl.
*C12P 21/04* (2006.01)

(52) U.S. Cl.
USPC .......................................... 435/69.7; 435/212

(58) Field of Classification Search
None
See application file for complete search history.

(56) References Cited

U.S. PATENT DOCUMENTS

2008/0032928 A1* 2/2008 Quinn et al. .................... 514/12
2008/0038274 A1 2/2008 Foster et al.

FOREIGN PATENT DOCUMENTS

| | | | |
|---|---|---|---|
| EP | 1479693 A1 | | 11/2004 |
| WO | WO00/10598 | * | 3/2000 |
| WO | 03/040310 A2 | | 5/2003 |
| WO | 2007/109673 A2 | | 9/2007 |
| WO | 2009/083738 A2 | | 7/2009 |

OTHER PUBLICATIONS

Rogers et al, Ann Med. 2006;38(2)116-25. Treatment of airway mucus hypersecretion.*

Wishart et al, A single mutation converts a novel phosphotyrosine binding domain into a dual-specificity phosphatase. J Biol Chem. Nov. 10, 1995;270(45):26782-26785.*

Whisstock et al, Prediction of protein function from protein sequence and structure. Q Rev Biophys. Aug. 2003;36(3):307-40. Review.*

Issued_Patents_AA:* US5547935 Mullenbach et al, Aug. 8, 1996, Seq ID No. 1. Alignment with Seq ID No. 11.*

A_Geneseq_201215:* Acc#AJL79951 from WO2007109673 Sep. 27,2007, priority Mar. 20,2006; 2006US-0784274P. Alignment with Seq ID No. 11.*

International Search Report for PCT/2009/051036 dated Dec. 28, 2009.

UK Search Report GB0815264.7 dated Dec. 23, 2008.

Her-Shyong Shiah et al., "Pseudomonas Exotoxin A-Epidermal Growth Factor (EGF) Mutant Chimeric Protein as an Indicator for Identifying Amino Acid Residues Important in EGF-Receptor Interaction" The Journal of Biological Chemistry, vol. 267, No. 33, pp. 24034-24040, Nov. 25, 1992.

Guy T. Mullenbach et al., "Modification of a receptor-binding surface of epidermal growth factor (EGF): analogs with enhanced receptor affinity at low pH or at neutrality" Protein Engineering, vol. 11, No. 6, pp. 473-180, 1998.

Keith Foster "Harnessing Toxins" Manufacturing Chemist, pp. 23-24, 26, Oct. 2006.

Keith Foster "Engineered Toxins: New Therapeutics" Abstracts Toxins pp. 47-48 [2008].

Keisuke Makino et al. "Proton nuclear magnetic resonance study on the solution conformation of human epidermal growth factor" Proceedings of the National Academy of Sciences of the USA, vol. 84, pp. 7841-7845, Nov. 1987.

Robert N. Jorissen et al. "Modeling the Epidermal Growth Factor—Epidermal Growth Factor Receptor L2 Domain Interaction: Implications for the Ligand Binding Process" Journal of Biomolecular Structure & Dynamics, vol. 19, Issue No. 6, pp. 961-972 [2002].

Keith A Foster et al, "Re-Engineering the Target Specificity of Clostridial Neurotoxins—a Route to Novel Therapeutics" Neurotoxicity Research, vol. 9(2,3). pp. 101-107 [2006].

* cited by examiner

*Primary Examiner* — Sheridan Swope

(74) *Attorney, Agent, or Firm* — Morris, Manning & Martin, LLP; Christopher W. Raimund

(57) ABSTRACT

The present invention relates to fusion proteins comprising a non-cytotoxic protease and a EGF mutein ligand. The EGF mutein provides improved EGF receptor activation for the claimed fusion proteins. Also provided is the use of said polypeptides as therapeutics for suppressing mucus hypersecretion, inflammation, endocrine neoplasia and/or neuroendocrine disorders, neuroendocrine tumors, for suppressing cancers such as colorectal cancer, prostate cancer, breast cancer, and lung cancer.

5 Claims, 5 Drawing Sheets

SEQUENCE LISTING

<160> NUMBER OF SEQ ID NOS: 73

<210> SEQ ID NO 1
<211> LENGTH: 53
<212> TYPE: PRT
<213> ORGANISM: Homo sapiens

<400> SEQUENCE: 1

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 2

-continued

<211> LENGTH: 2595
<212> TYPE: DNA
<213> ORGANISM: Artificial Sequence
<220> FEATURE:
<223> OTHER INFORMATION: DNA sequence of LHA

<400> SEQUENCE: 2

```
atggagttcg ttaacaaaca gttcaactat aaagacccag ttaacggtgt tgacattgct     60

tacatcaaaa tcccgaacgc tggccagatg cagccggtaa aggcattcaa aatccacaac    120

aaaatctggg ttatcccgga acgtgatacc tttactaacc cggaagaagg tgacctgaac    180

ccgccaccgg aagcgaaaca ggtgccggta tcttactatg actccaccta cctgtctacc    240

gataacgaaa aggacaacta cctgaaaggt gttactaaac tgttcgagcg tatttactcc    300

accgacctgg gccgtatgct gctgactagc atcgttcgcg gtatcccgtt ctggggcggt    360

tctaccatcg ataccgaact gaaagtaatc gacactaact gcatcaacgt tattcagccg    420

gacggttcct atcgttccga agaactgaac ctggtgatca tcggcccgtc tgctgatatc    480

atccagttcg agtgtctgag ctttggtcac gaagttctga acctcacccg taacggctac    540

ggttccactc agtacatccg tttctctccg gacttcacct tcggttttga agaatccctg    600

gaagtagaca cgaacccact gctgggcgct ggtaaattcg caactgatcc tgcggttacc    660

ctggctcacg aactgattca tgcaggccac cgcctgtacg gtatcgccat caatccgaac    720

cgtgtcttca aagttaacac caacgcgtat tacgagatgt ccggtctgga agttagcttc    780

gaagaactgc gtacttttgg cggtcacgac gctaaattca tcgactctct gcaagaaaac    840

gagttccgtc tgtactacta taacaagttc aaagatatcg catccaccct gaacaaagcg    900

aaatccatcg tgggtaccac tgcttctctc cagtacatga agaacgtttt taaagaaaaa    960

tacctgctca gcgaagacac ctccggcaaa ttctctgtag acaagttgaa attcgataaa   1020

ctttacaaaa tgctgactga aatttacacc gaagacaact tcgttaagtt ctttaaagtt   1080

ctgaaccgca aaacctatct gaacttcgac aaggcagtat tcaaaatcaa catcgtgccg   1140

aaagttaact acactatcta cgatggtttc aacctgcgta acaccaacct ggctgctaat   1200

tttaacggcc agaacacgga aatcaacaac atgaacttca caaaactgaa aaacttcact   1260

ggtctgttcg agttttacaa gctgctgtgc gtcgacggca tcattacctc caaaactaaa   1320

tctgacgatg acgataaaaa caaagcgctg aacctgcagt gtatcaaggt taacaactgg   1380

gatttattct tcagcccgag tgaagacaac ttcaccaacg acctgaacaa aggtgaagaa   1440

atcacctcag atactaacat cgaagcagcc gaagaaaaca tctcgctgga cctgatccag   1500

cagtactacc tgacctttaa tttcgacaac gagccggaaa acatttctat cgaaaacctg   1560

agctctgata tcatcggcca gctggaactg atgccgaaca tcgaacgttt cccaaacggt   1620

aaaaagtacg agctggacaa atataccatg ttccactacc tgcgcgcgca ggaatttgaa   1680

cacggcaaat cccgtatcgc actgactaac tccgttaacg aagctctgct caacccgtcc   1740

cgtgtataca ccttcttctc tagcgactac gtgaaaaagg tcaacaaagc gactgaagct   1800

gcaatgttct tgggttgggt tgaacagctt gtttatgatt ttaccgacga gacgtccgaa   1860

gtatctacta ccgacaaaat tgcggatatc actatcatca tcccgtacat cggtccggct   1920

ctgaacattg gcaacatgct gtacaaagac gacttcgttg gcgcactgat cttctccggt   1980

gcggtgatcc tgctggagtt catcccggaa atcgccatcc cggtactggg cacctttgct   2040

ctggtttctt acattgcaaa caaggttctg actgtacaaa ccatcgacaa cgcgctgagc   2100

aaacgtaacg aaaaatggga tgaagtttac aaatatatcg tgaccaactg gctggctaag   2160
```

-continued

```
gttaatactc agatcgacct catccgcaaa aaaatgaaag aagcactgga aaaccaggcg   2220

gaagctacca aggcaatcat taactaccag tacaaccagt acaccgagga agaaaaaaac   2280

aacatcaact tcaacatcga cgatctgtcc tctaaactga acgaatccat caacaaagct   2340

atgatcaaca tcaacaagtt cctgaaccag tgctctgtaa gctatctgat gaactccatg   2400

atcccgtacg gtgttaaacg tctggaggac ttcgatgcgt ctctgaaaga cgccctgctg   2460

aaatacattt acgacaaccg tggcactctg atcggtcagg ttgatcgtct gaaggacaaa   2520

gtgaacaata ccttatcgac cgacatccct tttcagctca gtaaatatgt cgataaccaa   2580

cgccttttgt ccact                                                    2595
```

<210> SEQ ID NO 3
<211> LENGTH: 2619
<212> TYPE: DNA
<213> ORGANISM: Artificial Sequence
<220> FEATURE:
<223> OTHER INFORMATION: DNA sequence of LHB

<400> SEQUENCE: 3

```
atgccggtta ccatcaacaa cttcaactac aacgacccga tcgacaacaa caacatcatt     60

atgatggaac cgccgttcgc acgtggtacc ggacgttact acaaggcttt taagatcacc    120

gaccgtatct ggatcatccc ggaacgttac accttcggtt acaaacctga ggacttcaac    180

aagagtagcg ggattttcaa tcgtgacgtc tgcgagtact atgatccaga ttatctgaat    240

accaacgata agaagaacat attccttcag actatgatta aactcttcaa ccgtatcaaa    300

agcaaaccgc tcggtgaaaa actcctcgaa atgattatca acggtatccc gtacctcggt    360

gaccgtcgtg tcccgcttga agagttcaac accaacatcg caagcgtcac cgtcaacaaa    420

ctcatcagca acccaggtga agtcgaacgt aaaaaaggta tcttcgcaaa cctcatcatc    480

ttcggtccgg gtccggtcct caacgaaaac gaaaccatcg acatcggtat ccagaaccac    540

ttcgcaagcc gtgaaggttt cggtggtatc atgcagatga aattctgccc ggaatacgtc    600

agtgtcttca acaacgtcca ggaaaacaaa ggtgcaagca tcttcaaccg tcgtggttac    660

ttcagcgacc cggcactcat cctcatgcat gaactcatcc acgtcctcca cggtctctac    720

ggtatcaaag ttgacgacct cccgatcgtc ccgaacgaga agaaattctt catgcagagc    780

accgacgcaa tccaggctga ggaactctac accttcggtg gccaagaccc aagtatcata    840

accccgtcca ccgacaaaag catctacgac aaagtcctcc agaacttcag ggtatcgtg    900

gacagactca acaaagtcct cgtctgcatc agcgacccga acatcaatat caacatatac    960

aagaacaagt tcaaagacaa gtacaaattc gtcgaggaca gcgaaggcaa atacagcatc   1020

gacgtagaaa gtttcgacaa gctctacaaa agcctcatgt tcggtttcac cgaaaccaac   1080

atcgccgaga actacaagat caagacaagg gcaagttact tcagcgacag cctcccgcct   1140

gtcaaaatca agaacctctt agacaacgag atttacacaa ttgaagaggg cttcaacatc   1200

agtgacaaag acatggagaa ggaatacaga ggtcagaaca aggctatcaa caaacaggca   1260

tacgaggaga tcagcaaaga acacctcgca gtctacaaga tccagatgtg cgtcgacggc   1320

atcattacct ccaaaactaa atctgacgat gacgataaaa acaaagcgct gaacctgcag   1380

tgcatcgacg ttgacaacga agacctgttc ttcatcgctg acaaaaacag cttcagtgac   1440

gacctgagca aaaacgaacg tatcgaatac aacacccaga gcaactacat cgaaaacgac   1500

ttcccgatca acgaactgat cctggacacc gacctgataa gtaaaatcga actgccgagc   1560

gaaaacaccg aaagtctgac cgacttcaac gttgacgttc cggtttacga aaaacagccg   1620
```

-continued gctatcaaga aaatcttcac cgacgaaaac accatcttcc agtacctgta cagccagacc 1680
ttcccgctgg acatccgtga catcagtctg accagcagtt tcgacgacgc tctgctgttc 1740
agcaacaaag tttacagttt cttcagcatg gactacatca aaaccgctaa caaagttgtt 1800
gaagcagggc tgttcgctgg ttgggttaaa cagatcgtta acgacttcgt tatcgaagct 1860
aacaaaagca acactatgga caaaatcgct gacatcagtc tgatcgttcc gtacatcggt 1920
ctggctctga acgttggtaa cgaaaccgct aaaggtaact ttgaaaacgc tttcgagatc 1980
gctggtgcaa gcatcctgct ggagttcatc ccggaactgc tgatcccggt tgttggtgct 2040
ttcctgctgg aaagttacat cgacaacaaa aacaagatca tcaaaaccat cgacaacgct 2100
ctgaccaaac gtaacgaaaa atggagtgat atgtacggtc tgatcgttgc tcagtggctg 2160
agcaccgtca acacccagtt ctacaccatc aaagaaggta tgtacaaagc tctgaactac 2220
caggctcagg ctctggaaga gatcatcaaa taccgttaca acatctacag tgagaaggaa 2280
aagagtaaca tcaacatcga cttcaacgac atcaacagca aactgaacga aggtatcaac 2340
caggctatcg acaacatcaa caacttcatc aacggttgca gtgttagcta cctgatgaag 2400
aagatgatcc cgctggctgt tgaaaaactg ctggacttcg acaacaccct gaaaaagaac 2460
ctgctgaact acatcgacga aaacaagctg tacctgatcg gtagtgctga atacgaaaaa 2520
agtaaagtga acaaatacct gaagaccatc atgccgttcg acctgagtat ctacaccaac 2580
gacaccatcc tgatcgaaat gttcaacaaa tacaactct 2619

<210> SEQ ID NO 4
<211> LENGTH: 2616
<212> TYPE: DNA
<213> ORGANISM: Artificial Sequence
<220> FEATURE:
<223> OTHER INFORMATION: DNA sequence of LHC

<400> SEQUENCE: 4
atgacgtggc cagttaagga tttcaactac tcagatcctg taaatgacaa cgatattctg 60
taccttcgca ttccacaaaa taaactgatc accacaccag tcaaagcatt catgattact 120
caaaacattt gggtcattcc agaacgcttt tctagtgaca caaatccgag tttatctaaa 180
cctccgcgtc cgacgtccaa atatcagagc tattacgatc cctcatatct cagtacggac 240
gaacaaaaag atactttcct taaaggtatc attaaactgt ttaagcgtat taatgagcgc 300
gatatcggga aaaagttgat taattatctt gttgtgggtt ccccgttcat gggcgatagc 360
tctacccccg aagacacttt tgattttacc cgtcatacga caaacatcgc ggtagagaag 420
tttgagaacg gatcgtggaa agtcacaaac atcattacac ctagcgtctt aatttttggt 480
ccgctgccaa acatcttaga ttatacagcc agcctgactt tgcaggggca acagtcgaat 540
ccgagtttcg aaggttttgg taccctgagc attctgaaag ttgccccgga atttctgctc 600
actttttcag atgtcaccag caaccagagc tcagcagtat taggaaagtc aatttttttgc 660 atggacccgg ttattgcact gatgcacgaa ctgacgcact ctctgcatca actgtatggg 720
atcaacatcc ccagtgacaa acgtattcgt ccccaggtgt ctgaaggatt tttctcacag 780
gatgggccga acgtccagtt cgaagagttg tatactttcg gaggcctgga cgtagagatc 840
attccccaga ttgagcgcag tcagctgcgt gagaaggcat tgggccatta taaggatatt 900
gcaaaacgcc tgaataacat taacaaaacg attccatctt cgtggatctc gaatattgat 960
aaatataaga aaatttttag cgagaaatat aattttgata aagataatac aggtaacttt 1020
gtggttaaca ttgacaaatt caactccctt tacagtgatt tgacgaatgt aatgagcgaa 1080
gttgtgtata gttcccaata caacgttaag aatcgtaccc attacttctc tcgtcactac 1140
ctgccggttt tcgcgaacat ccttgacgat aatatttaca ctattcgtga cggctttaac 1200
ttgaccaaca agggcttcaa tattgaaaat tcaggccaga acattgaacg caacccggcc 1260
ttgcagaaac tgtcgagtga atccgtggtt gacctgttta ccaaagtctg cgtcgacaaa 1320
agcgaagaga agctgtacga tgacgatgac aaagatcgtt ggggatcgtc cctgcagtgt 1380
attaaagtga aaaacaatcg gctgccttat gtagcagata aagatagcat tagtcaggag 1440
attttcgaaa ataaaattat cactgacgaa accaatgttc agaattattc agataaattt 1500
tcactggacg aaagcatctt agatggccaa gttccgatta acccggaaat tgttgatccg 1560
ttactgccga acgtgaatat ggaaccgtta aacctccctg gcgaagagat cgtattttat 1620
gatgacatta cgaaatatgt ggactacctt aattcttatt actatttgga aagccagaaa 1680
ctgtccaata acgtggaaaa cattactctg accacaagcg tggaagaggc tttaggctac 1740
tcaaataaga tttatacctt cctcccgtcg ctggcggaaa aagtaaataa aggtgtgcag 1800
gctggtctgt tcctcaactg ggcgaatgaa gttgtcgaag actttaccac gaatattatg 1860
aaaaaggata ccctggataa aatctccgac gtctcggtta ttatcccata tattggccct 1920
gcgttaaata tcggtaatag tgcgctgcgg gggaatttta accaggcctt tgctaccgcg 1980
ggcgtcgcgt tcctcctgga gggctttcct gaatttacta tcccggcgct cggtgttttt 2040
acattttact cttccatcca ggagcgtgag aaaattatca aaaccatcga aaactgcctg 2100
gagcagcggg tgaaacgctg gaaagattct tatcaatgga tggtgtcaaa ctggttatct 2160
cgcatcacga cccaattcaa ccatattaat taccagatgt atgatagtct gtcgtaccaa 2220
gctgacgcca ttaaagccaa aattgatctg gaatataaaa agtactctgg tagcgataag 2280
gagaacatca aaagccaggt ggagaacctt aagaatagtc tggatgtgaa aatctctgaa 2340
gctatgaata acattaacaa attcattcgt gaatgttcgg tgacgtacct gttcaagaat 2400
atgctgccaa aagttattga tgaactgaat aaatttgatc tgcgtaccaa aaccgaactt 2460
atcaacctca tcgactccca caacattatc cttgtgggcg aagtggatcg tctgaaggcc 2520
aaagtaaacg agagctttga aaatacgatg ccgtttaata ttttttcata taccaataac 2580
tccttgctga aagatatcat caatgaatat ttcaat 2616

<210> SEQ ID NO 5
<211> LENGTH: 2616
<212> TYPE: DNA
<213> ORGANISM: Artificial Sequence
<220> FEATURE:
<223> OTHER INFORMATION: DNA sequence of LHD

<400> SEQUENCE: 5
atgacgtggc cagttaagga tttcaactac tcagatcctg taaatgacaa cgatattctg 60
taccttcgca ttccacaaaa taaactgatc accacaccag tcaaagcatt catgattact 120
caaaacattt gggtcattcc agaacgcttt tctagtgaca caaatccgag tttatctaaa 180
cctccgcgtc cgacgtccaa atatcagagc tattacgatc cctcatatct cagtacggac 240
gaacaaaaag atactttcct taaaggtatc attaaactgt ttaagcgtat taatgagcgc 300
gatatcggga aaaagttgat taattatctt gttgtgggtt ccccgttcat gggcgatagc 360
tctacccccg aagacacttt tgattttacc cgtcatacga caaacatcgc ggtagagaag 420
tttgagaacg gatcgtggaa agtcacaaac atcattacac ctagcgtctt aatttttggt 480
ccgctgccaa acatcttaga ttatacagcc agcctgactt tgcaggggca acagtcgaat 540

-continued

```
ccgagtttcg aaggttttgg taccctgagc attctgaaag ttgccccgga atttctgctc    600

actttttcag atgtcaccag caaccagagc tcagcagtat taggaaagtc aatttttttgc    660

atggacccgg ttattgcact gatgcacgaa ctgacgcact ctctgcatca actgtatggg    720

atcaacatcc ccagtgacaa acgtattcgt ccccaggtgt ctgaaggatt tttctcacag    780

gatgggccga acgtccagtt cgaagagttg tatactttcg gaggcctgga cgtagagatc    840

attccccaga ttgagcgcag tcagctgcgt gagaaggcat tgggccatta taaggatatt    900

gcaaaacgcc tgaataacat taacaaaacg attccatctt cgtggatctc gaatattgat    960

aaatataaga aaatttttag cgagaaatat aattttgata aagataatac aggtaacttt   1020

gtggttaaca ttgacaaatt caactccctt tacagtgatt tgacgaatgt aatgagcgaa   1080

gttgtgtata gttcccaata caacgttaag aatcgtaccc attacttctc tcgtcactac   1140

ctgccggttt tcgcgaacat ccttgacgat aatatttaca ctattcgtga cggctttaac   1200

ttgaccaaca agggcttcaa tattgaaaat tcaggccaga acattgaacg caacccggcc   1260

ttgcagaaac tgtcgagtga atccgtggtt gacctgttta ccaaagtctg cgtcgacaaa   1320

agcgaagaga agctgtacga tgacgatgac aaagatcgtt ggggatcgtc cctgcagtgt   1380

attaaagtga aaaacaatcg gctgccttat gtagcagata aagatagcat tagtcaggag   1440

attttcgaaa ataaaattat cactgacgaa accaatgttc agaattattc agataaattt   1500

tcactggacg aaagcatctt agatggccaa gttccgatta acccggaaat tgttgatccg   1560

ttactgccga acgtgaatat ggaaccgtta aacctccctg gcgaagagat cgtatttttat   1620

gatgacatta cgaaatatgt ggactacctt aattcttatt actatttgga aagccagaaa   1680

ctgtccaata acgtggaaaa cattactctg accacaagcg tggaagaggc tttaggctac   1740

tcaaataaga tttatacctt cctcccgtcg ctggcggaaa aagtaaataa aggtgtgcag   1800

gctggtctgt tcctcaactg ggcgaatgaa gttgtcgaag actttaccac gaatattatg   1860

aaaaaggata ccctggataa aatctccgac gtctcggtta ttatcccata tattggccct   1920

gcgttaaata tcggtaatag tgcgctgcgg gggaatttta accaggcctt tgctaccgcg   1980

ggcgtcgcgt tcctcctgga gggctttcct gaatttacta tcccggcgct cggtgttttt   2040

acattttact cttccatcca ggagcgtgag aaaattatca aaaccatcga aaactgcctg   2100

gagcagcggg tgaaacgctg gaaagattct tatcaatgga tggtgtcaaa ctggttatct   2160

cgcatcacga cccaattcaa ccatattaat taccagatgt atgatagtct gtcgtaccaa   2220

gctgacgcca ttaaagccaa aattgatctg gaatataaaa agtactctgg tagcgataag   2280

gagaacatca aaagccaggt ggagaacctt aagaatagtc tggatgtgaa aatctctgaa   2340

gctatgaata acattaacaa attcattcgt gaatgttcgg tgacgtacct gttcaagaat   2400

atgctgccaa aagttattga tgaactgaat aaatttgatc tgcgtaccaa aaccgaactt   2460

atcaacctca tcgactccca caacattatc cttgtgggcg aagtggatcg tctgaaggcc   2520

aaagtaaacg agagctttga aaatacgatg ccgtttaata ttttttcata taccaataac   2580

tccttgctga aagatatcat caatgaatat ttcaat                             2616
```

<210> SEQ ID NO 6
<211> LENGTH: 53
<212> TYPE: PRT
<213> ORGANISM: Artificial Sequence
<220> FEATURE:
<223> OTHER INFORMATION: EGFH16N

<400> SEQUENCE: 6

-continued

```
Asn Ser Asp Ser Glu Cys Pro Leu Ser His Asp Gly Tyr Cys Leu Asn
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50


<210> SEQ ID NO 7
<211> LENGTH: 53
<212> TYPE: PRT
<213> ORGANISM: Artificial Sequence
<220> FEATURE:
<223> OTHER INFORMATION: Protein sequence of a EGF variant targeting
      moiety v1

<400> SEQUENCE: 7

Asn Ser Asp Ser Glu Cys Pro Leu Ser His Asp Gly Tyr Cys Leu His
1               5                   10                  15

Gly Gly Val Cys Met Tyr Ile Lys Ala Val Asp Arg Tyr Ala Cys Asn
            20                  25                  30

Cys Val Val Gly Tyr Ile Gly Glu Arg Cys Gln Tyr Arg Asp Leu Thr
        35                  40                  45

Trp Trp Gly Pro Arg
    50


<210> SEQ ID NO 8
<211> LENGTH: 53
<212> TYPE: PRT
<213> ORGANISM: Artificial Sequence
<220> FEATURE:
<223> OTHER INFORMATION: EGFH16Q

<400> SEQUENCE: 8

Asn Ser Asp Ser Glu Cys Pro Leu Ser His Asp Gly Tyr Cys Leu Gln
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50


<210> SEQ ID NO 9
<211> LENGTH: 53
<212> TYPE: PRT
<213> ORGANISM: Artificial Sequence
<220> FEATURE:
<223> OTHER INFORMATION: Protein sequence of a EGF variant targeting
      moiety v2

<400> SEQUENCE: 9

Ser Arg Gly Ser Lys Cys Pro Pro Ser His Asp Gly Tyr Cys Leu Gln
1               5                   10                  15

Gly Gly Val Cys Met Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Thr
        35                  40                  45

Trp Trp Gly Arg Arg
    50
```

<210> SEQ ID NO 10
<211> LENGTH: 53
<212> TYPE: PRT
<213> ORGANISM: Artificial Sequence
<220> FEATURE:
<223> OTHER INFORMATION: EGFW49L

<400> SEQUENCE: 10

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Leu Trp Glu Leu Arg
    50
```

<210> SEQ ID NO 11
<211> LENGTH: 53
<212> TYPE: PRT
<213> ORGANISM: Artificial Sequence
<220> FEATURE:
<223> OTHER INFORMATION: Protein sequence of a EGF variant targeting moiety v3

<400> SEQUENCE: 11

```
Asn Ser Asp Pro Lys Cys Pro Leu Ser His Glu Gly Tyr Cys Leu Asn
1               5                   10                  15

Asp Gly Val Cys Met Tyr Ile Gly Thr Leu Asp Arg Tyr Ala Cys Asn
            20                  25                  30

Cys Val Val Gly Tyr Val Gly Glu Arg Cys Gln Tyr Arg Asp Leu Lys
        35                  40                  45

Leu Ala Glu Leu Arg
    50
```

<210> SEQ ID NO 12
<211> LENGTH: 53
<212> TYPE: PRT
<213> ORGANISM: Artificial Sequence
<220> FEATURE:
<223> OTHER INFORMATION: EGFW49I

<400> SEQUENCE: 12

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Ile Trp Glu Leu Arg
    50
```

<210> SEQ ID NO 13
<211> LENGTH: 53
<212> TYPE: PRT
<213> ORGANISM: Artificial Sequence
<220> FEATURE:
<223> OTHER INFORMATION: Protein sequence of a EGF variant targeting moiety v4

<400> SEQUENCE: 13

```
Asn Ser Tyr Ser Glu Cys Pro Pro Ser Tyr Asp Gly Tyr Cys Leu His
1               5                   10                  15
```

```
Asp Gly Val Cys Arg Tyr Ile Glu Ala Leu Asp Ser Tyr Ala Cys Asn
            20                  25                  30

Cys Val Val Gly Tyr Ala Gly Glu Arg Cys Gln Tyr Arg Asp Leu Arg
        35                  40                  45

Trp Trp Gly Arg Arg
    50


<210> SEQ ID NO 14
<211> LENGTH: 53
<212> TYPE: PRT
<213> ORGANISM: Artificial Sequence
<220> FEATURE:
<223> OTHER INFORMATION: EGFW49V

<400> SEQUENCE: 14

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Val Trp Glu Leu Arg
    50


<210> SEQ ID NO 15
<211> LENGTH: 53
<212> TYPE: PRT
<213> ORGANISM: Artificial Sequence
<220> FEATURE:
<223> OTHER INFORMATION: Protein sequence of a EGF variant targeting
      moiety v5

<400> SEQUENCE: 15

Asn Ser Asp Ser Gly Cys Pro Ser Phe His Asp Gly Tyr Cys Leu Asn
1               5                   10                  15

Gly Gly Val Cys Met Tyr Ile Glu Ala Leu Asp Lys Tyr Ala Cys Asn
            20                  25                  30

Cys Val Ile Gly Tyr Asn Gly Asp Arg Cys Gln Thr Arg Asp Leu Lys
        35                  40                  45

Trp Trp Glu Leu Arg
    50


<210> SEQ ID NO 16
<211> LENGTH: 53
<212> TYPE: PRT
<213> ORGANISM: Artificial Sequence
<220> FEATURE:
<223> OTHER INFORMATION: EGFW49A

<400> SEQUENCE: 16

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Ala Trp Glu Leu Arg
    50


<210> SEQ ID NO 17
<211> LENGTH: 53
```

<212> TYPE: PRT
<213> ORGANISM: Artificial Sequence
<220> FEATURE:
<223> OTHER INFORMATION: Protein sequence of a EGF variant targeting
moiety v6 (G12Q)

<400> SEQUENCE: 17

```
Asn Ser Asp Ser Glu Cys Pro Leu Ser His Asp Gln Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 18
<211> LENGTH: 53
<212> TYPE: PRT
<213> ORGANISM: Artificial Sequence
<220> FEATURE:
<223> OTHER INFORMATION: EGFW49G

<400> SEQUENCE: 18

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Gly Trp Glu Leu Arg
    50
```

<210> SEQ ID NO 19
<211> LENGTH: 53
<212> TYPE: PRT
<213> ORGANISM: Artificial Sequence
<220> FEATURE:
<223> OTHER INFORMATION: Protein sequence of a EGF variant targeting
moiety v7 (H16D)

<400> SEQUENCE: 19

```
Asn Ser Asp Ser Glu Cys Pro Leu Ser His Asp Gly Tyr Cys Leu Asp
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 20
<211> LENGTH: 53
<212> TYPE: PRT
<213> ORGANISM: Artificial Sequence
<220> FEATURE:
<223> OTHER INFORMATION: EGFW49S

<400> SEQUENCE: 20

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30
```

```
Cys Val Val Gly Tyr Ile Gly Glu Arg Cys Gln Tyr Arg Asp Leu Lys
        35                  40                  45

Ser Trp Glu Leu Arg
    50


<210> SEQ ID NO 21
<211> LENGTH: 53
<212> TYPE: PRT
<213> ORGANISM: Artificial Sequence
<220> FEATURE:
<223> OTHER INFORMATION: Protein sequence of a EGF variant targeting
      moiety v8 (Y13W)

<400> SEQUENCE: 21

Asn Ser Asp Ser Glu Cys Pro Leu Ser His Asp Gly Trp Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50


<210> SEQ ID NO 22
<211> LENGTH: 53
<212> TYPE: PRT
<213> ORGANISM: Artificial Sequence
<220> FEATURE:
<223> OTHER INFORMATION: EGFW49T

<400> SEQUENCE: 22

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Thr Trp Glu Leu Arg
    50


<210> SEQ ID NO 23
<211> LENGTH: 53
<212> TYPE: PRT
<213> ORGANISM: Artificial Sequence
<220> FEATURE:
<223> OTHER INFORMATION: Protein sequence of a EGF variant targeting
      moiety v9 (Q43A)

<400> SEQUENCE: 23

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Ala Tyr Arg Asp Leu Lys
        35                  40                  45

Trp Trp Glu Leu Arg
    50


<210> SEQ ID NO 24
<211> LENGTH: 53
<212> TYPE: PRT
<213> ORGANISM: Artificial Sequence
```

<220> FEATURE:
<223> OTHER INFORMATION: EGFW49N

<400> SEQUENCE: 24

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Asn Trp Glu Leu Arg
    50
```

<210> SEQ ID NO 25
<211> LENGTH: 53
<212> TYPE: PRT
<213> ORGANISM: Artificial Sequence
<220> FEATURE:
<223> OTHER INFORMATION: Protein sequence of a EGF variant targeting moiety v10 (H16A)

<400> SEQUENCE: 25

```
Asn Ser Asp Ser Glu Cys Pro Leu Ser His Asp Gly Tyr Cys Leu Ala
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 26
<211> LENGTH: 53
<212> TYPE: PRT
<213> ORGANISM: Artificial Sequence
<220> FEATURE:
<223> OTHER INFORMATION: EGF_W49Q

<400> SEQUENCE: 26

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Gln Trp Glu Leu Arg
    50
```

<210> SEQ ID NO 27
<211> LENGTH: 53
<212> TYPE: PRT
<213> ORGANISM: Artificial Sequence
<220> FEATURE:
<223> OTHER INFORMATION: Protein sequence of a EGF variant targeting moiety v11 (L15A)

<400> SEQUENCE: 27

```
Asn Ser Asp Ser Glu Cys Pro Leu Ser His Asp Gly Tyr Cys Ala His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
```

35 40 45

Trp Trp Glu Leu Arg
50

<210> SEQ ID NO 28
<211> LENGTH: 53
<212> TYPE: PRT
<213> ORGANISM: Artificial Sequence
<220> FEATURE:
<223> OTHER INFORMATION: EGF_H16N_W49L

<400> SEQUENCE: 28

Asn Ser Asp Ser Glu Cys Pro Leu Ser His Asp Gly Tyr Cys Leu Asn
1 5 10 15

Asp Gly Val Cys Met Tyr Ile Glu Ala Leu Asp Lys Tyr Ala Cys Asn
20 25 30

Cys Val Val Gly Tyr Ile Gly Glu Arg Cys Gln Tyr Arg Asp Leu Lys
35 40 45

Leu Trp Glu Leu Arg
50

<210> SEQ ID NO 29
<211> LENGTH: 53
<212> TYPE: PRT
<213> ORGANISM: Artificial Sequence
<220> FEATURE:
<223> OTHER INFORMATION: Protein sequence of a EGF variant targeting moiety v12 (V19E)

<400> SEQUENCE: 29

Asn Ser Asp Ser Glu Cys Pro Leu Ser His Asp Gly Tyr Cys Leu His
1 5 10 15

Asp Gly Glu Cys Met Tyr Ile Glu Ala Leu Asp Lys Tyr Ala Cys Asn
20 25 30

Cys Val Val Gly Tyr Ile Gly Glu Arg Cys Gln Tyr Arg Asp Leu Lys
35 40 45

Trp Trp Glu Leu Arg
50

<210> SEQ ID NO 30
<211> LENGTH: 53
<212> TYPE: PRT
<213> ORGANISM: Artificial Sequence
<220> FEATURE:
<223> OTHER INFORMATION: EGF_H16Q_W49L

<400> SEQUENCE: 30

Asn Ser Asp Ser Glu Cys Pro Leu Ser His Asp Gly Tyr Cys Leu Gln
1 5 10 15

Asp Gly Val Cys Met Tyr Ile Glu Ala Leu Asp Lys Tyr Ala Cys Asn
20 25 30

Cys Val Val Gly Tyr Ile Gly Glu Arg Cys Gln Tyr Arg Asp Leu Lys
35 40 45

Leu Trp Glu Leu Arg
50

<210> SEQ ID NO 31
<211> LENGTH: 53
<212> TYPE: PRT
<213> ORGANISM: Artificial Sequence
<220> FEATURE:
<223> OTHER INFORMATION: Protein sequence of a EGF variant targeting moiety v13 (V34D)

<400> SEQUENCE: 31

Asn Ser Asp Ser Glu Cys Pro Leu Ser His Asp Gly Tyr Cys Leu His
1 5 10 15

Asp Gly Val Cys Met Tyr Ile Glu Ala Leu Asp Lys Tyr Ala Cys Asn
20 25 30

Cys Asp Val Gly Tyr Ile Gly Glu Arg Cys Gln Tyr Arg Asp Leu Lys
35 40 45

Trp Trp Glu Leu Arg
50

<210> SEQ ID NO 32
<211> LENGTH: 53
<212> TYPE: PRT
<213> ORGANISM: Artificial Sequence
<220> FEATURE:
<223> OTHER INFORMATION: EGF_H16N_W49I

<400> SEQUENCE: 32

Asn Ser Asp Ser Glu Cys Pro Leu Ser His Asp Gly Tyr Cys Leu Asn
1 5 10 15

Asp Gly Val Cys Met Tyr Ile Glu Ala Leu Asp Lys Tyr Ala Cys Asn
20 25 30

Cys Val Val Gly Tyr Ile Gly Glu Arg Cys Gln Tyr Arg Asp Leu Lys
35 40 45

Ile Trp Glu Leu Arg
50

<210> SEQ ID NO 33
<211> LENGTH: 937
<212> TYPE: PRT
<213> ORGANISM: Artificial Sequence
<220> FEATURE:
<223> OTHER INFORMATION: Protein sequence of LHA-EGFv1 (Xa activation)

<400> SEQUENCE: 33

Met Glu Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

-continued

```
Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Ile Asp Gly Arg Asn Lys Ala
        435                 440                 445

Leu Asn Leu Gln Cys Ile Lys Val Asn Asn Trp Asp Leu Phe Phe Ser
    450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Glu Asn Ile Ser Leu Asp
                485                 490                 495

Leu Ile Gln Gln Tyr Tyr Leu Thr Phe Asn Phe Asp Asn Glu Pro Glu
            500                 505                 510

Asn Ile Ser Ile Glu Asn Leu Ser Ser Asp Ile Ile Gly Gln Leu Glu
        515                 520                 525

Leu Met Pro Asn Ile Glu Arg Phe Pro Asn Gly Lys Lys Tyr Glu Leu
    530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
            580                 585                 590

Val Asn Lys Ala Thr Glu Ala Ala Met Phe Leu Gly Trp Val Glu Gln
        595                 600                 605
```

```
Leu Val Tyr Asp Phe Thr Asp Glu Thr Ser Glu Val Ser Thr Thr Asp
    610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655

Phe Ser Gly Ala Val Ile Leu Leu Glu Phe Ile Pro Glu Ile Ala Ile
            660                 665                 670

Pro Val Leu Gly Thr Phe Ala Leu Val Ser Tyr Ile Ala Asn Lys Val
        675                 680                 685

Leu Thr Val Gln Thr Ile Asp Asn Ala Leu Ser Lys Arg Asn Glu Lys
    690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
            740                 745                 750

Tyr Thr Glu Glu Glu Lys Asn Asn Ile Asn Phe Asn Ile Asp Asp Leu
        755                 760                 765

Ser Ser Lys Leu Asn Glu Ser Ile Asn Lys Ala Met Ile Asn Ile Asn
    770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
            820                 825                 830

Val Asp Arg Leu Lys Asp Lys Val Asn Asn Thr Leu Ser Thr Asp Ile
        835                 840                 845

Pro Phe Gln Leu Ser Lys Tyr Val Asp Asn Gln Arg Leu Leu Ser Thr
    850                 855                 860

Leu Glu Gly Gly Gly Gly Ser Gly Gly Gly Gly Ser Gly Gly Gly Gly
865                 870                 875                 880

Ser Ala Leu Asp Asn Ser Asp Ser Glu Cys Pro Leu Ser His Asp Gln
                885                 890                 895

Tyr Cys Leu His Asp Gly Val Cys Met Tyr Ile Glu Ala Leu Asp Lys
            900                 905                 910

Tyr Ala Cys Asn Cys Val Val Gly Tyr Ile Gly Glu Arg Cys Gln Tyr
        915                 920                 925

Arg Asp Leu Lys Trp Trp Glu Leu Arg
    930                 935
```

<210> SEQ ID NO 34
<211> LENGTH: 53
<212> TYPE: PRT
<213> ORGANISM: Artificial Sequence
<220> FEATURE:
<223> OTHER INFORMATION: EGF_H16Q_W49I

<400> SEQUENCE: 34

```
Asn Ser Asp Ser Glu Cys Pro Leu Ser His Asp Gly Tyr Cys Leu Gln
1               5                   10                  15

Asp Gly Val Cys Met Tyr Ile Glu Ala Leu Asp Lys Tyr Ala Cys Asn
            20                  25                  30
```

Cys Val Val Gly Tyr Ile Gly Glu Arg Cys Gln Tyr Arg Asp Leu Lys
35 40 45

Ile Trp Glu Leu Arg
50

<210> SEQ ID NO 35
<211> LENGTH: 937
<212> TYPE: PRT
<213> ORGANISM: Artificial Sequence
<220> FEATURE:
<223> OTHER INFORMATION: Protein sequence of LHA-EGFv2 (Xa activation)

<400> SEQUENCE: 35

Met Glu Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

Leu Ile His Ala Gly His Arg Leu Tyr Gly Ile Ala Ile Asn Pro Asn
225 230 235 240

Arg Val Phe Lys Val Asn Thr Asn Ala Tyr Tyr Glu Met Ser Gly Leu
245 250 255

Glu Val Ser Phe Glu Glu Leu Arg Thr Phe Gly Gly His Asp Ala Lys
260 265 270

Phe Ile Asp Ser Leu Gln Glu Asn Glu Phe Arg Leu Tyr Tyr Tyr Asn
275 280 285

Lys Phe Lys Asp Ile Ala Ser Thr Leu Asn Lys Ala Lys Ser Ile Val
290 295 300

Gly Thr Thr Ala Ser Leu Gln Tyr Met Lys Asn Val Phe Lys Glu Lys
305 310 315 320

Tyr Leu Leu Ser Glu Asp Thr Ser Gly Lys Phe Ser Val Asp Lys Leu
325 330 335

Lys Phe Asp Lys Leu Tyr Lys Met Leu Thr Glu Ile Tyr Thr Glu Asp

-continued

```
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Ile Asp Gly Arg Asn Lys Ala
        435                 440                 445

Leu Asn Leu Gln Cys Ile Lys Val Asn Asn Trp Asp Leu Phe Phe Ser
    450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Glu Asn Ile Ser Leu Asp
                485                 490                 495

Leu Ile Gln Gln Tyr Tyr Leu Thr Phe Asn Phe Asp Asn Glu Pro Glu
            500                 505                 510

Asn Ile Ser Ile Glu Asn Leu Ser Ser Asp Ile Ile Gly Gln Leu Glu
        515                 520                 525

Leu Met Pro Asn Ile Glu Arg Phe Pro Asn Gly Lys Lys Tyr Glu Leu
    530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
            580                 585                 590

Val Asn Lys Ala Thr Glu Ala Ala Met Phe Leu Gly Trp Val Glu Gln
        595                 600                 605

Leu Val Tyr Asp Phe Thr Asp Glu Thr Ser Glu Val Ser Thr Thr Asp
    610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655

Phe Ser Gly Ala Val Ile Leu Leu Glu Phe Ile Pro Glu Ile Ala Ile
            660                 665                 670

Pro Val Leu Gly Thr Phe Ala Leu Val Ser Tyr Ile Ala Asn Lys Val
        675                 680                 685

Leu Thr Val Gln Thr Ile Asp Asn Ala Leu Ser Lys Arg Asn Glu Lys
    690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
            740                 745                 750

Tyr Thr Glu Glu Glu Lys Asn Asn Ile Asn Phe Asn Ile Asp Asp Leu
        755                 760                 765
```

-continued

Ser Ser Lys Leu Asn Glu Ser Ile Asn Lys Ala Met Ile Asn Ile Asn
770 775 780

Lys Phe Leu Asn Gln Cys Ser Val Ser Tyr Leu Met Asn Ser Met Ile
785 790 795 800

Pro Tyr Gly Val Lys Arg Leu Glu Asp Phe Asp Ala Ser Leu Lys Asp
805 810 815

Ala Leu Leu Lys Tyr Ile Tyr Asp Asn Arg Gly Thr Leu Ile Gly Gln
820 825 830

Val Asp Arg Leu Lys Asp Lys Val Asn Asn Thr Leu Ser Thr Asp Ile
835 840 845

Pro Phe Gln Leu Ser Lys Tyr Val Asp Asn Gln Arg Leu Leu Ser Thr
850 855 860

Leu Glu Gly Gly Gly Gly Ser Gly Gly Gly Gly Ser Gly Gly Gly Gly
865 870 875 880

Ser Ala Leu Asp Ser Arg Gly Ser Lys Cys Pro Pro Ser His Asp Gly
885 890 895

Tyr Cys Leu Gln Gly Gly Val Cys Met Tyr Ile Glu Ala Leu Asp Arg
900 905 910

Tyr Ala Cys Asn Cys Val Val Gly Tyr Ala Gly Glu Arg Cys Gln Tyr
915 920 925

Arg Asp Leu Thr Trp Trp Gly Arg Arg
930 935

<210> SEQ ID NO 36
<211> LENGTH: 53
<212> TYPE: PRT
<213> ORGANISM: Artificial Sequence
<220> FEATURE:
<223> OTHER INFORMATION: EGF_H16N_W50A

<400> SEQUENCE: 36

Asn Ser Asp Ser Glu Cys Pro Leu Ser His Asp Gly Tyr Cys Leu Asn
1 5 10 15

Asp Gly Val Cys Met Tyr Ile Glu Ala Leu Asp Lys Tyr Ala Cys Asn
20 25 30

Cys Val Val Gly Tyr Ile Gly Glu Arg Cys Gln Tyr Arg Asp Leu Lys
35 40 45

Trp Ala Glu Leu Arg
50

<210> SEQ ID NO 37
<211> LENGTH: 938
<212> TYPE: PRT
<213> ORGANISM: Artificial Sequence
<220> FEATURE:
<223> OTHER INFORMATION: Protein sequence of LHA-EGFv3 (enhanced mutation)

<400> SEQUENCE: 37

Met Glu Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

```
Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Leu Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Asp Lys Asn Lys
        435                 440                 445

Ala Leu Asn Leu Gln Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
```

```
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Leu Glu Gly Gly Gly Gly Ser Gly Gly Gly Gly Ser Gly Gly Gly
865                 870                 875                 880

Gly Ser Ala Leu Asp Asn Ser Asp Pro Lys Cys Pro Leu Ser His Glu
                885                 890                 895

Gly Tyr Cys Leu Asn Asp Gly Val Cys Met Tyr Ile Gly Thr Leu Asp
            900                 905                 910

Arg Tyr Ala Cys Asn Cys Val Val Gly Tyr Val Gly Glu Arg Cys Gln
        915                 920                 925
```

Tyr Arg Asp Leu Lys Leu Ala Glu Leu Arg
    930                 935

<210> SEQ ID NO 38
<211> LENGTH: 53
<212> TYPE: PRT
<213> ORGANISM: Artificial Sequence
<220> FEATURE:
<223> OTHER INFORMATION: EGF_H16Q_W50A

<400> SEQUENCE: 38

Asn Ser Asp Ser Glu Cys Pro Leu Ser His Asp Gly Tyr Cys Leu Gln
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Ala Glu Leu Arg
    50

<210> SEQ ID NO 39
<211> LENGTH: 938
<212> TYPE: PRT
<213> ORGANISM: Artificial Sequence
<220> FEATURE:
<223> OTHER INFORMATION: Protein sequence of LHA-EGFv4

<400> SEQUENCE: 39

Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

-continued

```
Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Asp Lys Asn Lys
        435                 440                 445

Ala Leu Asn Leu Gln Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670
```

```
Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Leu Glu Gly Gly Gly Gly Ser Gly Gly Gly Gly Ser Gly Gly Gly
865                 870                 875                 880

Gly Ser Ala Leu Asp Asn Ser Tyr Ser Glu Cys Pro Pro Ser Tyr Asp
                885                 890                 895

Gly Tyr Cys Leu His Asp Gly Val Cys Arg Tyr Ile Glu Ala Leu Asp
            900                 905                 910

Ser Tyr Ala Cys Asn Cys Val Val Gly Tyr Ala Gly Glu Arg Cys Gln
        915                 920                 925

Tyr Arg Asp Leu Arg Trp Trp Gly Arg Arg
    930                 935
```

<210> SEQ ID NO 40
<211> LENGTH: 53
<212> TYPE: PRT
<213> ORGANISM: Artificial Sequence
<220> FEATURE:
<223> OTHER INFORMATION: EGF_H16N_W49L_W50A

<400> SEQUENCE: 40

```
Asn Ser Asp Ser Glu Cys Pro Leu Ser His Asp Gly Tyr Cys Leu Asn
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Leu Ala Glu Leu Arg
    50
```

<210> SEQ ID NO 41
<211> LENGTH: 938
<212> TYPE: PRT
<213> ORGANISM: Artificial Sequence
<220> FEATURE:

<223> OTHER INFORMATION: Protein sequence of LHA-EGFv5

<400> SEQUENCE: 41

```
Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
```

-continued

```
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Asp Lys Asn Lys
        435                 440                 445

Ala Leu Asn Leu Gln Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830
```

Gln Val Asp Arg Leu Lys Asp Lys Val Asn Asn Thr Leu Ser Thr Asp
835 840 845

Ile Pro Phe Gln Leu Ser Lys Tyr Val Asp Asn Gln Arg Leu Leu Ser
850 855 860

Thr Leu Glu Gly Gly Gly Gly Ser Gly Gly Gly Gly Ser Gly Gly Gly
865 870 875 880

Gly Ser Ala Leu Asp Asn Ser Asp Ser Gly Cys Pro Ser Phe His Asp
885 890 895

Gly Tyr Cys Leu Asn Gly Gly Val Cys Met Tyr Ile Glu Ala Leu Asp
900 905 910

Lys Tyr Ala Cys Asn Cys Val Ile Gly Tyr Asn Gly Asp Arg Cys Gln
915 920 925

Thr Arg Asp Leu Lys Trp Trp Glu Leu Arg
930 935

<210> SEQ ID NO 42
<211> LENGTH: 53
<212> TYPE: PRT
<213> ORGANISM: Artificial Sequence
<220> FEATURE:
<223> OTHER INFORMATION: EGF_H16Q_W49L_W50A

<400> SEQUENCE: 42

Asn Ser Asp Ser Glu Cys Pro Leu Ser His Asp Gly Tyr Cys Leu Gln
1 5 10 15

Asp Gly Val Cys Met Tyr Ile Glu Ala Leu Asp Lys Tyr Ala Cys Asn
20 25 30

Cys Val Val Gly Tyr Ile Gly Glu Arg Cys Gln Tyr Arg Asp Leu Lys
35 40 45

Leu Ala Glu Leu Arg
50

<210> SEQ ID NO 43
<211> LENGTH: 938
<212> TYPE: PRT
<213> ORGANISM: Artificial Sequence
<220> FEATURE:
<223> OTHER INFORMATION: Protein sequence of LHA-EGFv6

<400> SEQUENCE: 43

Met Glu Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Asp Lys Asn Lys
        435                 440                 445

Ala Leu Asn Leu Gln Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575
```

```
Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Leu Glu Gly Gly Gly Gly Ser Gly Gly Gly Gly Ser Gly Gly Gly
865                 870                 875                 880

Gly Ser Ala Leu Asp Asn Ser Asp Ser Glu Cys Pro Leu Ser His Asp
                885                 890                 895

Gln Tyr Cys Leu His Asp Gly Val Cys Met Tyr Ile Glu Ala Leu Asp
            900                 905                 910

Lys Tyr Ala Cys Asn Cys Val Val Gly Tyr Ile Gly Glu Arg Cys Gln
        915                 920                 925

Tyr Arg Asp Leu Lys Trp Trp Glu Leu Arg
    930                 935
```

<210> SEQ ID NO 44
<211> LENGTH: 53
<212> TYPE: PRT
<213> ORGANISM: Artificial Sequence
<220> FEATURE:
<223> OTHER INFORMATION: EGF_H16N_W49I_W50A

<400> SEQUENCE: 44

```
Asn Ser Asp Ser Glu Cys Pro Leu Ser His Asp Gly Tyr Cys Leu Asn
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Ile Ala Glu Leu Arg
    50


<210> SEQ ID NO 45
<211> LENGTH: 939
<212> TYPE: PRT
<213> ORGANISM: Artificial Sequence
<220> FEATURE:
<223> OTHER INFORMATION: Protein sequence of LHC-EGFv7

<400> SEQUENCE: 45

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
```

-continued

```
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735
```

```
Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Gly Ser Gly Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu Asp Asp Gly Val Cys Met Tyr Ile Glu Ala Leu
            900                 905                 910

Asp Lys Tyr Ala Cys Asn Cys Val Val Gly Tyr Ile Gly Glu Arg Cys
        915                 920                 925

Gln Tyr Arg Asp Leu Lys Trp Trp Glu Leu Arg
    930                 935


<210> SEQ ID NO 46
<211> LENGTH: 53
<212> TYPE: PRT
<213> ORGANISM: Artificial Sequence
<220> FEATURE:
<223> OTHER INFORMATION: EGF_H16Q_W49I_W50A

<400> SEQUENCE: 46

Asn Ser Asp Ser Glu Cys Pro Leu Ser His Asp Gly Tyr Cys Leu Gln
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Ile Ala Glu Leu Arg
    50


<210> SEQ ID NO 47
<211> LENGTH: 939
<212> TYPE: PRT
<213> ORGANISM: Artificial Sequence
<220> FEATURE:
<223> OTHER INFORMATION: Protein sequence of LHC-EGFv8

<400> SEQUENCE: 47

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45
```

-continued

```
Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480
```

-continued

```
Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Gly Ser Gly Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu Asp Asp Gly Val Cys Met Tyr Ile Glu Ala Leu
```

-continued

```
            900                 905                 910

Asp Lys Tyr Ala Cys Asn Cys Val Val Gly Tyr Ile Gly Glu Arg Cys
        915                 920                 925

Gln Tyr Arg Asp Leu Lys Trp Trp Glu Leu Arg
    930                 935


<210> SEQ ID NO 48
<211> LENGTH: 53
<212> TYPE: PRT
<213> ORGANISM: Artificial Sequence
<220> FEATURE:
<223> OTHER INFORMATION: EGF_H16N_W49L_W50A_E24G

<400> SEQUENCE: 48

Asn Ser Asp Ser Glu Cys Pro Leu Ser His Asp Gly Tyr Cys Leu Asn
1               5                   10                  15

Asp Gly Val Cys Met Tyr Ile Gly Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Leu Ala Glu Leu Arg
    50


<210> SEQ ID NO 49
<211> LENGTH: 939
<212> TYPE: PRT
<213> ORGANISM: Artificial Sequence
<220> FEATURE:
<223> OTHER INFORMATION: Protein sequence of LHC-EGFv9

<400> SEQUENCE: 49

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
```

-continued

```
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640
```

-continued

```
Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Gly Ser Gly Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu His Asp Gly Val Cys Met Tyr Ile Glu Ala Leu
            900                 905                 910

Asp Lys Tyr Ala Cys Asn Cys Val Val Gly Tyr Ile Gly Glu Arg Cys
        915                 920                 925

Ala Tyr Arg Asp Leu Lys Trp Trp Glu Leu Arg
    930                 935
```

<210> SEQ ID NO 50
<211> LENGTH: 53
<212> TYPE: PRT
<213> ORGANISM: Artificial Sequence
<220> FEATURE:
<223> OTHER INFORMATION: EGF_H16N_W49L_W50A_E24G_A25T

<400> SEQUENCE: 50

```
Asn Ser Asp Ser Glu Cys Pro Leu Ser His Asp Gly Tyr Cys Leu Asn
1               5                   10                  15

Asp Gly Val Cys Met Tyr Ile Gly Thr Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Leu Ala Glu Leu Arg
    50
```

-continued

<210> SEQ ID NO 51
<211> LENGTH: 939
<212> TYPE: PRT
<213> ORGANISM: Artificial Sequence
<220> FEATURE:
<223> OTHER INFORMATION: Protein sequence of LHC-EGFv10

<400> SEQUENCE: 51

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380
```

```
Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
```

```
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Gly Ser Gly Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu Ala Asp Gly Val Cys Met Tyr Ile Glu Ala Leu
            900                 905                 910

Asp Lys Tyr Ala Cys Asn Cys Val Val Gly Tyr Ile Gly Glu Arg Cys
        915                 920                 925

Gln Tyr Arg Asp Leu Lys Trp Trp Glu Leu Arg
    930                 935


<210> SEQ ID NO 52
<211> LENGTH: 53
<212> TYPE: PRT
<213> ORGANISM: Artificial Sequence
<220> FEATURE:
<223> OTHER INFORMATION: EGF_H16N_W49L_W50A_E24G_A25S

<400> SEQUENCE: 52

Asn Ser Asp Ser Glu Cys Pro Leu Ser His Asp Gly Tyr Cys Leu Asn
1               5                   10                  15

Asp Gly Val Cys Met Tyr Ile Gly Ser Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Leu Ala Glu Leu Arg
    50


<210> SEQ ID NO 53
<211> LENGTH: 939
<212> TYPE: PRT
<213> ORGANISM: Artificial Sequence
<220> FEATURE:
<223> OTHER INFORMATION: Protein sequence of LHC-EGFv11

<400> SEQUENCE: 53

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
```

-continued

```
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540
```

```
Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Gly Ser Gly Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Ala His Asp Gly Val Cys Met Tyr Ile Glu Ala Leu
            900                 905                 910

Asp Lys Tyr Ala Cys Asn Cys Val Val Gly Tyr Ile Gly Glu Arg Cys
        915                 920                 925

Gln Tyr Arg Asp Leu Lys Trp Trp Glu Leu Arg
    930                 935
```

<210> SEQ ID NO 54
<211> LENGTH: 53
<212> TYPE: PRT
<213> ORGANISM: Artificial Sequence

<220> FEATURE:
<223> OTHER INFORMATION: EGF_H16N_W49L_W50A_E24G_A25T_K28R

<400> SEQUENCE: 54

```
Asn Ser Asp Ser Glu Cys Pro Leu Ser His Asp Gly Tyr Cys Leu Asn
1               5                   10                  15

Asp Gly Val Cys Met Tyr Ile Gly Thr Leu Asp Arg Tyr Ala Cys Asn
            20                  25                  30

Cys Val Val Gly Tyr Ile Gly Glu Arg Cys Gln Tyr Arg Asp Leu Lys
        35                  40                  45

Leu Ala Glu Leu Arg
    50
```

<210> SEQ ID NO 55
<211> LENGTH: 939
<212> TYPE: PRT
<213> ORGANISM: Artificial Sequence
<220> FEATURE:
<223> OTHER INFORMATION: Protein sequence of LHC-EGFv12

<400> SEQUENCE: 55

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285
```

```
Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
```

705 710 715 720

Asn Asn Ile Ser Tyr Gln Met Tyr Asp Ser Leu Asn Tyr Gln Ala Gly
725 730 735

Ala Ile Lys Ala Lys Ile Asp Leu Glu Tyr Lys Lys Tyr Ser Gly Ser
740 745 750

Asp Lys Glu Asn Ile Lys Ser Gln Val Glu Asn Leu Lys Asn Ser Leu
755 760 765

Asp Val Lys Ile Ser Glu Ala Met Asn Asn Ile Asn Lys Phe Ile Arg
770 775 780

Glu Cys Ser Val Thr Tyr Leu Phe Lys Asn Met Leu Pro Lys Val Ile
785 790 795 800

Asp Glu Leu Asn Glu Phe Asp Arg Asn Thr Lys Ala Lys Leu Ile Asn
805 810 815

Leu Ile Asp Ser His Asn Ile Ile Leu Val Gly Glu Val Asp Lys Leu
820 825 830

Lys Ala Lys Val Asn Asn Ser Phe Gln Asn Thr Ile Pro Phe Asn Ile
835 840 845

Phe Ser Tyr Thr Asn Asn Ser Leu Leu Lys Asp Ile Ile Asn Glu Tyr
850 855 860

Phe Asn Leu Glu Gly Gly Gly Gly Ser Gly Gly Gly Gly Ser Gly Gly
865 870 875 880

Gly Gly Ser Ala Leu Asp Asn Ser Asp Ser Glu Cys Pro Leu Ser His
885 890 895

Asp Gly Tyr Cys Leu His Asp Gly Glu Cys Met Tyr Ile Glu Ala Leu
900 905 910

Asp Lys Tyr Ala Cys Asn Cys Val Val Gly Tyr Ile Gly Glu Arg Cys
915 920 925

Gln Tyr Arg Asp Leu Lys Trp Trp Glu Leu Arg
930 935

<210> SEQ ID NO 56
<211> LENGTH: 53
<212> TYPE: PRT
<213> ORGANISM: Artificial Sequence
<220> FEATURE:
<223> OTHER INFORMATION: EGF_H16N_W49L_W50A_E24G_A25T_K28R_S4P

<400> SEQUENCE: 56

Asn Ser Asp Pro Glu Cys Pro Leu Ser His Asp Gly Tyr Cys Leu Asn
1 5 10 15

Asp Gly Val Cys Met Tyr Ile Gly Thr Leu Asp Arg Tyr Ala Cys Asn
20 25 30

Cys Val Val Gly Tyr Ile Gly Glu Arg Cys Gln Tyr Arg Asp Leu Lys
35 40 45

Leu Ala Glu Leu Arg
50

<210> SEQ ID NO 57
<211> LENGTH: 939
<212> TYPE: PRT
<213> ORGANISM: Artificial Sequence
<220> FEATURE:
<223> OTHER INFORMATION: Protein sequence of LHC-EGFv13

<400> SEQUENCE: 57

Met Pro Ile Thr Ile Asn Asn Phe Asn Tyr Ser Asp Pro Val Asp Asn
1 5 10 15

Lys Asn Ile Leu Tyr Leu Asp Thr His Leu Asn Thr Leu Ala Asn Glu

-continued

```
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Leu Tyr Asn
        435                 440                 445
```

```
Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Gly Ser Gly Gly Gly Gly Ser Gly Gly
865                 870                 875                 880
```

-continued

Gly Gly Ser Ala Leu Asp Asn Ser Asp Ser Glu Cys Pro Leu Ser His
885 890 895

Asp Gly Tyr Cys Leu His Asp Gly Val Cys Met Tyr Ile Glu Ala Leu
900 905 910

Asp Lys Tyr Ala Cys Asn Cys Asp Val Gly Tyr Ile Gly Glu Arg Cys
915 920 925

Gln Tyr Arg Asp Leu Lys Trp Trp Glu Leu Arg
930 935

<210> SEQ ID NO 58
<211> LENGTH: 53
<212> TYPE: PRT
<213> ORGANISM: Artificial Sequence
<220> FEATURE:
<223> OTHER INFORMATION: EGF_H16N_W49L_W50A_E24G_A25T_K28R_S4P_E5K

<400> SEQUENCE: 58

Asn Ser Asp Pro Lys Cys Pro Leu Ser His Asp Gly Tyr Cys Leu Asn
1 5 10 15

Asp Gly Val Cys Met Tyr Ile Gly Thr Leu Asp Arg Tyr Ala Cys Asn
20 25 30

Cys Val Val Gly Tyr Ile Gly Glu Arg Cys Gln Tyr Arg Asp Leu Lys
35 40 45

Leu Ala Glu Leu Arg
50

<210> SEQ ID NO 59
<211> LENGTH: 943
<212> TYPE: PRT
<213> ORGANISM: Artificial Sequence
<220> FEATURE:
<223> OTHER INFORMATION: Protein sequence of LHB-EGFv1

<400> SEQUENCE: 59

Met Pro Val Thr Ile Asn Asn Phe Asn Tyr Asn Asp Pro Ile Asp Asn
1 5 10 15

Asn Asn Ile Ile Met Met Glu Pro Pro Phe Ala Arg Gly Thr Gly Arg
20 25 30

Tyr Tyr Lys Ala Phe Lys Ile Thr Asp Arg Ile Trp Ile Ile Pro Glu
35 40 45

Arg Tyr Thr Phe Gly Tyr Lys Pro Glu Asp Phe Asn Lys Ser Ser Gly
50 55 60

Ile Phe Asn Arg Asp Val Cys Glu Tyr Tyr Asp Pro Asp Tyr Leu Asn
65 70 75 80

Thr Asn Asp Lys Lys Asn Ile Phe Leu Gln Thr Met Ile Lys Leu Phe
85 90 95

Asn Arg Ile Lys Ser Lys Pro Leu Gly Glu Lys Leu Leu Glu Met Ile
100 105 110

Ile Asn Gly Ile Pro Tyr Leu Gly Asp Arg Arg Val Pro Leu Glu Glu
115 120 125

Phe Asn Thr Asn Ile Ala Ser Val Thr Val Asn Lys Leu Ile Ser Asn
130 135 140

Pro Gly Glu Val Glu Arg Lys Lys Gly Ile Phe Ala Asn Leu Ile Ile
145 150 155 160

Phe Gly Pro Gly Pro Val Leu Asn Glu Asn Glu Thr Ile Asp Ile Gly
165 170 175

Ile Gln Asn His Phe Ala Ser Arg Glu Gly Phe Gly Gly Ile Met Gln
180 185 190

-continued

```
Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Val Asp Glu Glu Lys Leu Tyr Asp Asp Asp Asp
        435                 440                 445

Lys Asp Arg Trp Gly Ser Ser Leu Gln Cys Ile Asp Val Asp Asn Glu
    450                 455                 460

Asp Leu Phe Phe Ile Ala Asp Lys Asn Ser Phe Ser Asp Asp Leu Ser
465                 470                 475                 480

Lys Asn Glu Arg Ile Glu Tyr Asn Thr Gln Ser Asn Tyr Ile Glu Asn
                485                 490                 495

Asp Phe Pro Ile Asn Glu Leu Ile Leu Asp Thr Asp Leu Ile Ser Lys
            500                 505                 510

Ile Glu Leu Pro Ser Glu Asn Thr Glu Ser Leu Thr Asp Phe Asn Val
        515                 520                 525

Asp Val Pro Val Tyr Glu Lys Gln Pro Ala Ile Lys Lys Ile Phe Thr
    530                 535                 540

Asp Glu Asn Thr Ile Phe Gln Tyr Leu Tyr Ser Gln Thr Phe Pro Leu
545                 550                 555                 560

Asp Ile Arg Asp Ile Ser Leu Thr Ser Ser Phe Asp Asp Ala Leu Leu
                565                 570                 575

Phe Ser Asn Lys Val Tyr Ser Phe Phe Ser Met Asp Tyr Ile Lys Thr
            580                 585                 590

Ala Asn Lys Val Val Glu Ala Gly Leu Phe Ala Gly Trp Val Lys Gln
        595                 600                 605

Ile Val Asn Asp Phe Val Ile Glu Ala Asn Lys Ser Asn Thr Met Asp
```

```
    610                 615                 620

Ala Ile Ala Asp Ile Ser Leu Ile Val Pro Tyr Ile Gly Leu Ala Leu
625                 630                 635                 640

Asn Val Gly Asn Glu Thr Ala Lys Gly Asn Phe Glu Asn Ala Phe Glu
                645                 650                 655

Ile Ala Gly Ala Ser Ile Leu Leu Glu Phe Ile Pro Glu Leu Leu Ile
            660                 665                 670

Pro Val Val Gly Ala Phe Leu Leu Glu Ser Tyr Ile Asp Asn Lys Asn
        675                 680                 685

Lys Ile Ile Lys Thr Ile Asp Asn Ala Leu Thr Lys Arg Asn Glu Lys
    690                 695                 700

Trp Ser Asp Met Tyr Gly Leu Ile Val Ala Gln Trp Leu Ser Thr Val
705                 710                 715                 720

Asn Thr Gln Phe Tyr Thr Ile Lys Glu Gly Met Tyr Lys Ala Leu Asn
                725                 730                 735

Tyr Gln Ala Gln Ala Leu Glu Glu Ile Ile Lys Tyr Arg Tyr Asn Ile
            740                 745                 750

Tyr Ser Glu Lys Glu Lys Ser Asn Ile Asn Ile Asp Phe Asn Asp Ile
        755                 760                 765

Asn Ser Lys Leu Asn Glu Gly Ile Asn Gln Ala Ile Asp Asn Ile Asn
    770                 775                 780

Asn Phe Ile Asn Gly Cys Ser Val Ser Tyr Leu Met Lys Lys Met Ile
785                 790                 795                 800

Pro Leu Ala Val Glu Lys Leu Leu Asp Phe Asp Asn Thr Leu Lys Lys
                805                 810                 815

Asn Leu Leu Asn Tyr Ile Asp Glu Asn Lys Leu Tyr Leu Ile Gly Ser
            820                 825                 830

Ala Glu Tyr Glu Lys Ser Lys Val Asn Lys Tyr Leu Lys Thr Ile Met
        835                 840                 845

Pro Phe Asp Leu Ser Ile Tyr Thr Asn Asp Thr Ile Leu Ile Glu Met
    850                 855                 860

Phe Asn Lys Tyr Asn Ser Leu Glu Gly Gly Gly Gly Ser Gly Gly Gly
865                 870                 875                 880

Gly Ser Gly Gly Gly Gly Ser Ala Leu Asp Ser Arg Gly Ser Lys Cys
                885                 890                 895

Pro Pro Ser His Asp Gly Tyr Cys Leu Gln Gly Gly Val Cys Met Tyr
            900                 905                 910

Ile Glu Ala Leu Asp Arg Tyr Ala Cys Asn Cys Val Val Gly Tyr Ala
        915                 920                 925

Gly Glu Arg Cys Gln Tyr Arg Asp Leu Thr Trp Trp Gly Arg Arg
    930                 935                 940


<210> SEQ ID NO 60
<211> LENGTH: 53
<212> TYPE: PRT
<213> ORGANISM: Artificial Sequence
<220> FEATURE:
<223> OTHER INFORMATION: EGFv3

<400> SEQUENCE: 60

Asn Ser Asp Pro Lys Cys Pro Leu Ser His Glu Gly Tyr Cys Leu Asn
1               5                   10                  15

Asp Gly Val Cys Met Tyr Ile Gly Thr Leu Asp Arg Tyr Ala Cys Asn
            20                  25                  30

Cys Val Val Gly Tyr Val Gly Glu Arg Cys Gln Tyr Arg Asp Leu Lys
        35                  40                  45
```

Leu Ala Glu Leu Arg
    50

<210> SEQ ID NO 61
<211> LENGTH: 943
<212> TYPE: PRT
<213> ORGANISM: Artificial Sequence
<220> FEATURE:
<223> OTHER INFORMATION: Protein sequence of LHB-EGFv5

<400> SEQUENCE: 61

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350
```

```
Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Val Asp Glu Glu Lys Leu Tyr Asp Asp Asp Asp
        435                 440                 445

Lys Asp Arg Trp Gly Ser Ser Leu Gln Cys Ile Asp Val Asp Asn Glu
    450                 455                 460

Asp Leu Phe Phe Ile Ala Asp Lys Asn Ser Phe Ser Asp Asp Leu Ser
465                 470                 475                 480

Lys Asn Glu Arg Ile Glu Tyr Asn Thr Gln Ser Asn Tyr Ile Glu Asn
                485                 490                 495

Asp Phe Pro Ile Asn Glu Leu Ile Leu Asp Thr Asp Leu Ile Ser Lys
            500                 505                 510

Ile Glu Leu Pro Ser Glu Asn Thr Glu Ser Leu Thr Asp Phe Asn Val
        515                 520                 525

Asp Val Pro Val Tyr Glu Lys Gln Pro Ala Ile Lys Lys Ile Phe Thr
    530                 535                 540

Asp Glu Asn Thr Ile Phe Gln Tyr Leu Tyr Ser Gln Thr Phe Pro Leu
545                 550                 555                 560

Asp Ile Arg Asp Ile Ser Leu Thr Ser Ser Phe Asp Asp Ala Leu Leu
                565                 570                 575

Phe Ser Asn Lys Val Tyr Ser Phe Phe Ser Met Asp Tyr Ile Lys Thr
            580                 585                 590

Ala Asn Lys Val Val Glu Ala Gly Leu Phe Ala Gly Trp Val Lys Gln
        595                 600                 605

Ile Val Asn Asp Phe Val Ile Glu Ala Asn Lys Ser Asn Thr Met Asp
    610                 615                 620

Ala Ile Ala Asp Ile Ser Leu Ile Val Pro Tyr Ile Gly Leu Ala Leu
625                 630                 635                 640

Asn Val Gly Asn Glu Thr Ala Lys Gly Asn Phe Glu Asn Ala Phe Glu
                645                 650                 655

Ile Ala Gly Ala Ser Ile Leu Leu Glu Phe Ile Pro Glu Leu Leu Ile
            660                 665                 670

Pro Val Val Gly Ala Phe Leu Leu Glu Ser Tyr Ile Asp Asn Lys Asn
        675                 680                 685

Lys Ile Ile Lys Thr Ile Asp Asn Ala Leu Thr Lys Arg Asn Glu Lys
    690                 695                 700

Trp Ser Asp Met Tyr Gly Leu Ile Val Ala Gln Trp Leu Ser Thr Val
705                 710                 715                 720

Asn Thr Gln Phe Tyr Thr Ile Lys Glu Gly Met Tyr Lys Ala Leu Asn
                725                 730                 735

Tyr Gln Ala Gln Ala Leu Glu Glu Ile Ile Lys Tyr Arg Tyr Asn Ile
            740                 745                 750

Tyr Ser Glu Lys Glu Lys Ser Asn Ile Asn Ile Asp Phe Asn Asp Ile
        755                 760                 765

Asn Ser Lys Leu Asn Glu Gly Ile Asn Gln Ala Ile Asp Asn Ile Asn
    770                 775                 780
```

Asn Phe Ile Asn Gly Cys Ser Val Ser Tyr Leu Met Lys Lys Met Ile
785 790 795 800

Pro Leu Ala Val Glu Lys Leu Leu Asp Phe Asp Asn Thr Leu Lys Lys
805 810 815

Asn Leu Leu Asn Tyr Ile Asp Glu Asn Lys Leu Tyr Leu Ile Gly Ser
820 825 830

Ala Glu Tyr Glu Lys Ser Lys Val Asn Lys Tyr Leu Lys Thr Ile Met
835 840 845

Pro Phe Asp Leu Ser Ile Tyr Thr Asn Asp Thr Ile Leu Ile Glu Met
850 855 860

Phe Asn Lys Tyr Asn Ser Leu Glu Gly Gly Gly Gly Ser Gly Gly Gly
865 870 875 880

Gly Ser Gly Gly Gly Gly Ser Ala Leu Asp Asn Ser Asp Ser Gly Cys
885 890 895

Pro Ser Phe His Asp Gly Tyr Cys Leu Asn Gly Gly Val Cys Met Tyr
900 905 910

Ile Glu Ala Leu Asp Lys Tyr Ala Cys Asn Cys Val Ile Gly Tyr Asn
915 920 925

Gly Asp Arg Cys Gln Thr Arg Asp Leu Lys Trp Trp Glu Leu Arg
930 935 940

<210> SEQ ID NO 62
<211> LENGTH: 949
<212> TYPE: PRT
<213> ORGANISM: Artificial Sequence
<220> FEATURE:
<223> OTHER INFORMATION: Protein sequence of Tetanus LHN-EGFv1

<400> SEQUENCE: 62

Met Pro Ile Thr Ile Asn Asn Phe Arg Tyr Ser Asp Pro Val Asn Asn
1 5 10 15

Asp Thr Ile Ile Met Met Glu Pro Pro Tyr Cys Lys Gly Leu Asp Ile
20 25 30

Tyr Tyr Lys Ala Phe Lys Ile Thr Asp Arg Ile Trp Ile Val Pro Glu
35 40 45

Arg Tyr Glu Phe Gly Thr Lys Pro Glu Asp Phe Asn Pro Pro Ser Ser
50 55 60

Leu Ile Glu Gly Ala Ser Glu Tyr Tyr Asp Pro Asn Tyr Leu Arg Thr
65 70 75 80

Asp Ser Asp Lys Asp Arg Phe Leu Gln Thr Met Val Lys Leu Phe Asn
85 90 95

Arg Ile Lys Asn Asn Val Ala Gly Glu Ala Leu Leu Asp Lys Ile Ile
100 105 110

Asn Ala Ile Pro Tyr Leu Gly Asn Ser Tyr Ser Leu Leu Asp Lys Phe
115 120 125

Asp Thr Asn Ser Asn Ser Val Ser Phe Asn Leu Leu Glu Gln Asp Pro
130 135 140

Ser Gly Ala Thr Thr Lys Ser Ala Met Leu Thr Asn Leu Ile Ile Phe
145 150 155 160

Gly Pro Gly Pro Val Leu Asn Lys Asn Glu Val Arg Gly Ile Val Leu
165 170 175

Arg Val Asp Asn Lys Asn Tyr Phe Pro Cys Arg Asp Gly Phe Gly Ser
180 185 190

Ile Met Gln Met Ala Phe Cys Pro Glu Tyr Val Pro Thr Phe Asp Asn
195 200 205

-continued

```
Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Val Asp Gly Ile Ile Thr Ser Lys Thr
        435                 440                 445

Lys Ser Asp Asp Asp Asp Lys Asn Lys Ala Leu Asn Leu Gln Cys Ile
    450                 455                 460

Lys Ile Lys Asn Glu Asp Leu Thr Phe Ile Ala Glu Lys Asn Ser Phe
465                 470                 475                 480

Ser Glu Glu Pro Phe Gln Asp Glu Ile Val Ser Tyr Asn Thr Lys Asn
                485                 490                 495

Lys Pro Leu Asn Phe Asn Tyr Ser Leu Asp Lys Ile Ile Val Asp Tyr
            500                 505                 510

Asn Leu Gln Ser Lys Ile Thr Leu Pro Asn Asp Arg Thr Thr Pro Val
        515                 520                 525

Thr Lys Gly Ile Pro Tyr Ala Pro Glu Tyr Lys Ser Asn Ala Ala Ser
    530                 535                 540

Thr Ile Glu Ile His Asn Ile Asp Asp Asn Thr Ile Tyr Gln Tyr Leu
545                 550                 555                 560

Tyr Ala Gln Lys Ser Pro Thr Thr Leu Gln Arg Ile Thr Met Thr Asn
                565                 570                 575

Ser Val Asp Asp Ala Leu Ile Asn Ser Thr Lys Ile Tyr Ser Tyr Phe
            580                 585                 590

Pro Ser Val Ile Ser Lys Val Asn Gln Gly Ala Gln Gly Ile Leu Phe
        595                 600                 605

Leu Gln Trp Val Arg Asp Ile Ile Asp Asp Phe Thr Asn Glu Ser Ser
    610                 615                 620

Gln Lys Thr Thr Ile Asp Lys Ile Ser Asp Val Ser Thr Ile Val Pro
625                 630                 635                 640
```

Tyr Ile Gly Pro Ala Leu Asn Ile Val Lys Gln Gly Tyr Glu Gly Asn
645 650 655

Phe Ile Gly Ala Leu Glu Thr Thr Gly Val Val Leu Leu Leu Glu Tyr
660 665 670

Ile Pro Glu Ile Thr Leu Pro Val Ile Ala Ala Leu Ser Ile Ala Glu
675 680 685

Ser Ser Thr Gln Lys Glu Lys Ile Ile Lys Thr Ile Asp Asn Phe Leu
690 695 700

Glu Lys Arg Tyr Glu Lys Trp Ile Glu Val Tyr Lys Leu Val Lys Ala
705 710 715 720

Lys Trp Leu Gly Thr Val Asn Thr Gln Phe Gln Lys Arg Ser Tyr Gln
725 730 735

Met Tyr Arg Ser Leu Glu Tyr Gln Val Asp Ala Ile Lys Lys Ile Ile
740 745 750

Asp Tyr Glu Tyr Lys Ile Tyr Ser Gly Pro Asp Lys Glu Gln Ile Ala
755 760 765

Asp Glu Ile Asn Asn Leu Lys Asn Lys Leu Glu Glu Lys Ala Asn Lys
770 775 780

Ala Met Ile Asn Ile Asn Ile Phe Met Arg Glu Ser Ser Arg Ser Phe
785 790 795 800

Leu Val Asn Gln Met Ile Asn Glu Ala Lys Lys Gln Leu Leu Glu Phe
805 810 815

Asp Thr Gln Ser Lys Asn Ile Leu Met Gln Tyr Ile Lys Ala Asn Ser
820 825 830

Lys Phe Ile Gly Ile Thr Glu Leu Lys Lys Leu Glu Ser Lys Ile Asn
835 840 845

Lys Val Phe Ser Thr Pro Ile Pro Phe Ser Tyr Ser Lys Asn Leu Asp
850 855 860

Cys Trp Val Asp Asn Glu Glu Asp Ile Asp Val Gly Leu Glu Gly Gly
865 870 875 880

Gly Gly Ser Gly Gly Gly Gly Ser Gly Gly Gly Gly Ser Ala Leu Asp
885 890 895

Asn Ser Asp Ser Glu Cys Pro Leu Ser His Asp Gln Tyr Cys Leu His
900 905 910

Asp Gly Val Cys Met Tyr Ile Glu Ala Leu Asp Lys Tyr Ala Cys Asn
915 920 925

Cys Val Val Gly Tyr Ile Gly Glu Arg Cys Gln Tyr Arg Asp Leu Lys
930 935 940

Trp Trp Glu Leu Arg
945

<210> SEQ ID NO 63
<211> LENGTH: 945
<212> TYPE: PRT
<213> ORGANISM: Artificial Sequence
<220> FEATURE:
<223> OTHER INFORMATION: Protein sequence of LHD-EGFv6 (protease sensitivity site)

<400> SEQUENCE: 63

Met Thr Trp Pro Val Lys Asp Phe Asn Tyr Ser Asp Pro Val Asn Asp
1 5 10 15

Asn Asp Ile Leu Tyr Leu Arg Ile Pro Gln Asn Lys Leu Ile Thr Thr
20 25 30

Pro Val Lys Ala Phe Met Ile Thr Gln Asn Ile Trp Val Ile Pro Glu
35 40 45

```
Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Leu Asp Gly Arg Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Val Asp Lys Ser Glu Glu Lys Leu Tyr Asp Asp
        435                 440                 445

Asp Asp Lys Asp Arg Trp Gly Ser Ser Leu Gln Cys Ile Lys Val Lys
    450                 455                 460

Asn Asn Arg Leu Pro Tyr Val Ala Asp Lys Asp Ser Ile Ser Gln Glu
```

-continued

```
465                 470                 475                 480

Ile Phe Glu Asn Lys Ile Ile Thr Asp Glu Thr Asn Val Gln Asn Tyr
                485                 490                 495

Ser Asp Lys Phe Ser Leu Asp Glu Ser Ile Leu Asp Gly Gln Val Pro
            500                 505                 510

Ile Asn Pro Glu Ile Val Asp Pro Leu Leu Pro Asn Val Asn Met Glu
        515                 520                 525

Pro Leu Asn Leu Pro Gly Glu Glu Ile Val Phe Tyr Asp Asp Ile Thr
    530                 535                 540

Lys Tyr Val Asp Tyr Leu Asn Ser Tyr Tyr Tyr Leu Glu Ser Gln Lys
545                 550                 555                 560

Leu Ser Asn Asn Val Glu Asn Ile Thr Leu Thr Thr Ser Val Glu Glu
                565                 570                 575

Ala Leu Gly Tyr Ser Asn Lys Ile Tyr Thr Phe Leu Pro Ser Leu Ala
            580                 585                 590

Glu Lys Val Asn Lys Gly Val Gln Ala Gly Leu Phe Leu Asn Trp Ala
        595                 600                 605

Asn Glu Val Val Glu Asp Phe Thr Thr Asn Ile Met Lys Lys Asp Thr
    610                 615                 620

Leu Asp Lys Ile Ser Asp Val Ser Val Ile Ile Pro Tyr Ile Gly Pro
625                 630                 635                 640

Ala Leu Asn Ile Gly Asn Ser Ala Leu Arg Gly Asn Phe Asn Gln Ala
                645                 650                 655

Phe Ala Thr Ala Gly Val Ala Phe Leu Leu Glu Gly Phe Pro Glu Phe
            660                 665                 670

Thr Ile Pro Ala Leu Gly Val Phe Thr Phe Tyr Ser Ser Ile Gln Glu
        675                 680                 685

Arg Glu Lys Ile Ile Lys Thr Ile Glu Asn Cys Leu Glu Gln Arg Val
    690                 695                 700

Lys Arg Trp Lys Asp Ser Tyr Gln Trp Met Val Ser Asn Trp Leu Ser
705                 710                 715                 720

Arg Ile Thr Thr Gln Phe Asn His Ile Asn Tyr Gln Met Tyr Asp Ser
                725                 730                 735

Leu Ser Tyr Gln Ala Asp Ala Ile Lys Ala Lys Ile Asp Leu Glu Tyr
            740                 745                 750

Lys Lys Tyr Ser Gly Ser Asp Lys Glu Asn Ile Lys Ser Gln Val Glu
        755                 760                 765

Asn Leu Lys Asn Ser Leu Asp Val Lys Ile Ser Glu Ala Met Asn Asn
    770                 775                 780

Ile Asn Lys Phe Ile Arg Glu Cys Ser Val Thr Tyr Leu Phe Lys Asn
785                 790                 795                 800

Met Leu Pro Lys Val Ile Asp Glu Leu Asn Lys Phe Asp Leu Arg Thr
                805                 810                 815

Lys Thr Glu Leu Ile Asn Leu Ile Asp Ser His Asn Ile Ile Leu Val
            820                 825                 830

Gly Glu Val Asp Arg Leu Lys Ala Lys Val Asn Glu Ser Phe Glu Asn
        835                 840                 845

Thr Met Pro Phe Asn Ile Phe Ser Tyr Thr Asn Asn Ser Leu Leu Lys
    850                 855                 860

Asp Ile Ile Asn Glu Tyr Phe Asn Leu Glu Gly Gly Gly Gly Ser Gly
865                 870                 875                 880

Gly Gly Gly Ser Gly Gly Gly Gly Ser Ala Leu Asp Asn Ser Asp Ser
                885                 890                 895
```

```
Glu Cys Pro Leu Ser His Asp Gln Tyr Cys Leu His Asp Gly Val Cys
            900                 905                 910

Met Tyr Ile Glu Ala Leu Asp Lys Tyr Ala Cys Asn Cys Val Val Gly
        915                 920                 925

Tyr Ile Gly Glu Arg Cys Gln Tyr Arg Asp Leu Lys Trp Trp Glu Leu
    930                 935                 940

Arg
945


<210> SEQ ID NO 64
<211> LENGTH: 945
<212> TYPE: PRT
<213> ORGANISM: Artificial Sequence
<220> FEATURE:
<223> OTHER INFORMATION: Protein sequence of LHD-EGFv3

<400> SEQUENCE: 64

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Leu Asp Gly Arg Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
```

-continued

```
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Val Asp Lys Ser Glu Glu Lys Leu Tyr Asp Asp
        435                 440                 445

Asp Asp Lys Asp Arg Trp Gly Ser Ser Leu Gln Cys Ile Lys Val Lys
    450                 455                 460

Asn Asn Arg Leu Pro Tyr Val Ala Asp Lys Asp Ser Ile Ser Gln Glu
465                 470                 475                 480

Ile Phe Glu Asn Lys Ile Ile Thr Asp Glu Thr Asn Val Gln Asn Tyr
                485                 490                 495

Ser Asp Lys Phe Ser Leu Asp Glu Ser Ile Leu Asp Gly Gln Val Pro
            500                 505                 510

Ile Asn Pro Glu Ile Val Asp Pro Leu Leu Pro Asn Val Asn Met Glu
        515                 520                 525

Pro Leu Asn Leu Pro Gly Glu Glu Ile Val Phe Tyr Asp Asp Ile Thr
    530                 535                 540

Lys Tyr Val Asp Tyr Leu Asn Ser Tyr Tyr Tyr Leu Glu Ser Gln Lys
545                 550                 555                 560

Leu Ser Asn Asn Val Glu Asn Ile Thr Leu Thr Thr Ser Val Glu Glu
                565                 570                 575

Ala Leu Gly Tyr Ser Asn Lys Ile Tyr Thr Phe Leu Pro Ser Leu Ala
            580                 585                 590

Glu Lys Val Asn Lys Gly Val Gln Ala Gly Leu Phe Leu Asn Trp Ala
        595                 600                 605

Asn Glu Val Val Glu Asp Phe Thr Thr Asn Ile Met Lys Lys Asp Thr
    610                 615                 620

Leu Asp Lys Ile Ser Asp Val Ser Val Ile Ile Pro Tyr Ile Gly Pro
625                 630                 635                 640

Ala Leu Asn Ile Gly Asn Ser Ala Leu Arg Gly Asn Phe Asn Gln Ala
                645                 650                 655

Phe Ala Thr Ala Gly Val Ala Phe Leu Leu Glu Gly Phe Pro Glu Phe
            660                 665                 670

Thr Ile Pro Ala Leu Gly Val Phe Thr Phe Tyr Ser Ser Ile Gln Glu
        675                 680                 685

Arg Glu Lys Ile Ile Lys Thr Ile Glu Asn Cys Leu Glu Gln Arg Val
    690                 695                 700

Lys Arg Trp Lys Asp Ser Tyr Gln Trp Met Val Ser Asn Trp Leu Ser
705                 710                 715                 720

Arg Ile Thr Thr Gln Phe Asn His Ile Asn Tyr Gln Met Tyr Asp Ser
                725                 730                 735
```

```
Leu Ser Tyr Gln Ala Asp Ala Ile Lys Ala Lys Ile Asp Leu Glu Tyr
            740                 745                 750

Lys Lys Tyr Ser Gly Ser Asp Lys Glu Asn Ile Lys Ser Gln Val Glu
        755                 760                 765

Asn Leu Lys Asn Ser Leu Asp Val Lys Ile Ser Glu Ala Met Asn Asn
    770                 775                 780

Ile Asn Lys Phe Ile Arg Glu Cys Ser Val Thr Tyr Leu Phe Lys Asn
785                 790                 795                 800

Met Leu Pro Lys Val Ile Asp Glu Leu Asn Lys Phe Asp Leu Arg Thr
                805                 810                 815

Lys Thr Glu Leu Ile Asn Leu Ile Asp Ser His Asn Ile Ile Leu Val
            820                 825                 830

Gly Glu Val Asp Arg Leu Lys Ala Lys Val Asn Glu Ser Phe Glu Asn
        835                 840                 845

Thr Met Pro Phe Asn Ile Phe Ser Tyr Thr Asn Asn Ser Leu Leu Lys
    850                 855                 860

Asp Ile Ile Asn Glu Tyr Phe Asn Leu Glu Gly Gly Gly Gly Ser Gly
865                 870                 875                 880

Gly Gly Gly Ser Gly Gly Gly Gly Ser Ala Leu Asp Asn Ser Asp Pro
                885                 890                 895

Lys Cys Pro Leu Ser His Glu Gly Tyr Cys Leu Asn Asp Gly Val Cys
            900                 905                 910

Met Tyr Ile Gly Thr Leu Asp Arg Tyr Ala Cys Asn Cys Val Val Gly
        915                 920                 925

Tyr Val Gly Glu Arg Cys Gln Tyr Arg Asp Leu Lys Leu Ala Glu Leu
    930                 935                 940

Arg
945


<210> SEQ ID NO 65
<211> LENGTH: 945
<212> TYPE: PRT
<213> ORGANISM: Artificial Sequence
<220> FEATURE:
<223> OTHER INFORMATION: Protein sequence of LHD-EGFv11

<400> SEQUENCE: 65

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
```

-continued

```
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Val Asp Lys Ser Glu Glu Lys Leu Tyr Asp Asp
        435                 440                 445

Asp Asp Lys Asp Arg Trp Gly Ser Ser Leu Gln Cys Ile Lys Val Lys
    450                 455                 460

Asn Asn Arg Leu Pro Tyr Val Ala Asp Lys Asp Ser Ile Ser Gln Glu
465                 470                 475                 480

Ile Phe Glu Asn Lys Ile Ile Thr Asp Glu Thr Asn Val Gln Asn Tyr
                485                 490                 495

Ser Asp Lys Phe Ser Leu Asp Glu Ser Ile Leu Asp Gly Gln Val Pro
            500                 505                 510

Ile Asn Pro Glu Ile Val Asp Pro Leu Leu Pro Asn Val Asn Met Glu
        515                 520                 525

Pro Leu Asn Leu Pro Gly Glu Glu Ile Val Phe Tyr Asp Asp Ile Thr
    530                 535                 540

Lys Tyr Val Asp Tyr Leu Asn Ser Tyr Tyr Tyr Leu Glu Ser Gln Lys
545                 550                 555                 560

Leu Ser Asn Asn Val Glu Asn Ile Thr Leu Thr Thr Ser Val Glu Glu
                565                 570                 575
```

```
Ala Leu Gly Tyr Ser Asn Lys Ile Tyr Thr Phe Leu Pro Ser Leu Ala
            580                 585                 590

Glu Lys Val Asn Lys Gly Val Gln Ala Gly Leu Phe Leu Asn Trp Ala
        595                 600                 605

Asn Glu Val Val Glu Asp Phe Thr Thr Asn Ile Met Lys Lys Asp Thr
    610                 615                 620

Leu Asp Lys Ile Ser Asp Val Ser Val Ile Ile Pro Tyr Ile Gly Pro
625                 630                 635                 640

Ala Leu Asn Ile Gly Asn Ser Ala Leu Arg Gly Asn Phe Asn Gln Ala
                645                 650                 655

Phe Ala Thr Ala Gly Val Ala Phe Leu Leu Glu Gly Phe Pro Glu Phe
            660                 665                 670

Thr Ile Pro Ala Leu Gly Val Phe Thr Phe Tyr Ser Ser Ile Gln Glu
        675                 680                 685

Arg Glu Lys Ile Ile Lys Thr Ile Glu Asn Cys Leu Glu Gln Arg Val
    690                 695                 700

Lys Arg Trp Lys Asp Ser Tyr Gln Trp Met Val Ser Asn Trp Leu Ser
705                 710                 715                 720

Arg Ile Thr Thr Gln Phe Asn His Ile Asn Tyr Gln Met Tyr Asp Ser
                725                 730                 735

Leu Ser Tyr Gln Ala Asp Ala Ile Lys Ala Lys Ile Asp Leu Glu Tyr
            740                 745                 750

Lys Lys Tyr Ser Gly Ser Asp Lys Glu Asn Ile Lys Ser Gln Val Glu
        755                 760                 765

Asn Leu Lys Asn Ser Leu Asp Val Lys Ile Ser Glu Ala Met Asn Asn
    770                 775                 780

Ile Asn Lys Phe Ile Arg Glu Cys Ser Val Thr Tyr Leu Phe Lys Asn
785                 790                 795                 800

Met Leu Pro Lys Val Ile Asp Glu Leu Asn Lys Phe Asp Leu Arg Thr
                805                 810                 815

Lys Thr Glu Leu Ile Asn Leu Ile Asp Ser His Asn Ile Ile Leu Val
            820                 825                 830

Gly Glu Val Asp Arg Leu Lys Ala Lys Val Asn Glu Ser Phe Glu Asn
        835                 840                 845

Thr Met Pro Phe Asn Ile Phe Ser Tyr Thr Asn Asn Ser Leu Leu Lys
    850                 855                 860

Asp Ile Ile Asn Glu Tyr Phe Asn Leu Glu Gly Gly Gly Gly Ser Gly
865                 870                 875                 880

Gly Gly Gly Ser Gly Gly Gly Gly Ser Ala Leu Asp Asn Ser Asp Ser
                885                 890                 895

Glu Cys Pro Leu Ser His Asp Gly Tyr Cys Leu Asp Asp Gly Val Cys
            900                 905                 910

Met Tyr Ile Glu Ala Leu Asp Lys Tyr Ala Cys Asn Cys Val Val Gly
        915                 920                 925

Tyr Ile Gly Glu Arg Cys Gln Tyr Arg Asp Leu Lys Trp Trp Glu Leu
    930                 935                 940

Arg
945
```

<210> SEQ ID NO 66
<211> LENGTH: 752
<212> TYPE: PRT
<213> ORGANISM: Artificial Sequence
<220> FEATURE:
<223> OTHER INFORMATION: Protein sequence of M26-IgA1-HC-EGFv3

-continued

<400> SEQUENCE: 66

```
Met Glu Ser Asn Gln Pro Glu Lys Asn Gly Thr Ala Thr Lys Pro Glu
1               5                   10                  15

Asn Ser Gly Asn Thr Thr Ser Glu Asn Gly Gln Thr Glu Pro Glu Lys
            20                  25                  30

Lys Leu Glu Leu Arg Asn Val Ser Asp Ile Glu Leu Tyr Ser Gln Thr
        35                  40                  45

Asn Gly Thr Tyr Arg Gln His Val Ser Leu Asp Gly Ile Pro Glu Asn
    50                  55                  60

Thr Asp Thr Tyr Phe Val Lys Val Lys Ser Ser Ala Phe Lys Asp Val
65                  70                  75                  80

Tyr Ile Pro Val Ala Ser Ile Thr Glu Glu Lys Arg Asn Gly Gln Ser
                85                  90                  95

Val Tyr Lys Ile Thr Ala Lys Ala Glu Lys Leu Gln Gln Glu Leu Glu
            100                 105                 110

Asn Lys Tyr Val Asp Asn Phe Thr Phe Tyr Leu Asp Lys Lys Ala Lys
        115                 120                 125

Glu Glu Asn Thr Asn Phe Thr Ser Phe Ser Asn Leu Val Lys Ala Ile
    130                 135                 140

Asn Gln Asn Pro Ser Gly Thr Tyr His Leu Ala Ala Ser Leu Asn Ala
145                 150                 155                 160

Asn Glu Val Glu Leu Gly Pro Asp Glu Arg Ser Tyr Ile Lys Asp Thr
                165                 170                 175

Phe Thr Gly Arg Leu Ile Gly Glu Lys Asp Gly Lys Asn Tyr Ala Ile
            180                 185                 190

Tyr Asn Leu Lys Lys Pro Leu Phe Glu Asn Leu Ser Gly Ala Thr Val
        195                 200                 205

Glu Lys Leu Ser Leu Lys Asn Val Ala Ile Ser Gly Lys Asn Asp Ile
    210                 215                 220

Gly Ser Leu Ala Asn Glu Ala Thr Asn Gly Thr Lys Ile Lys Gln Val
225                 230                 235                 240

His Val Asp Gly Cys Val Asp Glu Glu Lys Leu Tyr Asp Asp Asp Asp
                245                 250                 255

Lys Asp Arg Trp Gly Ser Ser Leu Gln Cys Arg Glu Leu Leu Val Lys
            260                 265                 270

Asn Thr Asp Leu Pro Phe Ile Gly Asp Ile Ser Asp Val Lys Thr Asp
        275                 280                 285

Ile Phe Leu Arg Lys Asp Ile Asn Glu Glu Thr Glu Val Ile Tyr Tyr
    290                 295                 300

Pro Asp Asn Val Ser Val Asp Gln Val Ile Leu Ser Lys Asn Thr Ser
305                 310                 315                 320

Glu His Gly Gln Leu Asp Leu Leu Tyr Pro Ser Ile Asp Ser Glu Ser
                325                 330                 335

Glu Ile Leu Pro Gly Glu Asn Gln Val Phe Tyr Asp Asn Arg Thr Gln
            340                 345                 350

Asn Val Asp Tyr Leu Asn Ser Tyr Tyr Tyr Leu Glu Ser Gln Lys Leu
        355                 360                 365

Ser Asp Asn Val Glu Asp Phe Thr Phe Thr Arg Ser Ile Glu Glu Ala
    370                 375                 380

Leu Asp Asn Ser Ala Lys Val Tyr Thr Tyr Phe Pro Thr Leu Ala Asn
385                 390                 395                 400

Lys Val Asn Ala Gly Val Gln Gly Gly Leu Phe Leu Met Trp Ala Asn
                405                 410                 415
```

```
Asp Val Val Glu Asp Phe Thr Thr Asn Ile Leu Arg Lys Asp Thr Leu
            420                 425                 430

Asp Lys Ile Ser Asp Val Ser Ala Ile Ile Pro Tyr Ile Gly Pro Ala
        435                 440                 445

Leu Asn Ile Ser Asn Ser Val Arg Arg Gly Asn Phe Thr Glu Ala Phe
    450                 455                 460

Ala Val Thr Gly Val Thr Ile Leu Leu Glu Ala Phe Pro Glu Phe Thr
465                 470                 475                 480

Ile Pro Ala Leu Gly Ala Phe Val Ile Tyr Ser Lys Val Gln Glu Arg
                485                 490                 495

Asn Glu Ile Ile Lys Thr Ile Asp Asn Cys Leu Glu Gln Arg Ile Lys
            500                 505                 510

Arg Trp Lys Asp Ser Tyr Glu Trp Met Met Gly Thr Trp Leu Ser Arg
        515                 520                 525

Ile Ile Thr Gln Phe Asn Asn Ile Ser Tyr Gln Met Tyr Asp Ser Leu
    530                 535                 540

Asn Tyr Gln Ala Gly Ala Ile Lys Ala Lys Ile Asp Leu Glu Tyr Lys
545                 550                 555                 560

Lys Tyr Ser Gly Ser Asp Lys Glu Asn Ile Lys Ser Gln Val Glu Asn
                565                 570                 575

Leu Lys Asn Ser Leu Asp Val Lys Ile Ser Glu Ala Met Asn Asn Ile
            580                 585                 590

Asn Lys Phe Ile Arg Glu Cys Ser Val Thr Tyr Leu Phe Lys Asn Met
        595                 600                 605

Leu Pro Lys Val Ile Asp Glu Leu Asn Glu Phe Asp Arg Asn Thr Lys
    610                 615                 620

Ala Lys Leu Ile Asn Leu Ile Asp Ser His Asn Ile Ile Leu Val Gly
625                 630                 635                 640

Glu Val Asp Lys Leu Lys Ala Lys Val Asn Asn Ser Phe Gln Asn Thr
                645                 650                 655

Ile Pro Phe Asn Ile Phe Ser Tyr Thr Asn Asn Ser Leu Leu Lys Asp
            660                 665                 670

Ile Ile Asn Glu Tyr Phe Asn Leu Glu Gly Gly Gly Gly Ser Gly Gly
        675                 680                 685

Gly Gly Ser Gly Gly Gly Gly Ser Ala Leu Asp Asn Ser Asp Pro Lys
    690                 695                 700

Cys Pro Leu Ser His Glu Gly Tyr Cys Leu Asn Asp Gly Val Cys Met
705                 710                 715                 720

Tyr Ile Gly Thr Leu Asp Arg Tyr Ala Cys Asn Cys Val Val Gly Tyr
                725                 730                 735

Val Gly Glu Arg Cys Gln Tyr Arg Asp Leu Lys Leu Ala Glu Leu Arg
            740                 745                 750
```

<210> SEQ ID NO 67
<211> LENGTH: 752
<212> TYPE: PRT
<213> ORGANISM: Artificial Sequence
<220> FEATURE:
<223> OTHER INFORMATION: Protein sequence of M26-IgA1-HC-EGFv11

<400> SEQUENCE: 67

```
Met Glu Ser Asn Gln Pro Glu Lys Asn Gly Thr Ala Thr Lys Pro Glu
1               5                   10                  15

Asn Ser Gly Asn Thr Thr Ser Glu Asn Gly Gln Thr Glu Pro Glu Lys
            20                  25                  30

Lys Leu Glu Leu Arg Asn Val Ser Asp Ile Glu Leu Tyr Ser Gln Thr
```

```
        35                  40                  45

Asn Gly Thr Tyr Arg Gln His Val Ser Leu Asp Gly Ile Pro Glu Asn
    50                  55                  60

Thr Asp Thr Tyr Phe Val Lys Val Lys Ser Ser Ala Phe Lys Asp Val
65                  70                  75                  80

Tyr Ile Pro Val Ala Ser Ile Thr Glu Glu Lys Arg Asn Gly Gln Ser
                85                  90                  95

Val Tyr Lys Ile Thr Ala Lys Ala Glu Lys Leu Gln Gln Glu Leu Glu
            100                 105                 110

Asn Lys Tyr Val Asp Asn Phe Thr Phe Tyr Leu Asp Lys Lys Ala Lys
        115                 120                 125

Glu Glu Asn Thr Asn Phe Thr Ser Phe Ser Asn Leu Val Lys Ala Ile
    130                 135                 140

Asn Gln Asn Pro Ser Gly Thr Tyr His Leu Ala Ala Ser Leu Asn Ala
145                 150                 155                 160

Asn Glu Val Glu Leu Gly Pro Asp Glu Arg Ser Tyr Ile Lys Asp Thr
                165                 170                 175

Phe Thr Gly Arg Leu Ile Gly Glu Lys Asp Gly Lys Asn Tyr Ala Ile
            180                 185                 190

Tyr Asn Leu Lys Lys Pro Leu Phe Glu Asn Leu Ser Gly Ala Thr Val
        195                 200                 205

Glu Lys Leu Ser Leu Lys Asn Val Ala Ile Ser Gly Lys Asn Asp Ile
    210                 215                 220

Gly Ser Leu Ala Asn Glu Ala Thr Asn Gly Thr Lys Ile Lys Gln Val
225                 230                 235                 240

His Val Asp Gly Cys Val Asp Glu Glu Lys Leu Tyr Asp Asp Asp Asp
                245                 250                 255

Lys Asp Arg Trp Gly Ser Ser Leu Gln Cys Arg Glu Leu Leu Val Lys
            260                 265                 270

Asn Thr Asp Leu Pro Phe Ile Gly Asp Ile Ser Asp Val Lys Thr Asp
        275                 280                 285

Ile Phe Leu Arg Lys Asp Ile Asn Glu Glu Thr Glu Val Ile Tyr Tyr
    290                 295                 300

Pro Asp Asn Val Ser Val Asp Gln Val Ile Leu Ser Lys Asn Thr Ser
305                 310                 315                 320

Glu His Gly Gln Leu Asp Leu Leu Tyr Pro Ser Ile Asp Ser Glu Ser
                325                 330                 335

Glu Ile Leu Pro Gly Glu Asn Gln Val Phe Tyr Asp Asn Arg Thr Gln
            340                 345                 350

Asn Val Asp Tyr Leu Asn Ser Tyr Tyr Tyr Leu Glu Ser Gln Lys Leu
        355                 360                 365

Ser Asp Asn Val Glu Asp Phe Thr Phe Thr Arg Ser Ile Glu Glu Ala
    370                 375                 380

Leu Asp Asn Ser Ala Lys Val Tyr Thr Tyr Phe Pro Thr Leu Ala Asn
385                 390                 395                 400

Lys Val Asn Ala Gly Val Gln Gly Gly Leu Phe Leu Met Trp Ala Asn
                405                 410                 415

Asp Val Val Glu Asp Phe Thr Thr Asn Ile Leu Arg Lys Asp Thr Leu
            420                 425                 430

Asp Lys Ile Ser Asp Val Ser Ala Ile Ile Pro Tyr Ile Gly Pro Ala
        435                 440                 445

Leu Asn Ile Ser Asn Ser Val Arg Arg Gly Asn Phe Thr Glu Ala Phe
    450                 455                 460
```

Ala Val Thr Gly Val Thr Ile Leu Leu Glu Ala Phe Pro Glu Phe Thr
465 470 475 480

Ile Pro Ala Leu Gly Ala Phe Val Ile Tyr Ser Lys Val Gln Glu Arg
485 490 495

Asn Glu Ile Ile Lys Thr Ile Asp Asn Cys Leu Glu Gln Arg Ile Lys
500 505 510

Arg Trp Lys Asp Ser Tyr Glu Trp Met Met Gly Thr Trp Leu Ser Arg
515 520 525

Ile Ile Thr Gln Phe Asn Asn Ile Ser Tyr Gln Met Tyr Asp Ser Leu
530 535 540

Asn Tyr Gln Ala Gly Ala Ile Lys Ala Lys Ile Asp Leu Glu Tyr Lys
545 550 555 560

Lys Tyr Ser Gly Ser Asp Lys Glu Asn Ile Lys Ser Gln Val Glu Asn
565 570 575

Leu Lys Asn Ser Leu Asp Val Lys Ile Ser Glu Ala Met Asn Asn Ile
580 585 590

Asn Lys Phe Ile Arg Glu Cys Ser Val Thr Tyr Leu Phe Lys Asn Met
595 600 605

Leu Pro Lys Val Ile Asp Glu Leu Asn Glu Phe Asp Arg Asn Thr Lys
610 615 620

Ala Lys Leu Ile Asn Leu Ile Asp Ser His Asn Ile Ile Leu Val Gly
625 630 635 640

Glu Val Asp Lys Leu Lys Ala Lys Val Asn Asn Ser Phe Gln Asn Thr
645 650 655

Ile Pro Phe Asn Ile Phe Ser Tyr Thr Asn Asn Ser Leu Leu Lys Asp
660 665 670

Ile Ile Asn Glu Tyr Phe Asn Leu Glu Gly Gly Gly Gly Ser Gly Gly
675 680 685

Gly Gly Ser Gly Gly Gly Gly Ser Ala Leu Asp Asn Ser Asp Ser Glu
690 695 700

Cys Pro Leu Ser His Asp Gly Tyr Cys Ala His Asp Gly Val Cys Met
705 710 715 720

Tyr Ile Glu Ala Leu Asp Lys Tyr Ala Cys Asn Cys Val Val Gly Tyr
725 730 735

Ile Gly Glu Arg Cys Gln Tyr Arg Asp Leu Lys Trp Trp Glu Leu Arg
740 745 750

<210> SEQ ID NO 68
<211> LENGTH: 949
<212> TYPE: PRT
<213> ORGANISM: Artificial Sequence
<220> FEATURE:
<223> OTHER INFORMATION: Protein sequence of Tetanus LHN-EGFv3

<400> SEQUENCE: 68

Met Pro Ile Thr Ile Asn Asn Phe Arg Tyr Ser Asp Pro Val Asn Asn
1 5 10 15

Asp Thr Ile Ile Met Met Glu Pro Pro Tyr Cys Lys Gly Leu Asp Ile
20 25 30

Tyr Tyr Lys Ala Phe Lys Ile Thr Asp Arg Ile Trp Ile Val Pro Glu
35 40 45

Arg Tyr Glu Phe Gly Thr Lys Pro Glu Asp Phe Asn Pro Pro Ser Ser
50 55 60

Leu Ile Glu Gly Ala Ser Glu Tyr Tyr Asp Pro Asn Tyr Leu Arg Thr
65 70 75 80

Asp Ser Asp Lys Asp Arg Phe Leu Gln Thr Met Val Lys Leu Phe Asn

-continued

```
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Val Asp Gly Ile Ile Thr Ser Lys Thr
        435                 440                 445

Lys Ser Asp Asp Asp Asp Lys Asn Lys Ala Leu Asn Leu Gln Cys Ile
    450                 455                 460

Lys Ile Lys Asn Glu Asp Leu Thr Phe Ile Ala Glu Lys Asn Ser Phe
465                 470                 475                 480

Ser Glu Glu Pro Phe Gln Asp Glu Ile Val Ser Tyr Asn Thr Lys Asn
                485                 490                 495

Lys Pro Leu Asn Phe Asn Tyr Ser Leu Asp Lys Ile Ile Val Asp Tyr
            500                 505                 510
```

```
Asn Leu Gln Ser Lys Ile Thr Leu Pro Asn Asp Arg Thr Thr Pro Val
        515                 520                 525

Thr Lys Gly Ile Pro Tyr Ala Pro Glu Tyr Lys Ser Asn Ala Ala Ser
    530                 535                 540

Thr Ile Glu Ile His Asn Ile Asp Asp Asn Thr Ile Tyr Gln Tyr Leu
545                 550                 555                 560

Tyr Ala Gln Lys Ser Pro Thr Thr Leu Gln Arg Ile Thr Met Thr Asn
                565                 570                 575

Ser Val Asp Asp Ala Leu Ile Asn Ser Thr Lys Ile Tyr Ser Tyr Phe
            580                 585                 590

Pro Ser Val Ile Ser Lys Val Asn Gln Gly Ala Gln Gly Ile Leu Phe
        595                 600                 605

Leu Gln Trp Val Arg Asp Ile Ile Asp Asp Phe Thr Asn Glu Ser Ser
    610                 615                 620

Gln Lys Thr Thr Ile Asp Lys Ile Ser Asp Val Ser Thr Ile Val Pro
625                 630                 635                 640

Tyr Ile Gly Pro Ala Leu Asn Ile Val Lys Gln Gly Tyr Glu Gly Asn
                645                 650                 655

Phe Ile Gly Ala Leu Glu Thr Thr Gly Val Val Leu Leu Leu Glu Tyr
            660                 665                 670

Ile Pro Glu Ile Thr Leu Pro Val Ile Ala Ala Leu Ser Ile Ala Glu
        675                 680                 685

Ser Ser Thr Gln Lys Glu Lys Ile Ile Lys Thr Ile Asp Asn Phe Leu
    690                 695                 700

Glu Lys Arg Tyr Glu Lys Trp Ile Glu Val Tyr Lys Leu Val Lys Ala
705                 710                 715                 720

Lys Trp Leu Gly Thr Val Asn Thr Gln Phe Gln Lys Arg Ser Tyr Gln
                725                 730                 735

Met Tyr Arg Ser Leu Glu Tyr Gln Val Asp Ala Ile Lys Lys Ile Ile
            740                 745                 750

Asp Tyr Glu Tyr Lys Ile Tyr Ser Gly Pro Asp Lys Glu Gln Ile Ala
        755                 760                 765

Asp Glu Ile Asn Asn Leu Lys Asn Lys Leu Glu Glu Lys Ala Asn Lys
    770                 775                 780

Ala Met Ile Asn Ile Asn Ile Phe Met Arg Glu Ser Ser Arg Ser Phe
785                 790                 795                 800

Leu Val Asn Gln Met Ile Asn Glu Ala Lys Lys Gln Leu Leu Glu Phe
                805                 810                 815

Asp Thr Gln Ser Lys Asn Ile Leu Met Gln Tyr Ile Lys Ala Asn Ser
            820                 825                 830

Lys Phe Ile Gly Ile Thr Glu Leu Lys Lys Leu Glu Ser Lys Ile Asn
        835                 840                 845

Lys Val Phe Ser Thr Pro Ile Pro Phe Ser Tyr Ser Lys Asn Leu Asp
    850                 855                 860

Cys Trp Val Asp Asn Glu Glu Asp Ile Asp Val Gly Leu Glu Gly Gly
865                 870                 875                 880

Gly Gly Ser Gly Gly Gly Gly Ser Gly Gly Gly Gly Ser Ala Leu Asp
                885                 890                 895

Asn Ser Asp Pro Lys Cys Pro Leu Ser His Glu Gly Tyr Cys Leu Asn
            900                 905                 910

Asp Gly Val Cys Met Tyr Ile Gly Thr Leu Asp Arg Tyr Ala Cys Asn
        915                 920                 925

Cys Val Val Gly Tyr Val Gly Glu Arg Cys Gln Tyr Arg Asp Leu Lys
    930                 935                 940
```

Leu Ala Glu Leu Arg
945

<210> SEQ ID NO 69
<211> LENGTH: 948
<212> TYPE: PRT
<213> ORGANISM: Artificial Sequence
<220> FEATURE:
<223> OTHER INFORMATION: Protein sequence of LHA-CP-EGFv2

<400> SEQUENCE: 69

Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

-continued

```
Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Gly Gly Gly Ser Gly Gly Gly Gly Ser Gly Gly Gly Gly Ser Ala
        435                 440                 445

Asp Asp Asp Asp Lys Ser Arg Gly Ser Lys Cys Pro Pro Ser His Asp
    450                 455                 460

Gly Tyr Cys Leu Gln Gly Gly Val Cys Met Tyr Ile Glu Ala Leu Asp
465                 470                 475                 480

Arg Tyr Ala Cys Asn Cys Val Val Gly Tyr Ala Gly Glu Arg Cys Gln
                485                 490                 495

Tyr Arg Asp Leu Thr Trp Trp Gly Arg Arg Pro Leu Ala Gly Gly Gly
            500                 505                 510

Gly Ser Gly Gly Gly Gly Ser Gly Gly Gly Gly Ser Ala Leu Val Leu
        515                 520                 525

Gln Cys Ile Lys Val Asn Asn Trp Asp Leu Phe Phe Ser Pro Ser Glu
    530                 535                 540

Asp Asn Phe Thr Asn Asp Leu Asn Lys Gly Glu Glu Ile Thr Ser Asp
545                 550                 555                 560

Thr Asn Ile Glu Ala Ala Glu Glu Asn Ile Ser Leu Asp Leu Ile Gln
                565                 570                 575

Gln Tyr Tyr Leu Thr Phe Asn Phe Asp Asn Glu Pro Glu Asn Ile Ser
            580                 585                 590

Ile Glu Asn Leu Ser Ser Asp Ile Ile Gly Gln Leu Glu Leu Met Pro
        595                 600                 605

Asn Ile Glu Arg Phe Pro Asn Gly Lys Lys Tyr Glu Leu Asp Lys Tyr
    610                 615                 620

Thr Met Phe His Tyr Leu Arg Ala Gln Glu Phe Glu His Gly Lys Ser
625                 630                 635                 640

Arg Ile Ala Leu Thr Asn Ser Val Asn Glu Ala Leu Leu Asn Pro Ser
                645                 650                 655

Arg Val Tyr Thr Phe Phe Ser Ser Asp Tyr Val Lys Lys Val Asn Lys
            660                 665                 670

Ala Thr Glu Ala Ala Met Phe Leu Gly Trp Val Glu Gln Leu Val Tyr
        675                 680                 685

Asp Phe Thr Asp Glu Thr Ser Glu Val Ser Thr Thr Asp Lys Ile Ala
    690                 695                 700

Asp Ile Thr Ile Ile Ile Pro Tyr Ile Gly Pro Ala Leu Asn Ile Gly
705                 710                 715                 720

Asn Met Leu Tyr Lys Asp Asp Phe Val Gly Ala Leu Ile Phe Ser Gly
                725                 730                 735

Ala Val Ile Leu Leu Glu Phe Ile Pro Glu Ile Ala Ile Pro Val Leu
            740                 745                 750

Gly Thr Phe Ala Leu Val Ser Tyr Ile Ala Asn Lys Val Leu Thr Val
        755                 760                 765

Gln Thr Ile Asp Asn Ala Leu Ser Lys Arg Asn Glu Lys Trp Asp Glu
    770                 775                 780
```

Val Tyr Lys Tyr Ile Val Thr Asn Trp Leu Ala Lys Val Asn Thr Gln
785 790 795 800

Ile Asp Leu Ile Arg Lys Lys Met Lys Glu Ala Leu Glu Asn Gln Ala
805 810 815

Glu Ala Thr Lys Ala Ile Ile Asn Tyr Gln Tyr Asn Gln Tyr Thr Glu
820 825 830

Glu Glu Lys Asn Asn Ile Asn Phe Asn Ile Asp Asp Leu Ser Ser Lys
835 840 845

Leu Asn Glu Ser Ile Asn Lys Ala Met Ile Asn Ile Asn Lys Phe Leu
850 855 860

Asn Gln Cys Ser Val Ser Tyr Leu Met Asn Ser Met Ile Pro Tyr Gly
865 870 875 880

Val Lys Arg Leu Glu Asp Phe Asp Ala Ser Leu Lys Asp Ala Leu Leu
885 890 895

Lys Tyr Ile Tyr Asp Asn Arg Gly Thr Leu Ile Gly Gln Val Asp Arg
900 905 910

Leu Lys Asp Lys Val Asn Asn Thr Leu Ser Thr Asp Ile Pro Phe Gln
915 920 925

Leu Ser Lys Tyr Val Asp Asn Gln Arg Leu Leu Ser Thr Leu Glu Ala
930 935 940

Leu Ala Ser Gly
945

<210> SEQ ID NO 70
<211> LENGTH: 930
<212> TYPE: PRT
<213> ORGANISM: Artificial Sequence
<220> FEATURE:
<223> OTHER INFORMATION: Protein sequence of LHD-EGFv2

<400> SEQUENCE: 70

Met Glu Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

-continued

```
Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Gly Gly Gly Ser Ala Asp Asp Asp Asp Lys Ser Arg Gly Ser Lys
        435                 440                 445

Cys Pro Pro Ser His Asp Gly Tyr Cys Leu Gln Gly Gly Val Cys Met
    450                 455                 460

Tyr Ile Glu Ala Leu Asp Arg Tyr Ala Cys Asn Cys Val Val Gly Tyr
465                 470                 475                 480

Ala Gly Glu Arg Cys Gln Tyr Arg Asp Leu Thr Trp Trp Gly Arg Arg
                485                 490                 495

Ala Leu Ala Gly Gly Gly Gly Ser Gly Gly Gly Gly Ser Gly Gly Gly
            500                 505                 510

Gly Ser Ala Leu Val Leu Gln Cys Ile Lys Val Asn Asn Trp Asp Leu
        515                 520                 525

Phe Phe Ser Pro Ser Glu Asp Asn Phe Thr Asn Asp Leu Asn Lys Gly
    530                 535                 540

Glu Glu Ile Thr Ser Asp Thr Asn Ile Glu Ala Ala Glu Glu Asn Ile
545                 550                 555                 560

Ser Leu Asp Leu Ile Gln Gln Tyr Tyr Leu Thr Phe Asn Phe Asp Asn
                565                 570                 575

Glu Pro Glu Asn Ile Ser Ile Glu Asn Leu Ser Ser Asp Ile Ile Gly
            580                 585                 590

Gln Leu Glu Leu Met Pro Asn Ile Glu Arg Phe Pro Asn Gly Lys Lys
        595                 600                 605

Tyr Glu Leu Asp Lys Tyr Thr Met Phe His Tyr Leu Arg Ala Gln Glu
    610                 615                 620
```

Phe Glu His Gly Lys Ser Arg Ile Ala Leu Thr Asn Ser Val Asn Glu
625 630 635 640

Ala Leu Leu Asn Pro Ser Arg Val Tyr Thr Phe Phe Ser Ser Asp Tyr
645 650 655

Val Lys Lys Val Asn Lys Ala Thr Glu Ala Ala Met Phe Leu Gly Trp
660 665 670

Val Glu Gln Leu Val Tyr Asp Phe Thr Asp Glu Thr Ser Glu Val Ser
675 680 685

Thr Thr Asp Lys Ile Ala Asp Ile Thr Ile Ile Ile Pro Tyr Ile Gly
690 695 700

Pro Ala Leu Asn Ile Gly Asn Met Leu Tyr Lys Asp Asp Phe Val Gly
705 710 715 720

Ala Leu Ile Phe Ser Gly Ala Val Ile Leu Leu Glu Phe Ile Pro Glu
725 730 735

Ile Ala Ile Pro Val Leu Gly Thr Phe Ala Leu Val Ser Tyr Ile Ala
740 745 750

Asn Lys Val Leu Thr Val Gln Thr Ile Asp Asn Ala Leu Ser Lys Arg
755 760 765

Asn Glu Lys Trp Asp Glu Val Tyr Lys Tyr Ile Val Thr Asn Trp Leu
770 775 780

Ala Lys Val Asn Thr Gln Ile Asp Leu Ile Arg Lys Lys Met Lys Glu
785 790 795 800

Ala Leu Glu Asn Gln Ala Glu Ala Thr Lys Ala Ile Ile Asn Tyr Gln
805 810 815

Tyr Asn Gln Tyr Thr Glu Glu Glu Lys Asn Asn Ile Asn Phe Asn Ile
820 825 830

Asp Asp Leu Ser Ser Lys Leu Asn Glu Ser Ile Asn Lys Ala Met Ile
835 840 845

Asn Ile Asn Lys Phe Leu Asn Gln Cys Ser Val Ser Tyr Leu Met Asn
850 855 860

Ser Met Ile Pro Tyr Gly Val Lys Arg Leu Glu Asp Phe Asp Ala Ser
865 870 875 880

Leu Lys Asp Ala Leu Leu Lys Tyr Ile Tyr Asp Asn Arg Gly Thr Leu
885 890 895

Ile Gly Gln Val Asp Arg Leu Lys Asp Lys Val Asn Asn Thr Leu Ser
900 905 910

Thr Asp Ile Pro Phe Gln Leu Ser Lys Tyr Val Asp Asn Gln Arg Leu
915 920 925

Leu Ser
930

<210> SEQ ID NO 71
<211> LENGTH: 925
<212> TYPE: PRT
<213> ORGANISM: Artificial Sequence
<220> FEATURE:
<223> OTHER INFORMATION: Protein sequence of LHC-CP-EGFv2

<400> SEQUENCE: 71

Met Pro Ile Thr Ile Asn Asn Phe Asn Tyr Ser Asp Pro Val Asp Asn
1 5 10 15

Lys Asn Ile Leu Tyr Leu Asp Thr His Leu Asn Thr Leu Ala Asn Glu
20 25 30

Pro Glu Lys Ala Phe Arg Ile Thr Gly Asn Ile Trp Val Ile Pro Asp
35 40 45

-continued

```
Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Ser Arg Gly
        435                 440                 445

Ser Lys Cys Pro Pro Ser His Asp Gly Tyr Cys Leu Gln Gly Gly Val
    450                 455                 460

Cys Met Tyr Ile Glu Ala Leu Asp Arg Tyr Ala Cys Asn Cys Val Val
465                 470                 475                 480
```

```
Gly Tyr Ala Gly Glu Arg Cys Gln Tyr Arg Asp Leu Thr Trp Trp Gly
                485                 490                 495

Arg Arg Ala Ala Leu Ala Gly Gly Gly Gly Ser Ala Leu Ala Leu Gln
            500                 505                 510

Cys Arg Glu Leu Leu Val Lys Asn Thr Asp Leu Pro Phe Ile Gly Asp
        515                 520                 525

Ile Ser Asp Val Lys Thr Asp Ile Phe Leu Arg Lys Asp Ile Asn Glu
    530                 535                 540

Glu Thr Glu Val Ile Tyr Tyr Pro Asp Asn Val Ser Val Asp Gln Val
545                 550                 555                 560

Ile Leu Ser Lys Asn Thr Ser Glu His Gly Gln Leu Asp Leu Leu Tyr
                565                 570                 575

Pro Ser Ile Asp Ser Glu Ser Glu Ile Leu Pro Gly Glu Asn Gln Val
            580                 585                 590

Phe Tyr Asp Asn Arg Thr Gln Asn Val Asp Tyr Leu Asn Ser Tyr Tyr
        595                 600                 605

Tyr Leu Glu Ser Gln Lys Leu Ser Asp Asn Val Glu Asp Phe Thr Phe
    610                 615                 620

Thr Arg Ser Ile Glu Glu Ala Leu Asp Asn Ser Ala Lys Val Tyr Thr
625                 630                 635                 640

Tyr Phe Pro Thr Leu Ala Asn Lys Val Asn Ala Gly Val Gln Gly Gly
                645                 650                 655

Leu Phe Leu Met Trp Ala Asn Asp Val Val Glu Asp Phe Thr Thr Asn
            660                 665                 670

Ile Leu Arg Lys Asp Thr Leu Asp Lys Ile Ser Asp Val Ser Ala Ile
        675                 680                 685

Ile Pro Tyr Ile Gly Pro Ala Leu Asn Ile Ser Asn Ser Val Arg Arg
    690                 695                 700

Gly Asn Phe Thr Glu Ala Phe Ala Val Thr Gly Val Thr Ile Leu Leu
705                 710                 715                 720

Glu Ala Phe Pro Glu Phe Thr Ile Pro Ala Leu Gly Ala Phe Val Ile
                725                 730                 735

Tyr Ser Lys Val Gln Glu Arg Asn Glu Ile Ile Lys Thr Ile Asp Asn
            740                 745                 750

Cys Leu Glu Gln Arg Ile Lys Arg Trp Lys Asp Ser Tyr Glu Trp Met
        755                 760                 765

Met Gly Thr Trp Leu Ser Arg Ile Ile Thr Gln Phe Asn Asn Ile Ser
    770                 775                 780

Tyr Gln Met Tyr Asp Ser Leu Asn Tyr Gln Ala Gly Ala Ile Lys Ala
785                 790                 795                 800

Lys Ile Asp Leu Glu Tyr Lys Lys Tyr Ser Gly Ser Asp Lys Glu Asn
                805                 810                 815

Ile Lys Ser Gln Val Glu Asn Leu Lys Asn Ser Leu Asp Val Lys Ile
            820                 825                 830

Ser Glu Ala Met Asn Asn Ile Asn Lys Phe Ile Arg Glu Cys Ser Val
        835                 840                 845

Thr Tyr Leu Phe Lys Asn Met Leu Pro Lys Val Ile Asp Glu Leu Asn
    850                 855                 860

Glu Phe Asp Arg Asn Thr Lys Ala Lys Leu Ile Asn Leu Ile Asp Ser
865                 870                 875                 880

His Asn Ile Ile Leu Val Gly Glu Val Asp Lys Leu Lys Ala Lys Val
                885                 890                 895

Asn Asn Ser Phe Gln Asn Thr Ile Pro Phe Asn Ile Phe Ser Tyr Thr
```

900 905 910

Asn Asn Ser Leu Leu Lys Asp Ile Ile Asn Glu Tyr Phe
915 920 925

<210> SEQ ID NO 72
<211> LENGTH: 925
<212> TYPE: PRT
<213> ORGANISM: Artificial Sequence
<220> FEATURE:
<223> OTHER INFORMATION: Protein sequence of LHC-EGFv3

<400> SEQUENCE: 72

Met Pro Ile Thr Ile Asn Asn Phe Asn Tyr Ser Asp Pro Val Asp Asn
1 5 10 15

Lys Asn Ile Leu Tyr Leu Asp Thr His Leu Asn Thr Leu Ala Asn Glu
20 25 30

Pro Glu Lys Ala Phe Arg Ile Thr Gly Asn Ile Trp Val Ile Pro Asp
35 40 45

Arg Phe Ser Arg Asn Ser Asn Pro Asn Leu Asn Lys Pro Pro Arg Val
50 55 60

Thr Ser Pro Lys Ser Gly Tyr Tyr Asp Pro Asn Tyr Leu Ser Thr Asp
65 70 75 80

Ser Asp Lys Asp Thr Phe Leu Lys Glu Ile Ile Lys Leu Phe Lys Arg
85 90 95

Ile Asn Ser Arg Glu Ile Gly Glu Glu Leu Ile Tyr Arg Leu Ser Thr
100 105 110

Asp Ile Pro Phe Pro Gly Asn Asn Asn Thr Pro Ile Asn Thr Phe Asp
115 120 125

Phe Asp Val Asp Phe Asn Ser Val Asp Val Lys Thr Arg Gln Gly Asn
130 135 140

Asn Trp Val Lys Thr Gly Ser Ile Asn Pro Ser Val Ile Ile Thr Gly
145 150 155 160

Pro Arg Glu Asn Ile Ile Asp Pro Glu Thr Ser Thr Phe Lys Leu Thr
165 170 175

Asn Asn Thr Phe Ala Ala Gln Glu Gly Phe Gly Ala Leu Ser Ile Ile
180 185 190

Ser Ile Ser Pro Arg Phe Met Leu Thr Tyr Ser Asn Ala Thr Asn Asp
195 200 205

Val Gly Glu Gly Arg Phe Ser Lys Ser Glu Phe Cys Met Asp Pro Ile
210 215 220

Leu Ile Leu Met His Glu Leu Asn His Ala Met His Asn Leu Tyr Gly
225 230 235 240

Ile Ala Ile Pro Asn Asp Gln Thr Ile Ser Ser Val Thr Ser Asn Ile
245 250 255

Phe Tyr Ser Gln Tyr Asn Val Lys Leu Glu Tyr Ala Glu Ile Tyr Ala
260 265 270

Phe Gly Gly Pro Thr Ile Asp Leu Ile Pro Lys Ser Ala Arg Lys Tyr
275 280 285

Phe Glu Glu Lys Ala Leu Asp Tyr Tyr Arg Ser Ile Ala Lys Arg Leu
290 295 300

Asn Ser Ile Thr Thr Ala Asn Pro Ser Ser Phe Asn Lys Tyr Ile Gly
305 310 315 320

Glu Tyr Lys Gln Lys Leu Ile Arg Lys Tyr Arg Phe Val Val Glu Ser
325 330 335

Ser Gly Glu Val Thr Val Asn Arg Asn Lys Phe Val Glu Leu Tyr Asn
340 345 350

```
Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Asp Lys Asn Ser Asp
        435                 440                 445

Pro Lys Cys Pro Leu Ser His Glu Gly Tyr Cys Leu Asn Asp Gly Val
    450                 455                 460

Cys Met Tyr Ile Gly Thr Leu Asp Arg Tyr Ala Cys Asn Cys Val Val
465                 470                 475                 480

Gly Tyr Val Gly Glu Arg Cys Gln Tyr Arg Asp Leu Lys Leu Ala Glu
                485                 490                 495

Leu Arg Ala Ala Leu Ala Gly Gly Gly Gly Ser Ala Leu Ala Leu Gln
            500                 505                 510

Cys Arg Glu Leu Leu Val Lys Asn Thr Asp Leu Pro Phe Ile Gly Asp
        515                 520                 525

Ile Ser Asp Val Lys Thr Asp Ile Phe Leu Arg Lys Asp Ile Asn Glu
    530                 535                 540

Glu Thr Glu Val Ile Tyr Tyr Pro Asp Asn Val Ser Val Asp Gln Val
545                 550                 555                 560

Ile Leu Ser Lys Asn Thr Ser Glu His Gly Gln Leu Asp Leu Leu Tyr
                565                 570                 575

Pro Ser Ile Asp Ser Glu Ser Glu Ile Leu Pro Gly Glu Asn Gln Val
            580                 585                 590

Phe Tyr Asp Asn Arg Thr Gln Asn Val Asp Tyr Leu Asn Ser Tyr Tyr
        595                 600                 605

Tyr Leu Glu Ser Gln Lys Leu Ser Asp Asn Val Glu Asp Phe Thr Phe
    610                 615                 620

Thr Arg Ser Ile Glu Glu Ala Leu Asp Asn Ser Ala Lys Val Tyr Thr
625                 630                 635                 640

Tyr Phe Pro Thr Leu Ala Asn Lys Val Asn Ala Gly Val Gln Gly Gly
                645                 650                 655

Leu Phe Leu Met Trp Ala Asn Asp Val Val Glu Asp Phe Thr Thr Asn
            660                 665                 670

Ile Leu Arg Lys Asp Thr Leu Asp Lys Ile Ser Asp Val Ser Ala Ile
        675                 680                 685

Ile Pro Tyr Ile Gly Pro Ala Leu Asn Ile Ser Asn Ser Val Arg Arg
    690                 695                 700

Gly Asn Phe Thr Glu Ala Phe Ala Val Thr Gly Val Thr Ile Leu Leu
705                 710                 715                 720

Glu Ala Phe Pro Glu Phe Thr Ile Pro Ala Leu Gly Ala Phe Val Ile
                725                 730                 735

Tyr Ser Lys Val Gln Glu Arg Asn Glu Ile Ile Lys Thr Ile Asp Asn
            740                 745                 750

Cys Leu Glu Gln Arg Ile Lys Arg Trp Lys Asp Ser Tyr Glu Trp Met
        755                 760                 765

Met Gly Thr Trp Leu Ser Arg Ile Ile Thr Gln Phe Asn Asn Ile Ser
```

```
    770                 775                 780

Tyr Gln Met Tyr Asp Ser Leu Asn Tyr Gln Ala Gly Ala Ile Lys Ala
785                 790                 795                 800

Lys Ile Asp Leu Glu Tyr Lys Lys Tyr Ser Gly Ser Asp Lys Glu Asn
                805                 810                 815

Ile Lys Ser Gln Val Glu Asn Leu Lys Asn Ser Leu Asp Val Lys Ile
            820                 825                 830

Ser Glu Ala Met Asn Asn Ile Asn Lys Phe Ile Arg Glu Cys Ser Val
        835                 840                 845

Thr Tyr Leu Phe Lys Asn Met Leu Pro Lys Val Ile Asp Glu Leu Asn
    850                 855                 860

Glu Phe Asp Arg Asn Thr Lys Ala Lys Leu Ile Asn Leu Ile Asp Ser
865                 870                 875                 880

His Asn Ile Ile Leu Val Gly Glu Val Asp Lys Leu Lys Ala Lys Val
                885                 890                 895

Asn Asn Ser Phe Gln Asn Thr Ile Pro Phe Asn Ile Phe Ser Tyr Thr
            900                 905                 910

Asn Asn Ser Leu Leu Lys Asp Ile Ile Asn Glu Tyr Phe
        915                 920                 925


<210> SEQ ID NO 73
<211> LENGTH: 159
<212> TYPE: PRT
<213> ORGANISM: Artificial Sequence
<220> FEATURE:
<223> OTHER INFORMATION: DNA sequence of a EGF variant targeting moiety
      v3

<400> SEQUENCE: 73

Ala Ala Thr Ala Gly Thr Gly Ala Cys Cys Cys Ala Ala Ala Gly Thr
1               5                   10                  15

Gly Thr Cys Cys Ala Thr Thr Ala Ala Gly Cys Cys Ala Thr Gly Ala
            20                  25                  30

Ala Gly Gly Ala Thr Ala Thr Thr Gly Thr Cys Thr Ala Ala Ala Cys
        35                  40                  45

Gly Ala Thr Gly Gly Thr Gly Thr Thr Thr Gly Thr Ala Thr Gly Thr
    50                  55                  60

Ala Cys Ala Thr Ala Gly Gly Gly Ala Cys Ala Thr Thr Gly Gly Ala
65                  70                  75                  80

Thr Ala Gly Gly Thr Ala Thr Gly Cys Thr Thr Gly Cys Ala Ala Thr
                85                  90                  95

Thr Gly Cys Gly Thr Ala Gly Thr Gly Gly Gly Ala Thr Ala Cys Gly
            100                 105                 110

Thr Ala Gly Gly Thr Gly Ala Ala Cys Gly Ala Thr Gly Cys Cys Ala
        115                 120                 125

Ala Thr Ala Thr Ala Gly Ala Gly Ala Cys Thr Thr Ala Ala Ala Ala
    130                 135                 140

Cys Thr Gly Gly Cys Ala Gly Ala Gly Cys Thr Thr Ala Gly Ala
145                 150                 155
```

NON-CYTOTOXIC FUSION PROTEINS COMPRISING EGF MUTEINS

Figure 1A:
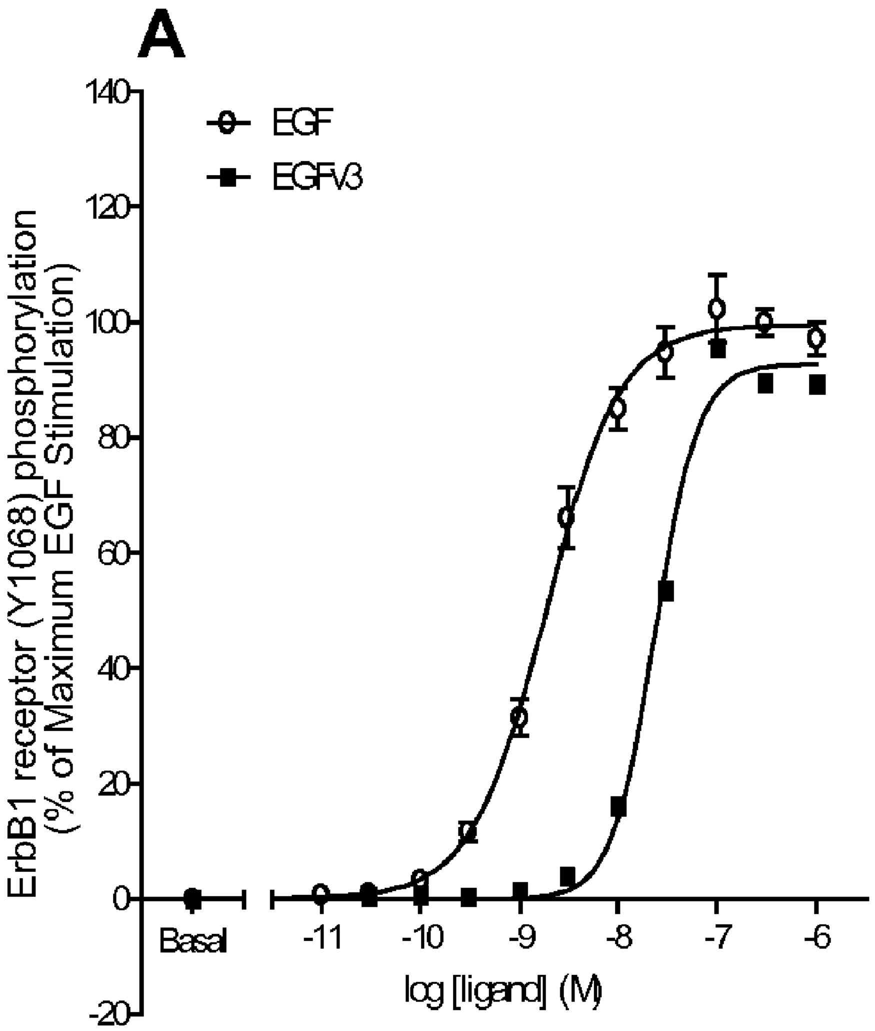
Figure 1B:
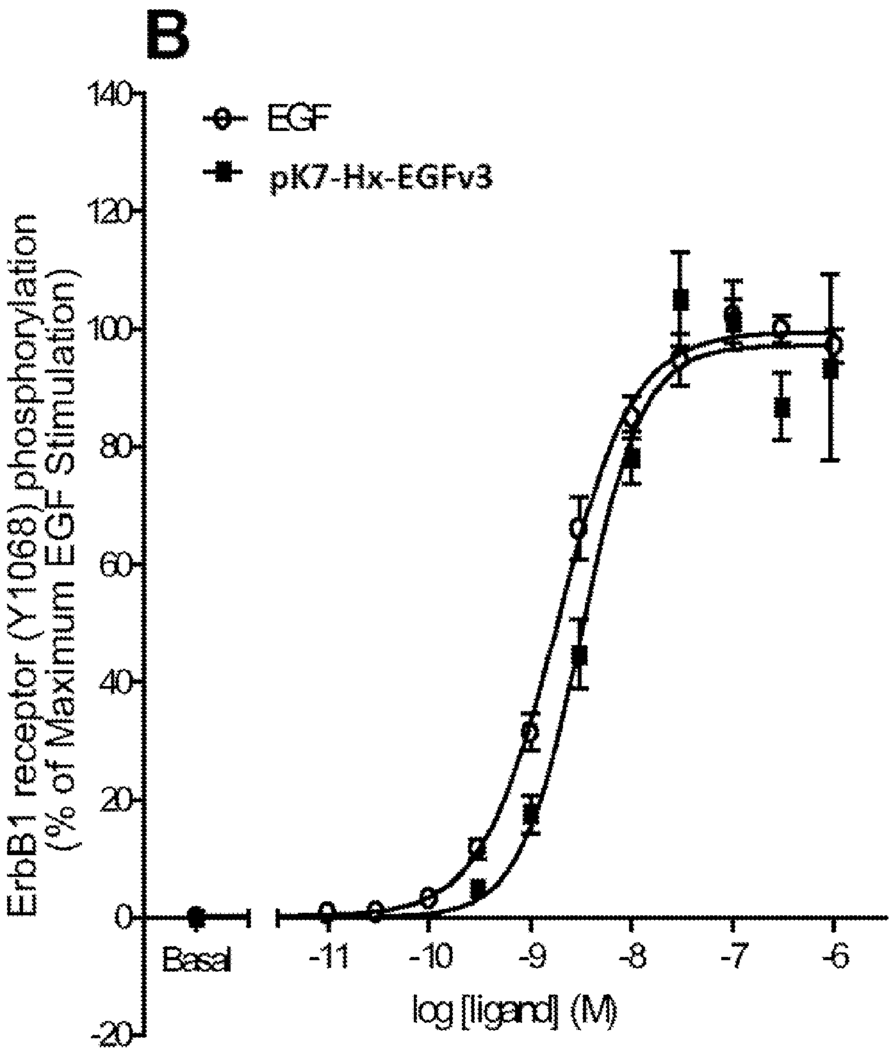
Figure 1C:
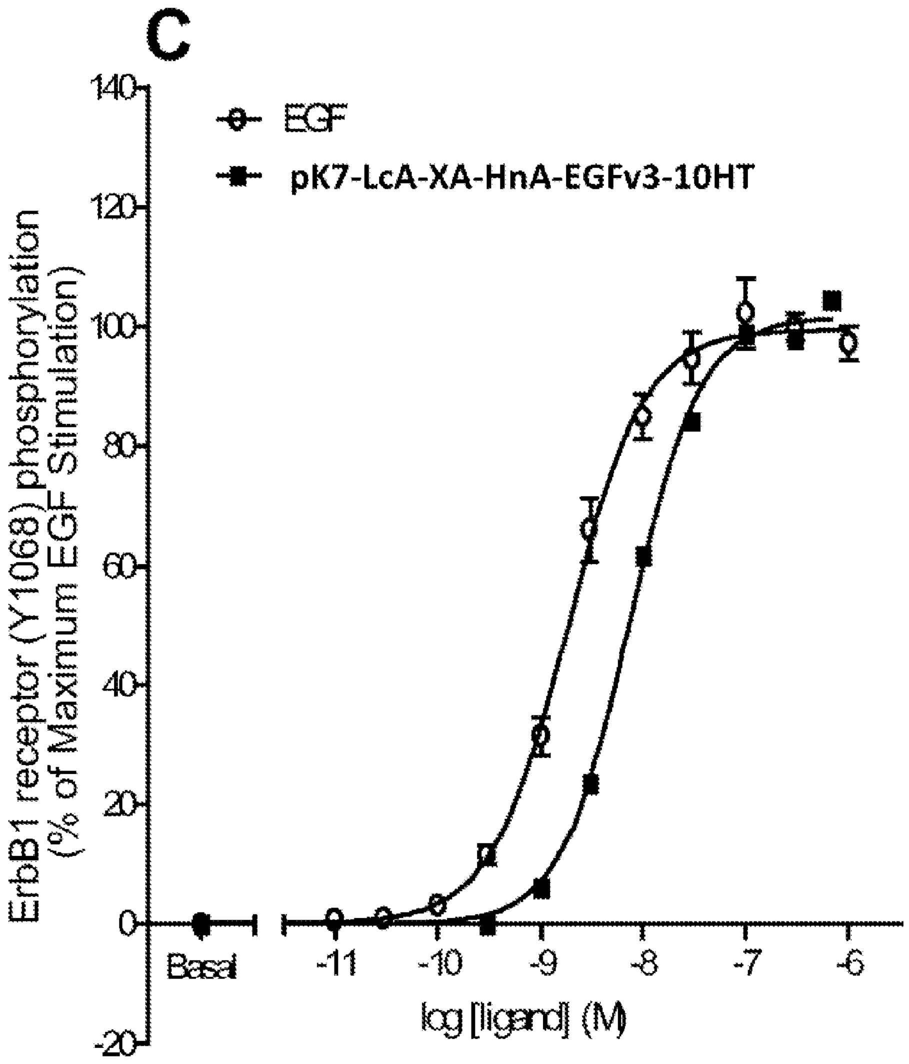
Figure 1D:
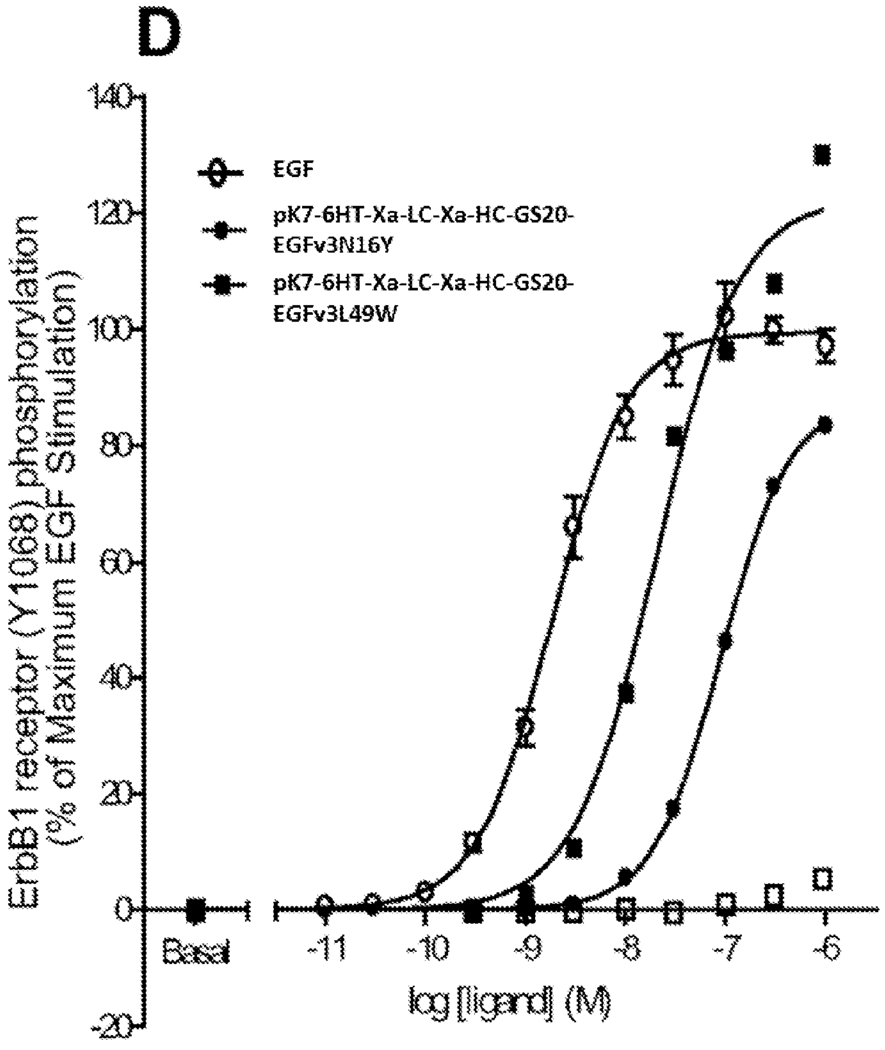

The present invention relates to non-cytotoxic fusion proteins, and to the use thereof as therapeutics for suppressing conditions such as mucus hypersecretion, inflammation, neuroendocrine disorders, and neuroendocrine tumours.

Non-cytotoxic proteases are a discrete group of proteases, which act on target cells by incapacitating cellular function. Importantly, non-cytotoxic proteases do not kill the target cells upon which they act. Some of the best known examples of non-cytotoxic proteases include clostridial neurotoxins and IgA proteases.

Non-cytotoxic proteases act by proteolytically-cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle formation, and thus to secretion of molecules via vesicle transport from a cell. Accordingly, once delivered to a desired target cell, the non-cytotoxic protease is capable of inhibiting cellular secretion from the target cell.

In view of the ubiquitous nature of SNARE proteins, non-cytotoxic proteases have been successfully employed in a wide range of therapies, such as: the treatment of pain (see WO96/33274); the treatment of mucus hypersecretion conditions such as COPD, asthma (see WO00/10598); the treatment of non-neuronal conditions such as endocrine conditions, exocrine conditions, immunological conditions, cardiovascular conditions, bone conditions (see WO01/21213); the treatment of neurological disorders such as Parkinson's disease (see U.S. Pat. No. 6,620,415, U.S. Pat. No. 6,306,403); the treatment of neuropsychiatric disorders (see US2004/0180061, US2003/0211121); the treatment of endocrine disorders (see U.S. Pat. No. 6,827,931); the treatment of thyroid disorders (see U.S. Pat. No. 6,740,321); the treatment of diabetes (see U.S. Pat. No. 6,337,075, U.S. Pat. No. 6,416,765); and the treatment of pancreatic disorders (see U.S. Pat. No. 6,261,572, U.S. Pat. No. 6,143,306). Each of the above publications is herein incorporated in its entirety by reference thereto.

Generally, administration of a non-cytotoxic protease is well tolerated. However, administration in some applications can be challenging because of the larger doses required to achieve a beneficial effect. Larger doses can increase the likelihood of undesirable antigenic responses. Similarly, larger doses are associated with increased manufacture costs.

In common with any other drug substances, a therapeutic dosing range exists which identifies the lower and upper limits of safe, effective therapy. Often, the upper limit is determined by the increasing significance of off-target effects that lead to undesirable (e.g. potentially harmful) side-effects of drug treatment. In the case of non-cytotoxic proteases, this could lead to the paralysis of cellular secretion in off-target cells, which, in turn, may be fatal.

The use of non-cytotoxic protease molecules in therapeutic treatments of humans and other mammals is attracting increasing interest. In this regard, one focused area of interest lies in the use of epidermal growth factor (EGF) re-targeted non-cytotoxic proteases. These therapeutics have been shown to be useful in reducing mucus secretion (see WO00/10598), and inflammation (see U.S. Ser. No. 11/806,648). The present inventors have also found that EGF re-targeted non-cytotoxic proteases are useful in suppressing neuroendocrine disorders, and neuroendocrine tumours.

However, one problem associated with the therapeutic application of EGF-based non-cytotoxic proteases is that efficacy may require the use of relatively high dosage levels. As mentioned above, this is undesirable for want of increased manufacture costs and/or potential immunogenicity problems.

Thus, there is a need in the art to develop means for reducing dosage sizes and/or for reducing undesirable antigenic responses, whilst maintaining the potency of the non-cytotoxic protease. This need is exacerbated by the growing use of non-cytotoxic proteases, which places an ever-increasing need on the part of the pharmaceutical industry to develop alternative and/or improved therapeutic molecules.

The present invention addresses the above need(s), and solves one or more of the above-mentioned problems. In more detail, the present invention provides alternative and/or improved EGF re-targeted non-cytotoxic proteases, which are useful for various clinical and therapeutic applications, in particular for treating inflammation, mucus secretion-related disorders such as asthma and COPD, as well as neuroendocrine disorders, and neuroendocrine tumours.

In more detail, a first aspect of the present invention provides a polypeptide, comprising:

a a non-cytotoxic protease that is capable of cleaving a SNARE protein;

b. a translocation peptide that is capable of translocating said non-cytotoxic protease from within an endosome of a mammalian cell, across the endosomal membrane thereof and into the cytosol of the mammalian cell; and c. an epidermal growth factor (EGF) mutein, wherein
   (i) said EGF mutein comprises an amino acid sequence having at least 65% sequence identity to the amino acid sequence of naturally-occurring human EGF (SEQ ID NO: 1), and wherein said EGF mutein amino acid sequence differs from the amino acid sequence of SEQ ID NO: 1 by at least one amino acid insertion, deletion or substitution at a position selected from amino acid positions 15-17 or 48-51 of SEQ ID NO: 1; and
   (ii) said EGF mutein amino acid sequence has an amino acid sequence backbone that retains all 6 cysteine amino acid residues as they appear at positions 6, 14, 20, 31, 33 and 42 in SEQ ID NO: 1.

Figure 2:
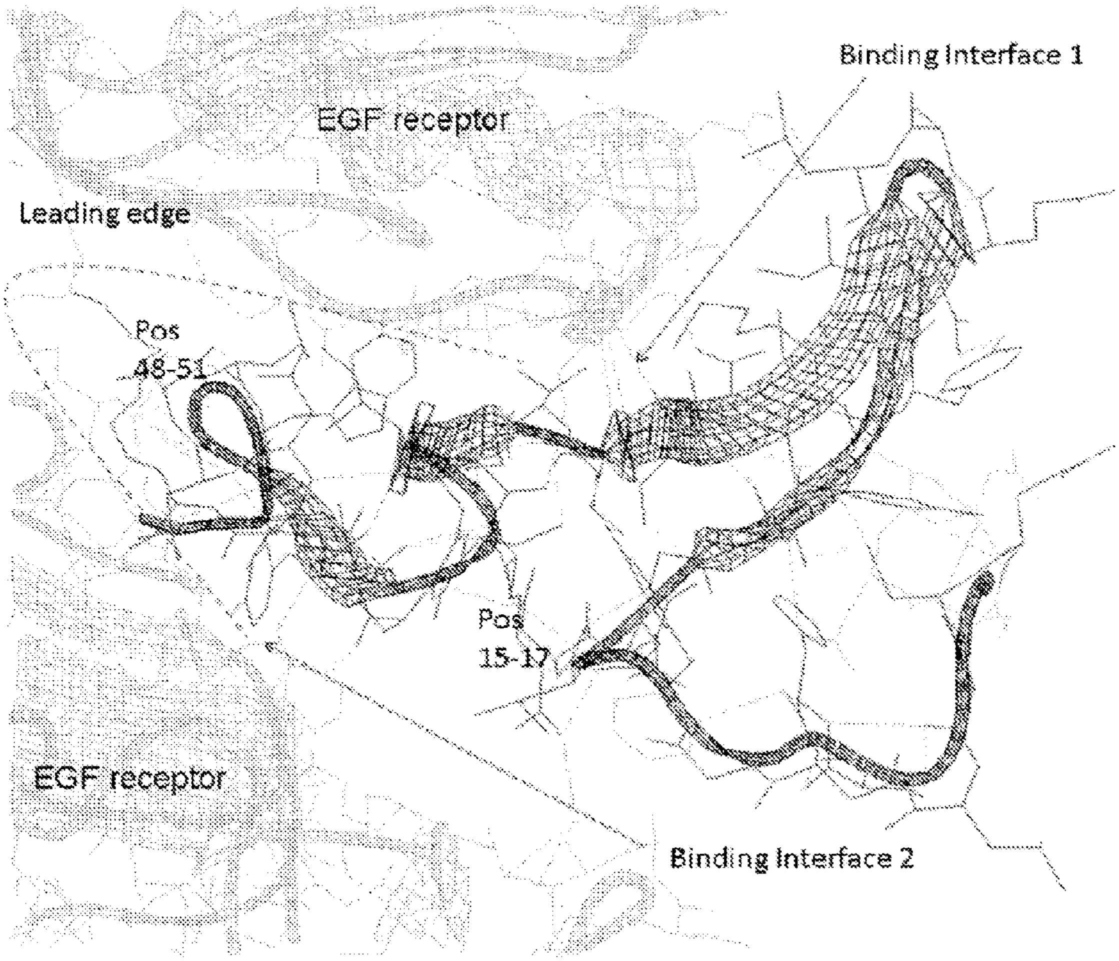

Without wishing to be bound by any theory, the present inventors believe that EGF binds to its natural receptor (ie. the EGF receptor; also known as $ErbB_1$) via a binding reaction, which involves two distinct binding interfaces present on the EGF molecule, namely a first binding interface (ie. Binding Interface 1) provided by the sequence of amino acid residues at positions 31-40 of SEQ ID NO: 1, and a second binding interface (ie. Binding Interface 2) provided the sequence of amino acid residues at positions 41-45 of SEQ ID NO: 1. These two Binding Interfaces are believed to bind to either side of a cleft, which is present in the EGF receptor, and into which a small portion (referred to as the Leading Edge) of the EGF molecule is then inserted. The Leading Edge is provided by the sequence of amino acid residues at positions 48-51 of SEQ ID NO: 1 and includes a scaffold support sequence provided by positions 15-17 of SEQ ID NO: 1. This binding arrangement is illustrated in FIG. 2, in which the U-shaped cleft of the receptor is positioned at the top and left-hand side of FIG. 2 and the 'open' face of the cleft points towards the centre of the FIG. 2.

In more detail, the present inventors believe that 'bulky' amino acid residues present within the Leading Edge (positions 15-17 and 48-51 of SEQ ID NO: 1) of EGF reduce the EGF receptor activation ability of EGF-based non-cytotoxic fusion molecules. Thus, by reducing the overall size of amino acid residues present within the Leading Edge, the present inventors have provided a new EGF mutein, which confers improved receptor activation properties on the EGF non-cytotoxic fusion molecules of the present invention when compared with corresponding wild-type EGF fusions.

In one embodiment, the EGF mutein is modified (compared with SEQ ID NO: 1) by substitution or deletion of one or more 'bulky' amino acid residues present in the Leading Edge, wherein said 'bulky' amino acid residues are selected from phenylalanine (F), tryptophan (W), or tyrosine (Y). By way of example, suitable substitutions may be selected from the group consisting of: leucine (L), isoleucine (I), valine (V), alanine (A), glycine (G), serine (S), threonine (T), asparagine (N), glutamine (Q), and methionine (M). In a preferred embodiment, said substitution or deletion is at positions 48-51, preferably at position 49 and/or position 50 (compared with SEQ ID NO: 1). In this regard, position 49 is preferably substituted (compared with SEQ ID NO: 1) to leucine (L), isoleucine (I) or valine (V), preferably to leucine (L); and/or position 50 is preferably substituted (compared with SEQ ID NO: 1) to alanine (A), glycine (G), serine (S), threonine (T) or methionine (M), preferably to alanine (A).

In one embodiment, the EGF mutein may be separately or further modified (compared with SEQ ID NO: 1) by substitution or deletion of one or more amino acid residues present at positions 15-17 of the Leading Edge. Modifications within this region are believed to increase the stability of the Leading Edge, for example by introduction of one or more additional inter- or intra-molecular hydrogen bonds. By way of example, suitable substitutions may be selected from the group consisting of: asparagine (N), glutamine (Q), aspartate (D), cysteine (C), glycine (G), leucine (L), serine (S), threonine (T), valine (V), tryptophan (W), and tyrosine (Y). In this regard, position 16 is preferably substituted (compared with SEQ ID NO: 1) to asparagine (N) or glutamine (Q).

In addition to the above-described Leading Edge modifications, the EGF mutein may be further modified (compared with SEQ ID NO: 1) by substitution or deletion of one or more amino acid residues present at positions 23-29. These positions are close to the Binding Interface 1 (discussed above), and help provide additional stability to the EGF mutein. By way of example, suitable substitutions may be selected from the group consisting of: glycine (G), alanine (A), serine (S), threonine (T), methionine (M), arginine (R), lysine (K), and histidine (H). In this regard, preferred substitutions are introduced at one or more of positions 24-28. For example, position 24 is preferably substituted (compared with SEQ ID NO: 1) to glycine (G), alanine (A), serine (S), threonine (T) or methionine (M), preferably to glycine (G); and/or position 25 is preferably substituted (compared with SEQ ID NO: 1) to threonine (T), glycine (G), alanine (A), serine (S), or methionine (M), preferably to threonine (T); and/or position 28 is preferably substituted (compared with SEQ ID NO: 1) to arginine (R), lysine (K) or histidine (H), preferably to arginine (R).

In addition to the above-described Leading Edge modifications, and optionally in addition to the above-described modification at position 23-29, the EGF mutein may be further modified (compared with SEQ ID NO: 1) by substitution or deletion of one or more amino acid residues present at positions 3-5. These positions are close to where the EGF mutein is typically fused to the larger body of the fusion protein, and help provide additional stability to the EGF mutein. By way of example, suitable substitutions may be selected from the group consisting of: proline (P), arginine (R), lysine (K), and histidine (H). In this regard, position 4 is preferably substituted (compared with SEQ ID NO: 1) to proline (P), and/or position 5 is preferably substituted (compared with SEQ ID NO: 1) to arginine (R), lysine (K) or histidine (H), preferably lysine (K).

In addition to the above-described Leading Edge modifications, and optionally in addition to the above-described modification at position 23-29 and/or positions 3-5, the EGF mutein may be further modified (compared with SEQ ID NO: 1) by substitution or deletion of one or more amino acid residues present at positions 10-12. These positions are close to where the EGF mutein is typically fused to the larger body of the fusion protein, and help provide additional stability to the EGF mutein. By way of example, suitable substitutions may be selected from the group consisting of: glutamic acid (E) and aspartic acid (D). In this regard, position 11 is preferably substituted (compared with SEQ ID NO: 1) to glutamic acid (E) or aspartic acid (D), preferably to glutamic acid.

In addition to the above-described Leading Edge modifications, and optionally in addition to the above-described modification at position 23-29 and/or positions 3-5 and/or positions 10-12, the EGF mutein may be further modified (compared with SEQ ID NO: 1) by substitution or deletion of one or more amino acid residues present at positions 37-39. These positions are close to both the Binding Interface 1 and Binding Interface 2 (discussed above), and help provide additional stability to the EGF mutein. By way of example, suitable substitutions may be selected from the group consisting of: valine (V), leucine (L), and isoleucine (I). In this regard, position 38 is preferably substituted (compared with SEQ ID NO: 1) to valine (V), leucine (L) or isoleucine (I), preferably to valine (V).

The present inventors have noted that the activation ability of an EGF molecule (for its natural EGF receptor) is significantly reduced when the EGF molecule is present as part of a much larger fusion protein, as is the case when such a molecule is used as a Targeting Moiety in a non-cytotoxic fusion protein. This problem is addressed by the present invention by the introduction of one or more mutations, which increase the activation ability of said EGF molecule when it is present as part of a larger non-cytotoxic fusion protein. This, in turn, improves the cell targeting efficiency of the polypeptides of the present invention, and means that lower dosage regimens may be employed. The latter reduces manufacturing costs, and minimises undesirable, patient-related antigenic effects against the polypeptides of the invention.

It is routine to confirm that an EGF mutein of the present invention has improved activation ability for an EGF (eg. ErbB) receptor—by way of example, we refer to Examples 4 & 5.

In one embodiment, the EGF fusions of the present invention demonstrate a binding affinity to an EGF receptor (e.g. $ErbB_1$) that is greater than 4 or 2 nM, or greater than 0.4 or 0.2 nM, or greater than 0.04 or 0.02 nM.

In another embodiment, the EGF fusions of the present invention demonstrate a binding activation of an EGF receptor (e.g. $ErbB_1$) that is greater than 6 $pEC_{50}$, or greater than 7 $pEC_{50}$, or greater than 8 $pEC_{50}$. Examples of suitable assays are provided in Examples 9 & 10.

The EGF mutein comprises at least one amino acid deletion, substitution or insertion vis-6-vis naturally-occurring human EGF (SEQ ID NO: 1), though with the proviso that none of the 6 cysteine amino acid residues of naturally-occurring human EGF is so altered. In a preferred embodiment, the EGF mutein comprises at least 2, 3, 4, 5, 6, 7, 8, 9, 10, 11, 12, 13, 14 or 15 such deletions, substitutions or insertions. Of said modifications, substitutions are the most preferred, as they have less effect on secondary or tertiary structure. In the case of deletions or insertions, the EGF mutein preferably has at most 4 or 5, more preferably at most 2 or 3, and particularly preferably at most 1 such deletion and/or insertion.

In one embodiment, the EGF mutein comprises no more than 15, 14 or 13, preferably no more than 12, 11 or 10 amino acid deletions, substitutions or insertions vis-à-vis naturally-occurring human EGF (SEQ ID NO: 1). Of said modifications, substitutions are the most preferred, as they have less effect on secondary or tertiary structure. In the case of deletions or insertions, the EGF mutein preferably has at most 4 or 5, more preferably at most 2 or 3, and particularly preferably at most 1 such deletion and/or insertion.

In one embodiment, the EGF mutein comprises (or consists of) at least 37 amino acid residues. For example, an EGF mutein comprising this length has a primary amino acid sequence that closely mimics the 6 cysteine consensus sequence backbone of naturally-occurring hEGF (eg. SEQ ID NO:1). Such a 37 amino acid sequence is characterised by cysteine residues at positions (in an N-terminal to C-terminal direction) 1, 9, 15, 26, 28 and 37. In another embodiment (preferably including the above-defined backbone sequence), the EGF mutein comprises at least 39 or 41, preferably at least 43 or 45, more preferably at least 47 or 49 contiguous amino acid residues. In another embodiment, the EGF mutein comprises at least 51, 52 or 53 amino acid residues.

In one embodiment, the EGF mutein differs from naturally-occurring human EGF in that it comprises at least one (or more, as detailed above) deletion, substitution or insertion at any of the positions: $D_3S_4E_5$, $P_7L_8S_9$, $G_{12}Y_{13}$, $L_{15}H_{16}$, $M_{21}Y_{22}I_{23}E_{24}A_{25}$, $I_{38}G_{39}E_{40}R_{41}$, $Q_{43}Y_{44}R_{45}D_{46}L_{47}K_{48}W_{49}W_{50}E_{51}L_{52}$ (positions and letters refer to the one-letter amino acid code of naturally-occurring human EGF—SEQ ID NO:1).

For example: $D_3$ can be substituted with G, N, Y, A or F; $S_4$ can be substituted with T, P, F, Q or R; $E_5$ can be substituted with G, K, or Q, $P_7$ can be substituted with S, $L_8$ can be substituted with P, S, R or Q; $S_9$ can be substituted by P; $G_{12}$ can be substituted with E, D, or Q; $Y_{13}$ can be substituted with H or W; $L_{15}$ can be substituted by A, I, M, F or V; $H_{16}$ can be substituted with Q, N, A, E, D or Y, $M_{21}$ can be substituted with V, R, or K; $Y_{22}$ can be substituted with H, $I_{23}$ can be substituted with V or L; $E_{24}$ can be substituted with K, G or V; $A_{25}$ can be substituted with S, T, or Q; $I_{38}$ can be substituted with T, S, A, N, L, or V; $G_{39}$ can be substituted with E, Q, K, D, I, L, or F; $E_{40}$ can be substituted with D; $R_{41}$ can be substituted by D; $Q_{43}$ can be substituted with E; $Y_{44}$ can be substituted with H or T; $R_{45}$ can be substituted by G, Q, or P; $R_{46}$ can be substituted by G; $L_{47}$ can be substituted by G, D, or R; $K_{48}$ can be substituted with R, T, or D; $W_{49}$ can be substituted by R; $W_{50}$ can be substituted by L; $E_{51}$ can be substituted by G, A, W, K, or Y; and/or $L_{52}$ can be substituted by P, R, or T.

In addition or separately, $Q_{18}$ can be substituted with E, Q, K, F or L; and/or $V_{35}$ can be substituted with E; D17 can be substituted by G; V19 can be substituted by A.

In addition or separately, $N_1$ can be substituted by S, K, Y, T or H; $S_2$ can be substituted by G or R; $E_5$ can be substituted by G or K; $H_{10}$ can be substituted by Y; $D_{11}$ can be substituted by N, S, or E; $L_{26}$ can be substituted by V; $K_{28}$ can be substituted by R, S, or T; $A_{30}$ can be substituted by V; $N_{32}$ can be substituted by S; $V_{34}$ can be substituted by A; $V_{35}$ can be substituted by A.

In one embodiment, the EGF mutein differs from naturally-occurring human EGF in that it comprises at least one (or more, as detailed above) deletion, substitution or insertion at any of the positions $G_{12}Y_{13}$, $H_{16}$ (positions and letters refer to the one-letter amino acid code of naturally-occurring human EGF—SEQ ID NO:1). By way of example, $G_{12}$ may be substituted by an amino acid residue such as glutamine (Q) or asparagine (N). Similarly, $Y_{13}$ may be substituted by a residue such as tryptophan (W) or phenylalanine (F), and $H_{16}$ may be substituted by a residue such as aspartic acid (D), glutamic acid (E), glycine (G), alanine (A), serine (S), or threonine (T).

In one embodiment, the EGF mutein comprises an amino acid sequence as set forth in any of SEQ ID NOs: 6-32, 34, 36, 38, 40, 42, 44, 46, 49, 50, 52, 54, 56, 58, and 60. This embodiment embraces variants thereof having at least 80%, at least 85%, at least 90%, at least 95%, or at least 97% sequence identity thereto, though with the proviso that said variants always retain the specific amino acid substitution(s) illustrated in said SEQ ID NOs when compared with wild-type human EGF (ie. SEQ ID NO: 1). This embodiment also embraces variants thereof having at least 80%, at least 85%, at least 90%, at least 95%, or at least 97% sequence identity thereto, though with the proviso that said variants always retain a conservative amino acid substitution of the specific amino acid substitution(s) illustrated in said SEQ ID NOs when compared with wild-type human EGF (ie. SEQ ID NO: 1).

The biologically active component of the polypeptides of the present invention is a non-cytotoxic protease. Non-cytotoxic proteases are produced by a variety of plants, and by a variety of microorganisms such as clostridial sp. and neisserial sp. (e.g. *N. gonorrhoeae*).

In a preferred embodiment, the non-cytotoxic protease of the present invention is a clostridial neurotoxin protease or a neisserial IgA protease.

Turning now to the translocation peptide (also referred to as the translocation domain) of the present invention, this component serves to translocate the non-cytotoxic protease across the endosomal membrane and into the cytosol of a target cell, where the protease component may then exert its proteolytic effect on SNARE proteins. Translocation peptides are well known in the art, and are produced by a variety of plants and microorganisms.

In a preferred embodiment, the translocation peptide of the present invention is a clostridial neurotoxin translocation peptide (also known as a clostridial translocation domain, or $H_N$).

The polypeptide of the present invention comprises a modified EGF molecule, which acts as a Targeting Moiety (TM) to direct the polypeptide to a selected target cell(s), for example by binding to an EGF receptor on a mucus-secreting cell. In a preferred embodiment, the EGF receptor is an ErbB receptor, preferably an $ErbB_1$ receptor.

According to a second aspect of the present invention, there is provided a non-cytotoxic polypeptide (as defined above), for use in treating a range of medical conditions and diseases.

In one embodiment, the present invention provides use of said non-cytotoxic polypeptides and corresponding methods for the suppression of mucus hypersecretion, in particular conditions or diseases in which mucus hypersecretion is a causative element, such as (chronic) bronchitis, chronic obstructive pulmonary disease (COPD), and asthma.

In one embodiment, the present invention provides use and corresponding methods for the suppression of inflammation.

In another embodiment, the present invention provides use and corresponding methods for the suppression of endocrine neoplasia such as MEN, thyrotoxicosis and neuroendocrine disorders such as Cushing's disease, acromegaly, hyperandrogenism, chronic anovulation, polycystic ovarian syndrome, carcinoid syndrome, hypoglycaemic syndrome, necrolytic migratory erythema, Zollinger-Ellison syndrome, and Verner-Morrison syndrome.

In one embodiment, the present invention provides use and corresponding methods for the suppression of neuroendocrine tumours such as non-carcinoid gastroenteropancreatic neuroendocrine tumours, carcinoid tumours, pituitary tumours and phaeochromocytomas, and for suppressing cancers such as colorectal cancer, prostate cancer, breast cancer, and lung cancer.

In use, a polypeptide of the invention binds to an EGF (eg. ErbB) receptor (the Binding Site), which is present on and preferably characteristic of a target cell. Thus, in the context of mucus applications, the EGF TM binds to mucus-secreting cells (e.g. epithelial goblet cells, or submucosal gland mucus-secreting cells). In the context of anti-inflammatory applications, the EGF TM binds to inflammatory leukocyte cells (e.g. neutrophils). In the context of neuroendocrine conditions, the EGF TM may bind to a tumour cell itself, or to a growth hormone-secreting cell (eg. a pituitary cell). Following binding, the polypeptide of the invention (at least the non-cytotoxic protease component thereof) becomes endocytosed into a vesicle, and the translocation component then directs transport of the non-cytotoxic protease across the endosomal membrane and into the cytosol of the target cell. Once inside the target cell, the non-cytotoxic protease component inhibits the cellular exocytic fusion process, and thereby inhibits release/secretion from the target cell.

Polypeptide Preparation

The polypeptides of the present invention comprise 3 principal components: a 'warhead' (ie. a non-cytotoxic protease); an EGF mutein TM; and a translocation domain. The general technology associated with the preparation of such fusion proteins is often referred to as re-targeted toxin technology. By way of exemplification, we refer to: WO94/21300; WO96/33273; WO98/07864; WO00/10598; WO01/21213; WO06/059093; WO00/62814; WO00/04926; WO93/15766; WO00/61192; and WO99/58571. All of these publications are herein incorporated by reference thereto.

In more detail, the TM component of the present invention may be fused to either the protease component or the translocation component of the present invention. Said fusion is preferably by way of a covalent bond, for example either a direct covalent bond or via a spacer/linker molecule. The protease component and the translocation component are preferably linked together via a covalent bond, for example either a direct covalent bond or via a spacer/linker molecule. Suitable spacer/linked molecules are well known in the art, and typically comprise an amino acid-based sequence of between 5 and 40, preferably between 10 and 30 amino acid residues in length.

In use, the polypeptides have a di-chain conformation, wherein the protease component and the translocation component are linked together, preferably via a disulphide bond.

The polypeptides of the present invention may be prepared by conventional chemical conjugation techniques, which are well known to a skilled person. By way of example, reference is made to Hermanson, G. T. (1996), Bioconjugate techniques, Academic Press, and to Wong, S. S. (1991), Chemistry of protein conjugation and cross-linking, CRC Press.

Alternatively, the polypeptides may be prepared by recombinant preparation of a single polypeptide fusion protein (see, for example, WO98/07864). This technique is based on the in vivo bacterial mechanism by which native clostridial neurotoxin (ie. holotoxin) is prepared, and results in a fusion protein having the following 'simplified' structural arrangement:

$NH_2$-[protease component]-[translocation component]-[EGF TM]-COOH

According to WO98/07864, the TM is placed towards the C-terminal end of the fusion protein. The fusion protein is then activated by treatment with a protease, which cleaves at a site between the protease component and the translocation component. A di-chain protein is thus produced, comprising the protease component as a single polypeptide chain covalently attached (via a disulphide bridge) to another single polypeptide chain containing the translocation component plus TM.

Alternatively, the fusion proteins of the present invention may be prepared according to WO06/05093 such that the TM has an N-terminal domain that is 'free' for interaction with a Binding Site on a target cell. In this system, the TM component of the fusion protein is located towards the middle of the linear fusion protein sequence, between the protease cleavage site and the translocation component. Subsequent cleavage at the protease cleavage site exposes the N-terminal portion of the TM, and provides the di-chain polypeptide fusion protein.

The above-mentioned protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.). Whilst any protease cleavage site may be employed (ie. clostridial, or non-clostridial), the following are preferred:

| | |
|---|---|
| Enterokinase (DDDDK↓) | (SEQ I D NO: 74) |
| Factor Xa (IEGR↓/IDGR↓) | (SEQ I D NO: 75/76) |
| TEV(Tobacco Etch virus) (ENLYFQ↓G) | (SEQ I D NO: 77) |
| Thrombin (LVPR↓GS) | (SEQ I D NO: 78) |
| PreScission (LEVLFQ↓GP) | (SEQ I D NO: 79) |
| CleanCut (WELQ↓X) | (SEQ I D NO: 80) |

(X indicates any amino acid excluding proline)

Also embraced by the term protease cleavage site is an intein, which is a self-cleaving sequence. The self-splicing reaction is controllable, for example by varying the concentration of reducing agent present. The above-mentioned 'activation' cleavage sites may also be employed as a 'destructive' cleavage site (discussed below) should one be incorporated into a polypeptide of the present invention.

In a preferred embodiment, the fusion protein of the present invention may comprise one or more N-terminal and/or C-terminal located purification tags. Whilst any purification tag may be employed, the following are preferred:

His-tag (e.g. 6× histidine), preferably as a C-terminal and/or N-terminal tag

MBP-tag (maltose binding protein), preferably as an N-terminal tag

GST-tag (glutathione-S-transferase), preferably as an N-terminal tag

His-MBP-tag, preferably as an N-terminal tag

GST-MBP-tag, preferably as an N-terminal tag

Thioredoxin-tag, preferably as an N-terminal tag

CBD-tag (Chitin Binding Domain), preferably as an N-terminal tag.

One or more peptide spacer/linker molecules may be included in the fusion protein. For example, a peptide spacer may be employed between a purification tag and the rest of the fusion protein molecule.

Thus, a third aspect of the present invention provides a nucleic acid (e.g. DNA) sequence encoding a polypeptide as described above.

Said nucleic acid may be included in the form of a vector, such as a plasmid, which may optionally include one or more of an origin of replication, a nucleic acid integration site, a promoter, a terminator, and a ribosome binding site.

The present invention also includes a method for expressing the above-described nucleic acid sequence (i.e. the third aspect of the present invention) in a host cell, in particular in *E. coli*.

The present invention also includes a method for activating a polypeptide of the present invention, said method comprising contacting the polypeptide with a protease that cleaves the polypeptide at a recognition site (cleavage site) located between the non-cytotoxic protease component and the translocation component, thereby converting the polypeptide into a di-chain polypeptide wherein the non-cytotoxic protease and translocation components are joined together by a disulphide bond. In a preferred embodiment, the recognition site is not native to a naturally-occurring clostridial neurotoxin and/or to a naturally-occurring IgA protease.

The polypeptides of the present invention may be further modified to reduce or prevent unwanted side-effects associated with dispersal into non-targeted areas. According to this embodiment, the polypeptide comprises a destructive cleavage site. The destructive cleavage site is distinct from the 'activation' site (i.e. di-chain formation), and is cleavable by a second protease and not by the non-cytotoxic protease. Moreover, when so cleaved at the destructive cleavage site by the second protease, the polypeptide has reduced potency (e.g. reduced binding ability to the intended target cell, reduced translocation activity and/or reduced non-cytotoxic protease activity). For completeness, any of the 'destructive' cleavage sites of the present invention may be separately employed as an 'activation' site in a polypeptide of the present invention.

Thus, according to this embodiment, the present invention provides a polypeptide that can be controllably inactivated and/or destroyed at an off-site location.

In a preferred embodiment, the destructive cleavage site is recognised and cleaved by a second protease (i.e. a destructive protease) selected from a circulating protease (e.g. an extracellular protease, such as a serum protease or a protease of the blood clotting cascade), a tissue-associated protease (e.g. a matrix metalloprotease (MMP), such as an MMP of muscle), and an intracellular protease (preferably a protease that is absent from the target cell.

Thus, in use, should a polypeptide of the present invention become dispersed away from its intended target cell and/or be taken up by a non-target cell, the polypeptide will become inactivated by cleavage of the destructive cleavage site (by the second protease).

In one embodiment, the destructive cleavage site is recognised and cleaved by a second protease that is present within an off-site cell-type. In this embodiment, the off-site cell and the target cell are preferably different cell types. Alternatively (or in addition), the destructive cleavage site is recognised and cleaved by a second protease that is present at an off-site location (e.g. distal to the target cell). Accordingly, when destructive cleavage occurs extracellularly, the target cell and the off-site cell may be either the same or different cell-types. In this regard, the target cell and the off-site cell may each possess a receptor to which the same polypeptide of the invention binds.

The destructive cleavage site of the present invention provides for inactivation/destruction of the polypeptide when the polypeptide is in or at an off-site location. In this regard, cleavage at the destructive cleavage site minimises the potency of the polypeptide (when compared with an identical polypeptide lacking the same destructive cleavage site, or possessing the same destructive site but in an uncleaved form). By way of example, reduced potency includes: reduced binding (to a mammalian cell receptor) and/or reduced translocation (across the endosomal membrane of a mammalian cell in the direction of the cytosol), and/or reduced SNARE protein cleavage.

When selecting destructive cleavage site(s) in the context of the present invention, it is preferred that the destructive cleavage site(s) are not substrates for any proteases that may be separately used for post-translational modification of the polypeptide of the present invention as part of its manufacturing process. In this regard, the non-cytotoxic proteases of the present invention typically employ a protease activation event (via a separate 'activation' protease cleavage site, which is structurally distinct from the destructive cleavage site of the present invention). The purpose of the activation cleavage site is to cleave a peptide bond between the non-cytotoxic protease and the translocation or the binding components of the polypeptide of the present invention, thereby providing an 'activated' di-chain polypeptide wherein said two components are linked together via a di-sulfide bond.

Thus, to help ensure that the destructive cleavage site(s) of the polypeptides of the present invention do not adversely affect the 'activation' cleavage site and subsequent di-sulfide bond formation, the former are preferably introduced into polypeptide of the present invention at a position of at least 20, at least 30, at least 40, at least 50, and more preferably at least 60, at least 70, at least 80 (contiguous) amino acid residues away from the 'activation' cleavage site.

The destructive cleavage site(s) and the activation cleavage site are preferably exogenous (i.e. engineered/artificial) with regard to the native components of the polypeptide. In other words, said cleavage sites are preferably not inherent to the corresponding native components of the polypeptide. By way of example, a protease or translocation component based on BoNT/A L-chain or H-chain (respectively) may be engineered according to the present invention to include a cleavage site. Said cleavage site would not, however, be present in the corresponding BoNT native L-chain or H-chain. Similarly, when the Targeting Moiety component of the polypeptide is engineered to include a protease cleavage site, said cleavage site would not be present in the corresponding native sequence of the corresponding Targeting Moiety.

In a preferred embodiment of the present invention, the destructive cleavage site(s) and the 'activation' cleavage site are not cleaved by the same protease. In one embodiment, the two cleavage sites differ from one another in that at least one, more preferably at least two, particularly preferably at least three, and most preferably at least four of the tolerated amino acids within the respective recognition sequences is/are different.

By way of example, in the case of a polypeptide chimaera containing a Factor Xa 'activation' site between clostridial L-chain and $H_N$ components, it is preferred to employ a destructive cleavage site that is a site other than a Factor Xa site, which may be inserted elsewhere in the L-chain and/or $H_N$ and/or TM component(s). In this scenario, the polypeptide may be modified to accommodate an alternative 'activation' site between the L-chain and $H_N$ components (for example, an enterokinase cleavage site), in which case a separate Factor Xa cleavage site may be incorporated elsewhere into the polypeptide as the destructive cleavage site. Alternatively, the existing Factor Xa 'activation' site between the L-chain and $H_N$ components may be retained, and an alternative cleavage site such as a thrombin cleavage site incorporated as the destructive cleavage site.

When identifying suitable sites within the primary sequence of any of the components of the present invention for inclusion of cleavage site(s), it is preferable to select a primary sequence that closely matches with the proposed cleavage site that is to be inserted. By doing so, minimal structural changes are introduced into the polypeptide. By way of example, cleavage sites typically comprise at least 3 contiguous amino acid residues. Thus, in a preferred embodiment, a cleavage site is selected that already possesses (in the correct position(s)) at least one, preferably at least two of the amino acid residues that are required in order to introduce the new cleavage site. By way of example, in one embodiment, the Caspase 3 cleavage site (DMQD) may be introduced. In this regard, a preferred insertion position is identified that already includes a primary sequence selected from, for example, Dxxx, xMxx, xxQx, xxxD, DMxx, DxQx, DxxD, xMQx, xMxD, xxQD, DMQx, xMQD, DxQD, and DMxD.

Similarly, it is preferred to introduce the cleavage sites into surface exposed regions. Within surface exposed regions, existing loop regions are preferred.

In a preferred embodiment of the present invention, the destructive cleavage site(s) are introduced at one or more of the following position(s), which are based on the primary amino acid sequence of BoNT/A. Whilst the insertion positions are identified (for convenience) by reference to BoNT/A, the primary amino acid sequences of alternative protease domains and/or translocation domains may be readily aligned with said BoNT/A positions.

For the protease component, one or more of the following positions is preferred: 27-31, 56-63, 73-75, 78-81, 99-105, 120-124, 137-144, 161-165, 169-173, 187-194, 202-214, 237-241, 243-250, 300-304, 323-335, 375-382, 391-400, and 413-423. The above numbering preferably starts from the N-terminus of the protease component of the present invention.

In a preferred embodiment, the destructive cleavage site(s) are located at a position greater than 8 amino acid residues, preferably greater than 10 amino acid residues, more preferably greater than 25 amino acid residues, particularly preferably greater than 50 amino acid residues from the N-terminus of the protease component. Similarly, in a preferred embodiment, the destructive cleavage site(s) are located at a position greater than 20 amino acid residues, preferably greater than 30 amino acid residues, more preferably greater than 40 amino acid residues, particularly preferably greater than 50 amino acid residues from the C-terminus of the protease component.

For the translocation component, one or more of the following positions is preferred: 474-479, 483-495, 507-543, 557-567, 576-580, 618-631, 643-650, 669-677, 751-767, 823-834, 845-859. The above numbering preferably acknowledges a starting position of 449 for the N-terminus of the translocation domain component of the present invention, and an ending position of 871 for the C-terminus of the translocation domain component.

In a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the N-terminus of the translocation component. Similarly, in a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the C-terminus of the translocation component.

In a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the N-terminus of the TM component. Similarly, in a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the C-terminus of the TM component.

The polypeptide of the present invention may include one or more (e.g. two, three, four, five or more) destructive protease cleavage sites. Where more than one destructive cleavage site is included, each cleavage site may be the same or different. In this regard, use of more than one destructive cleavage site provides improved off-site inactivation. Similarly, use of two or more different destructive cleavage sites provides additional design flexibility.

The destructive cleavage site(s) may be engineered into any of the following component(s) of the polypeptide: the non-cytotoxic protease component; the translocation component; the Targeting Moiety; or the spacer peptide (if present). In this regard, the destructive cleavage site(s) are chosen to ensure minimal adverse effect on the potency of the polypeptide (for example by having minimal effect on the targeting/binding regions and/or translocation domain, and/or on the non-cytotoxic protease domain) whilst ensuring that the polypeptide is labile away from its target site/target cell.

Preferred destructive cleavage sites (plus the corresponding second proteases) are listed in the Table immediately below. The listed cleavage sites are purely illustrative and are not intended to be limiting to the present invention.

| Second protease | Destructive cleavage site recognition sequence | Tolerated recognition sequence variance P4-P3-P2-P1-▼-P1'-P2'-P3' P4 | P3 | P2 | P1 | P1' | P2' | P3' |
| --- | --- | --- | --- | --- | --- | --- | --- | --- |
| Thrombin | LVPR▼GS (SEQ ID NO: 78) | A, F, G, I, L, T, V or M | A, F, G, I, L, T, V, W or A | P | R | Not D or E | Not D or E | — |
| Thrombin | GR▼G | | | G | R | G | | |
| Factor Xa | IEGR▼ (SEQ ID NO: 75) | A, F, G, I, L, T, V or M | D or E | G | R | — | — | — |

-continued

| Second protease | Destructive cleavage site recognition sequence | Tolerated recognition sequence variance P4-P3-P2-P1-▼-P1'-P2'-P3' P4 | P3 | P2 | P1 | P1' | P2' | P3' |
|---|---|---|---|---|---|---|---|---|
| ADAM17 | PLAQA▼VRSSS (SEQ ID NO: 81) | | | | | | | |
| Human airway trypsin-like protease (HAT) | SKGR▼SLIGRV (SEQ ID NO: 82) | | | | | | | |
| ACE (peptidyl-dipeptidase A) | | — | — | — | — | Not P | Not D or E | N/A |
| Elastase (leukocyte) | MEA▼VTY (SEQ ID NO: 83) | M, R | E | A, H | V, T | V, T, H | Y | — |
| Furin | RXR/KR▼ (SEQ ID NO: 84) | R | X | R or K | R | | | |
| Granzyme | IEPD▼ | I | E | P | D | — | — | — |
| Caspase 1 | (SEQ ID NO: 85) | F, W, Y, L | — | H, A, T | D | Not P, E.D. Q.K or R | — | — |
| Caspase 2 | DVAD▼ (SEQ ID NO: 86) | D | V | A | D | Not P, E.D. Q.K or R | — | — |
| Caspase 3 | DMQD▼ (SEQ ID NO: 87) | D | M | Q | D | Not P, E.D. Q.K or R | — | — |
| Caspase 4 | LEVD▼ (SEQ ID NO: 88) | L | E | V | D | Not P, E.D. Q.K or R | — | — |
| Caspase 5 | | L or W | E | H | D | — | — | — |
| Caspase 6 | | V | E | H or I | D | Not P, E.D. Q.K or R | — | — |
| Caspase 7 | DEVD▼ (SEQ ID NO: 89) | D | E | V | D | Not P, E.D. Q.K or R | — | — |
| Caspase 8 | | I or L | E | T | D | Not P, E.D. Q.K or R | — | — |
| Caspase 9 | LEHD▼ (SEQ ID NO: 90) | L | E | H | D | — | — | — |
| Caspase 10 | IEHD▼ (SEQ ID NO: 91) | I | E | H | D | — | — | — |

Matrix metalloproteases (MMPs) are a preferred group of destructive proteases in the context of the present invention. Within this group, ADAM17 (EC 3.4.24.86, also known as TACE), is preferred and cleaves a variety of membrane-anchored, cell-surface proteins to "shed" the extracellular domains. Additional, preferred MMPs include adamalysins, serralysins, and astacins.

Another group of preferred destructive proteases is a mammalian blood protease, such as Thrombin, Coagulation Factor Vila, Coagulation Factor IXa, Coagulation Factor Xa, Coagulation Factor Xla, Coagulation Factor Xlla, Kallikrein, Protein C, and MBP-associated serine protease.

In one embodiment of the present invention, said destructive cleavage site comprises a recognition sequence having at least 3 or 4, preferably 5 or 6, more preferably 6 or 7, and particularly preferably at least 8 contiguous amino acid residues. In this regard, the longer (in terms of contiguous amino acid residues) the recognition sequence, the less likely non-specific cleavage of the destructive site will occur via an unintended second protease.

It is preferred that the destructive cleavage site of the present invention is introduced into the protease component and/or the Targeting Moiety and/or into the translocation component and/or into the spacer peptide. Of these four components, the protease component is preferred. Accordingly, the polypeptide may be rapidly inactivated by direct destruction of the non-cytotoxic protease and/or binding and/or translocation components.

Polypeptide Delivery

In use, the present invention employs a pharmaceutical composition, comprising a polypeptide, together with at least one component selected from a pharmaceutically acceptable carrier, excipient, adjuvant, propellant and/or salt.

The polypeptides of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of a polypeptide that is to be delivered locally, the polypeptide may be formulated as a cream (eg. for topical application), or for sub-dermal injection.

Local delivery means may include an aerosol, or other spray (eg. a nebuliser). In this regard, an aerosol formulation of a polypeptide enables delivery to the lungs and/or other nasal and/or bronchial or airway passages.

One route of administration is via laproscopic and/or localised injection. Alternatively (or in addition), delivery may be systemic such as via intravenous administration.

In the case of formulations for injection, it is optional to include a pharmaceutically active substance to assist retention at or reduce removal of the polypeptide from the site of administration. One example of such a pharmaceutically active substance is a vasoconstrictor such as adrenaline. Such a formulation confers the advantage of increasing the residence time of polypeptide following administration and thus increasing and/or enhancing its effect.

Polypeptides of the invention may be administered to a patient by intrathecal or epidural injection in the spinal column at the level of the spinal segment involved in the innervation of an affected organ.

The dosage ranges for administration of the polypeptides of the present invention are those to produce the desired therapeutic effect. It will be appreciated that the dosage range required depends on the precise nature of the polypeptide or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.0001-1 ng/kg, preferably 0.0001-0.5 ng/kg, more preferably 0.002-0.5 ng/kg, and particularly preferably 0.004-0.5 ng/kg. The unit dosage can vary from less that 1 picogram to 30 ng, but typically will be in the region of 0.01 to 1 ng per dose, which may be administered daily or preferably less frequently, such as weekly or six monthly.

A particularly preferred dosing regimen is based on 2.5 ng of polypeptide as the 1× dose. In this regard, preferred dosages are in the range 1×-100× (i.e. 2.5-250 ng).

Fluid dosage forms are typically prepared utilising the polypeptide and a pyrogen-free sterile vehicle. The polypeptide, depending on the vehicle and concentration used, can be either dissolved or suspended in the vehicle. In preparing solutions the polypeptide can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition/s to facilitate uniform distribution of the components.

Administration in accordance with the present invention may take advantage of a variety of delivery technologies including microparticle encapsulation, viral delivery systems or high-pressure aerosol impingement.

DEFINITIONS SECTION

Targeting Moiety (TM) means any chemical structure that functionally interacts with a Binding Site to cause a physical association between the polypeptide of the invention and the surface of a target cell (typically a mammalian cell, especially a human cell). The term TM embraces any molecule (ie. a naturally occurring molecule, or a chemically/physically modified variant thereof) that is capable of binding to a Binding Site on the target cell, which Binding Site is capable of internalisation (eg. endosome formation)—also referred to as receptor-mediated endocytosis. The TM may possess an endosomal membrane translocation function, in which case separate TM and Translocation Domain components need not be present in an agent of the present invention. Throughout this specification, specific TMs have been described, for example by reference to SEQ ID NOs. Reference to said TMs is merely exemplary, and the present invention embraces all variants and derivatives thereof, which retain the basic binding (i.e. targeting) ability of the exemplified TMs.

The TM of the present invention binds (preferably specifically binds) to the target cell in question. The term "specifically binds" preferably means that a given TM (e.g. with the additional fusion protein components such as the translocation component and/or the endopeptidase component) binds to the target cell with a binding affinity (Ka) of $10^8M^{-1}$ or greater, preferably $10^9M^{-1}$ or greater, more preferably $10^{10}$ $M^{-1}$ orgreater, and most preferably, $10^{11}$ $M^{-1}$ or greater.

Reference to TM in the present specification embraces fragments and variants thereof, which retain an ability to bind to the target cell and/or EGF (eg. ErbB) receptor in question. By way of example, a variant may have at least 70% or 75%, or at least 80% or 85%, or at least 90% or 95% amino acid sequence homology with a reference TM (eg. SEQ ID NO: 1, and/or the 37 amino acid sequence thereof that comprises the 6-cysteine backbone thereof). A variant may include one or more analogues of an amino acid (e.g. an unnatural amino acid), or a substituted linkage. Also, by way of example, the term fragment, when used in relation to a TM, means a peptide having at least thirty seven, or at least forty, or at least forty five, or at least fifty amino acid residues of the reference TM. The term fragment also relates to the above-mentioned variants. Thus, by way of example, a fragment of the present invention may comprise a peptide sequence having at least 37, 40, 45 or 50 amino acids, wherein the peptide sequence has at least 80% sequence homology over a corresponding peptide sequence (of contiguous) amino acids of the reference peptide. The EGF TM of the present invention has 99% or less, 97% or less, 95% or less, 93% or less, 91% or less, 89% or less, 87% or less, 85% or less, 83% or less, 81% or less, 79% or less, 77% or less, 75% or less, 73% or less, 71% or less sequence identity to naturally-occurring human EGF (SEQ ID NO: 1, and/or the 37 amino acid sequence thereof that comprises the 6-cysteine backbone thereof).

It is routine to confirm that a TM binds to the selected target cell. For example, a simple radioactive displacement experiment may be employed in which tissue or cells representative of a target cell (e.g. a mucus-secreting cell, or an inflammatory cell) are exposed to labelled (eg. tritiated) TM in the presence of an excess of unlabelled TM. In such an experiment, the relative proportions of non-specific and specific binding may be assessed, thereby allowing confirmation that the TM binds to the target cell. Optionally, the assay may include one or more binding antagonists, and the assay may further comprise observing a loss of TM binding. Examples of this type of experiment can be found in Hulme, E. C. (1990), Receptor-binding studies, a brief outline, pp. 303-

311, In Receptor biochemistry, A Practical Approach, Ed. E. C. Hulme, Oxford University Press.

The polypeptides of the present invention may lack a functional $H_C$ domain of a clostridial neurotoxin. Accordingly, said polypeptides are not able to bind rat synaptosomal membranes (via a clostridial $H_C$ component) in binding assays as described in Shone et al. (1985) Eur. J. Biochem. 151, 75-82. In a preferred embodiment, the polypeptides preferably lack the last 50 C-terminal amino acids of a clostridial neurotoxin holotoxin. In another embodiment, the polypeptides preferably lack the last 100, preferably the last 150, more preferably the last 200, particularly preferably the last 250, and most preferably the last 300 C-terminal amino acid residues of a clostridial neurotoxin holotoxin. Alternatively, the Hc binding activity may be negated/reduced by mutagenesis—by way of example, referring to BoNT/A for convenience, modification of one or two amino acid residue mutations (W1266 to L and Y1267 to F) in the ganglioside binding pocket causes the $H_C$ region to lose its receptor binding function. Analogous mutations may be made to non-serotype A clostridial peptide components, e.g. a construct based on botulinum B with mutations (W1262 to L and Y1263 to F) or botulinum E (W1224 to L and Y1225 to F). Other mutations to the active site achieve the same ablation of $H_C$ receptor binding activity, e.g. Y1267S in botulinum type A toxin and the corresponding highly conserved residue in the other clostridial neurotoxins. Details of this and other mutations are described in Rummel et al (2004) (Molecular Microbiol. 51:631-634), which is hereby incorporated by reference thereto.

The $H_C$ peptide of a native clostridial neurotoxin comprises approximately 400-440 amino acid residues, and consists of two functionally distinct domains of approximately 25 kDa each, namely the N-terminal region (commonly referred to as the $H_{CN}$ peptide or domain) and the C-terminal region (commonly referred to as the $H_{CC}$ peptide or domain). This fact is confirmed by the following publications, each of which is herein incorporated in its entirety by reference thereto: Umland TC (1997) Nat. Struct. Biol. 4: 788-792; Herreros J (2000) Biochem. J. 347: 199-204; Halpern J (1993) J. Biol. Chem. 268: 15, pp. 11188-11192; Rummel A (2007) PNAS104: 359-364; Lacey DB (1998) Nat. Struct. Biol. 5: 898-902; Knapp (1998) Am. Cryst. Assoc. Abstract Papers 25: 90; Swaminathan and Eswaramoorthy (2000) Nat. Struct. Biol. 7: 1751-1759; and Rummel A (2004) Mol. Microbiol. 51(3), 631-643. Moreover, it has been well documented that the C-terminal region ($H_{CC}$), which constitutes the C-terminal 160-200 amino acid residues, is responsible for binding of a clostridial neurotoxin to its natural cell receptors, namely to nerve terminals at the neuromuscular junction—this fact is also confirmed by the above publications. Thus, reference throughout this specification to a clostridial heavy-chain lacking a functional heavy chain $H_C$ peptide (or domain) such that the heavy-chain is incapable of binding to cell surface receptors to which a native clostridial neurotoxin binds means that the clostridial heavy-chain simply lacks a functional $H_{CC}$ peptide. In other words, the $H_{CC}$ peptide region is either partially or wholly deleted, or otherwise modified (e.g. through conventional chemical or proteolytic treatment) to inactivate its native binding ability for nerve terminals at the neuromuscular junction.

Thus, in one embodiment, a clostridial $H_N$ peptide of the present invention lacks part of a C-terminal peptide portion ($H_{CC}$) of a clostridial neurotoxin and thus lacks the $H_C$ binding function of native clostridial neurotoxin. By way of example, in one embodiment, the C-terminally extended clostridial $H_N$ peptide lacks the C-terminal 40 amino acid residues, or the C-terminal 60 amino acid residues, or the C-terminal 80 amino acid residues, or the C-terminal 100 amino acid residues, or the C-terminal 120 amino acid residues, or the C-terminal 140 amino acid residues, or the C-terminal 150 amino acid residues, or the C-terminal 160 amino acid residues of a clostridial neurotoxin heavy-chain. In another embodiment, the clostridial $H_N$ peptide of the present invention lacks the entire C-terminal peptide portion ($H_{CC}$) of a clostridial neurotoxin and thus lacks the $H_C$ binding function of native clostridial neurotoxin. By way of example, in one embodiment, the clostridial $H_N$ peptide lacks the C-terminal 165 amino acid residues, or the C-terminal 170 amino acid residues, or the C-terminal 175 amino acid residues, or the C-terminal 180 amino acid residues, or the C-terminal 185 amino acid residues, or the C-terminal 190 amino acid residues, or the C-terminal 195 amino acid residues of a clostridial neurotoxin heavy-chain. By way of further example, the clostridial $H_N$ peptide of the present invention lacks a clostridial $H_{CC}$ reference sequence selected from the group consisting of:

Botulinum type A neurotoxin—amino acid residues (Y1111-L1296)

Botulinum type B neurotoxin—amino acid residues (Y1098-E1291)

Botulinum type C neurotoxin—amino acid residues (Y1112-E1291)

Botulinum type D neurotoxin—amino acid residues (Y1099-E1276)

Botulinum type E neurotoxin—amino acid residues (Y1086-K1252)

Botulinum type F neurotoxin—amino acid residues (Y1106-E1274)

Botulinum type G neurotoxin—amino acid residues (Y1106-E1297)

Tetanus neurotoxin—amino acid residues (Y1128-D1315).

The above-identified reference sequences should be considered a guide as slight variations may occur according to sub-serotypes.

The protease of the present invention embraces all non-cytotoxic proteases that are capable of cleaving one or more SNARE proteins of the exocytic fusion apparatus in eukaryotic cells.

The protease of the present invention is preferably a bacterial protease (or fragment thereof). More preferably the bacterial protease is selected from the genera *Clostridium* (e.g. a clostridial L-chain). The protease of the present invention preferably demonstrates a serine or metalloprotease activity (e.g. endopeptidase activity).

The present invention also embraces variant non-cytotoxic proteases (ie. variants of naturally-occurring protease molecules), so long as the variant proteases still demonstrate the requisite protease activity. By way of example, a variant may have at least 70%, preferably at least 80%, more preferably at least 90%, and most preferably at least 95 or at least 98% amino acid sequence homology with a reference protease sequence. Thus, the term variant includes non-cytotoxic proteases having enhanced (or decreased) endopeptidase activity—particular mention here is made to the increased $K_{cat}/K_m$ of BoNT/A mutants Q161A, E54A, and K165L see Ahmed, S. A. (2008) Protein J. DOI 10.1007/s10930-007-9118-8, which is incorporated by reference thereto. The term fragment, when used in relation to a protease, typically means a peptide having at least 150, preferably at least 200, more preferably at least 250, and most preferably at least 300 amino acid residues of the reference protease. As with the TM 'fragment' component (discussed above), protease 'fragments' of the present invention embrace fragments of variant proteases based on a reference sequence.

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

BoNTs are the most potent toxins known, with median lethal dose (LD50) values for mice ranging from 0.5 to 5 ng/kg depending on the serotype. BoNTs are adsorbed in the gastrointestinal tract, and, after entering the general circulation, bind to the presynaptic membrane of cholinergic nerve terminals and prevent the release of their neurotransmitter acetylcholine.

BoNTs share a common structure, being di-chain proteins of ~150 kDa, consisting of a heavy chain (H-chain) of ~100 kDa covalently joined by a single disulphide bond to a light chain (L-chain) of ~50 kDa. The H-chain consists of two domains, each of ~50 kDa. The C-terminal domain ($H_C$) is required for the high-affinity neuronal binding, whereas the N-terminal domain ($H_N$) is proposed to be involved in membrane translocation. The L-chain is a zinc-dependent metalloprotease responsible for the cleavage of the substrate SNARE protein.

The term L-chain fragment means a component of the L-chain of a neurotoxin, which fragment demonstrates a metalloprotease activity and is capable of proteolytically cleaving a non-neuronal SNARE protein.

Examples of suitable protease (reference) sequences include:

Botulinum type A neurotoxin—amino acid residues (1-448)

Botulinum type B neurotoxin—amino acid residues (1-440)

Botulinum type C neurotoxin—amino acid residues (1-441)

Botulinum type D neurotoxin—amino acid residues (1-445)

Botulinum type E neurotoxin—amino acid residues (1-422)

Botulinum type F neurotoxin—amino acid residues (1-439)

Botulinum type G neurotoxin—amino acid residues (1-441)

Tetanus neurotoxin—amino acid residues (1-457)

The above-identified reference sequence should be considered a guide as slight variations may occur according to sub-serotypes. By way of example, US 2007/0166332 (hereby incorporated by reference thereto) cites slightly different clostridial sequences:

Botulinum type A neurotoxin—amino acid residues (M1-K448)

Botulinum type B neurotoxin—amino acid residues (M1-K441)

Botulinum type C neurotoxin—amino acid residues (M1-K449)

Botulinum type D neurotoxin—amino acid residues (M1-R445)

Botulinum type E neurotoxin—amino acid residues (M1-R422)

Botulinum type F neurotoxin—amino acid residues (M1-K439)

Botulinum type G neurotoxin—amino acid residues (M1-K446)

Tetanus neurotoxin—amino acid residues (M1-A457)

A variety of clostridial toxin fragments comprising the light chain can be useful in aspects of the present invention with the proviso that these light chain fragments can specifically target the core components of the neurotransmitter release apparatus and thus participate in executing the overall cellular mechanism whereby a clostridial toxin proteolytically cleaves a substrate. The light chains of clostridial toxins are approximately 420-460 amino acids in length and comprise an enzymatic domain. Research has shown that the entire length of a clostridial toxin light chain is not necessary for the enzymatic activity of the enzymatic domain. As a non-limiting example, the first eight amino acids of the BoNT/A light chain are not required for enzymatic activity. As another non-limiting example, the first eight amino acids of the TeNT light chain are not required for enzymatic activity. Likewise, the carboxyl-terminus of the light chain is not necessary for activity. As a non-limiting example, the last 32 amino acids of the BoNT/A light chain (residues 417-448) are not required for enzymatic activity. As another non-limiting example, the last 31 amino acids of the TeNT light chain (residues 427-457) are not required for enzymatic activity. Thus, aspects of this embodiment can include clostridial toxin light chains comprising an enzymatic domain having a length of, for example, at least 350 amino acids, at least 375 amino acids, at least 400 amino acids, at least 425 amino acids and at least 450 amino acids. Other aspects of this embodiment can include clostridial toxin light chains comprising an enzymatic domain having a length of, for example, at most 350 amino acids, at most 375 amino acids, at most 400 amino acids, at most 425 amino acids and at most 450 amino acids.

The non-cytotoxic protease component of the present invention preferably comprises a BoNT/A, C or D serotype L-chain (or fragment or variant thereof).

The polypeptides of the present invention, especially the protease component thereof, may be PEGylated—this may help to increase stability, for example duration of action of the protease component. PEGylation is particularly preferred when the protease comprises a BoNT/E protease. PEGylation preferably includes the addition of PEG to the N-terminus of the protease component. By way of example, the N-terminus of a protease may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is incorporated in its entirety by reference thereto.

The polypeptides of the present invention may include mutations and/deletions at one or more "secondary modification sites"—these sites are targeted and acted upon by enzymes (such as intracellular enzymes), which alter the biological persistence of the polypeptides of the invention. Such mutations/deltions may comprise the mutation or deletion of part or all of said one or more secondary modification sites. Such an increase in biological persistence is particular desired when longevity of action of the non-cytotoxic protease component of the present invention is desired. Alternatively, the polypeptides of the invention may include the addition of one or more secondary modification site.

The mutation or deletion of part or all of a secondary modification site found in a polypeptide of the present invention, or the addition of a secondary modification site to a polypeptide of the present invention, may lead to an enhanced biological persistence of the polypeptide. In general terms, the biological persistence of the polypeptide may be about 20% to about 300% greater than in the absence of any structural modification to a secondary modification site. Thus, inhibition of secretion from target cells is increased by about 20% to about 300%.

The enhanced biological persistence may take the form of an increased biological half-life of the polypeptide. The biological half-life of the polypeptide is preferably increased by about 10%; more preferably, the biological half-life of the polypeptide is increased by about 100%.

By way of example, botulinum neurotoxin A and botulinum neurotoxin E have the following potential secondary modification sites, as shown in Tables A and B, respectively. These sites may be targeted for mutation or deletion of all or part of the site.

TABLE A

| |
|---|
| N-glycosylation: 173-NLTR; 382-NYTI; 411-NFTK; 417-NFTG |
| Casein kinase II (CK-2) phosphorylation sites: 51-TNPE; 70-SYYD; 79-TDNE; 120-STID; 253-SGLE; 258-SFEE; 275-SLQE; 384-TIYD |
| N-terminal myristylation sites: 15-GVDIAY; 141-GSYRSE; 254-GLEVSF |
| Protein kinase C (PKC) phosphorylation sites: 142-SYR; 327-SGK; 435-TSK |
| Tyrosine phosphorylation sites: 92-KLFERIY; 334-KLKFDKLY |
| N-glycosylation: 97-NLSG; 138-NGSG; 161-NSSN; 164-NISL; 365-NDSI; 370-NISE |

TABLE B

| |
|---|
| Casein kinase II (CK-2) phosphorylation sites: 51-TPQD; 67-SYYD; 76-SDEE; 130-SAVE; 198-SMNE; 247-TNIE; 333-SFTE; 335-TEFD |
| N-terminal myristylation sites: 220-GLYGAK; 257-GTDLNI; 386-GQNANL |
| Protein kinase C (PKC) phosphorylation sites: 60-SLK; 166-SLR; 191-SFR; 228-TTK; 234-TQK; 400-TGR; 417-SVK |
| Tyrosine kinase phosphorylation sites: 62-KNGDSSY (SEQ ID NO: 92); 300-KDVFEAKY (SEQ ID NO: 93) |

A further example is the addition of a casein kinase II phosphorylation site, such as TDNE to a polypeptide of the present invention.

Further details are described in WO 2002/40506, which is herein incorporated in its entirety by reference thereto.

The polypeptides of the present invention may comprise one or more tyrosine phosphorylation sites in addition to any naturally existing tyrosine phosphorylation sites already present. The one or more additional tyrosine phosphorylation sites may be present in the non-cytotoxic protease component of the polypeptide, in the translocating domain of the polypeptide, or in the targeting domain of the polypeptide. Such sites may be added to the polypeptide as an addition to the polypeptide sequence, or may be substituted into the polypeptide sequence. By way of example, the tyrosine phosphorylation site may substitute about 1-8, or about 1-4, consecutive amino acids of the non-cytotoxic protease component.

The additional presence of such sites may increase the biological persistence of the polypeptides. In this regard, increased biological persistence may result in an increased duration of action of the polypeptide, or an increased half-life of the polypeptide, or both.

Any tyrosine phosphorylation site is suitable for use in the polypeptides of the present invention. By way of example, suitable tyrosine phosphorylation sites include KLFERIY (SEQ ID NO: 94) and KLKFDKLY (SEQ ID NO: 95).

Further details are provided in U.S. Pat. No. 7,223,577, which is herein incorporated in its entirety by reference thereto.

The polypeptides of the present invention may also have their biological persistence enhanced by the presence within the polypeptide of leucine-based motifs. The leucine-based motifs may be added in addition to the polypeptide sequence or included as a substitution.

A leucine-based motif may comprise seven contiguous amino acids. These may be further described as consisting of a group of five amino acids (a quintet) and a group immediately adjacent of two amino acids (a duplet). The duplet of amino acids may be located at either the N-terminal or C-terminal end of the leucine-based motif.

The quintet of amino acids may include at least one acidic amino acid selected from the group consisting of glutamic acid and aspartic acid.

The duplet of amino acids includes at least one hydrophobic acid; examples of such hydrophobic amino acids include leucine, isoleucine, methionine, alanine, phenylalanine, tryptophan, valine and tyrosine. The duplet of amino acids is preferably a leucine-leucine, a leucine-isoleucine, an isoleucine-leucine, an isoleucine-isoleucine or a leucine-methionine. The duplet of amino acids is even more preferably a leucine-leucine.

The quintet of amino acids may comprise at least one amino acid containing a hydroxyl group; examples of such amino acids include serine, threonine and tyrosine. The hydroxyl-containing amino acid is preferably phosphorylated. Even more preferably, the hydroxyl-containing amino acid is a serine which can be phosphorylated to allow for the binding of adapter proteins.

The above-described leucine-based motifs may also comprise modified amino acids. By way of example, a leucine-based motif may include a halogenated leucine, preferably a fluorinated leucine.

Examples of suitable leucine-based motifs include (where x can be any amino acid) xDxxxLL (SEQ ID NO: 96), xExxxLL (SEQ ID NO: 97), xDxxxLI (SEQ ID NO: 98), xDxxxLM (SEQ ID NO: 99), xExxxLI (SEQ ID NO: 100), xExxxIL (SEQ ID NO: 101), xExxxLM (SEQ ID NO: 102). A further example of a suitable leucine-based motif is phenylalanine-glutamate-phenylalanine-tyrosine-lysine-leucine-leucine.

Additional examples of leucine-based motifs (derived from various species) which are suitable for use in the polypeptides of the present invention are found in the table below.

| Species | Sequence | |
|---|---|---|
| *Botulinum* type A | FEFYKLL | (SEQ ID NO: 103) |
| Rat VMAT1 | EEKRAIL | (SEQ ID NO: 104) |
| Rat VMAT2 | EEKMAIL | (SEQ ID NO: 105) |
| Rat VAChT | SERDVLL | (SEQ ID NO: 106) |
| Rat δ | VDTQVLL | (SEQ ID NO: 107) |
| Mouse δ | AEVQALL | (SEQ ID NO: 108) |

-continued

| Species | Sequence | |
|---|---|---|
| Frog γ/δ | SDKQNLL | (SEQ ID NO: 109) |
| Chicken γ/δ | SDRQNLI | (SEQ ID NO: 110) |
| Sheep δ | ADTQVLM | (SEQ ID NO: 111) |
| Human CD3γ | SDKQTLL | (SEQ ID NO: 112) |
| Human CD4 | SQIKRLL | (SEQ ID NO: 113) |
| Human δ | ADTQALL | (SEQ ID NO: 114) |
| *S. cerevisiae* Vam3p | NEQSPLL | (SEQ ID NO: 115) |

VMAT: vesicular monoamine transporter.
VAChT: vesicular acetylcholine transporter.
*S. cerevisiae* Vam3p: a yeast homologue of synaptobrevin.
Underlined serine residues are potential sites of phosphorylation.

In addition to the use of leucine-based motifs as described above, the polypeptides of the present invention may also comprise tyrosine-based motifs. The presence of a tyrosine-based motif may act to increase the biological persistence of the polypeptide. Tyrosine-based motifs suitable for use in the present invention comprise the sequence Y-X-X-Hy (SEQ ID NO: 116), where Y is tyrosine, X is any amino acid, and Hy is a hydrophobic amino acid. An example of such a tyrosine-based motif described in U.S. Pat. No. 7,223,577 is YKLL (SEQ ID NO: 117).

Further details are provided in WO 2005068494, which is herein incorporated in its entirety by reference thereto.

A Translocation Domain is a molecule that enables translocation of a protease into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (eg. $H_N$ domain). As with the TM 'fragment' component (discussed above), translocation 'fragments' of the present invention embrace fragments of variant translocation domains based on the reference sequences.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, such as the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. The H-chain lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is incapable of binding to the Binding Site on a target cell to which native clostridial neurotoxin (i.e. holotoxin) binds.

Examples of suitable (reference) Translocation Domains include:

- Botulinum type A neurotoxin—amino acid residues (449-871)
- Botulinum type B neurotoxin—amino acid residues (441-858)
- Botulinum type C neurotoxin—amino acid residues (442-866)
- Botulinum type D neurotoxin—amino acid residues (446-862)
- Botulinum type E neurotoxin—amino acid residues (423-845)
- Botulinum type F neurotoxin—amino acid residues (440-864)
- Botulinum type G neurotoxin—amino acid residues (442-863)
- Tetanus neurotoxin—amino acid residues (458-879)

The above-identified reference sequence should be considered a guide as slight variations may occur according to sub-serotypes. By way of example, US 2007/0166332 (hereby incorporated by reference thereto) cites slightly different clostridial sequences:

- Botulinum type A neurotoxin—amino acid residues (A449-K871)
- Botulinum type B neurotoxin—amino acid residues (A442-S858)
- Botulinum type C neurotoxin—amino acid residues (T450-N866)
- Botulinum type D neurotoxin—amino acid residues (D446-N862)

Botulinum type E neurotoxin—amino acid residues (K423-K845)

Botulinum type F neurotoxin—amino acid residues (A440-K864)

Botulinum type G neurotoxin—amino acid residues (S447-S863)

Tetanus neurotoxin—amino acid residues (S458-V879)

In the context of the present invention, a variety of Clostridial toxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial toxin proteolytically cleaves a substrate. The $H_N$ regions from the heavy chains of Clostridial toxins are approximately 410-430 amino acids in length and comprise a translocation domain. Research has shown that the entire length of a $H_N$ region from a Clostridial toxin heavy chain is not necessary for the translocating activity of the translocation domain. Thus, aspects of this embodiment can include clostridial toxin $H_N$ regions comprising a translocation domain having a length of, for example, at least 350 amino acids, at least 375 amino acids, at least 400 amino acids and at least 425 amino acids. Other aspects of this embodiment can include clostridial toxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Henderson et al (1997) in *The Clostridia: Molecular Biology and Pathogenesis*, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial (reference) Translocation Domain origins include, but not be restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.,* 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS,* 89, pp. 7934-7938], and amphiphilic peptides [Murata et al (1992) *Biochem.,* 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral (reference) Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the (reference) Translocation Domains listed in Table (below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

| Translocation Domain source | Amino acid residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGWE GMIDGWYG, (SEQ ID NO: 118), and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

The polypeptides of the present invention may further comprise a translocation facilitating domain. Said domain facilitates delivery of the non-cytotoxic protease into the cytosol of the target cell and are described, for example, in WO 08/008,803 and WO 08/008,805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (eg. influenza A virus fusogenic peptide domain of 23 amino acids), alphavirus fusogenic peptide domain (eg. Semliki Forest virus fusogenic peptide domain of 26 amino acids), vesiculovirus fusogenic peptide domain (eg. vesicular stomatitis virus fusogenic peptide domain of 21 amino acids), respirovirus fusogenic peptide domain (eg. Sendai virus fusogenic peptide domain of 25 amino acids), morbiliivirus fusogenic peptide domain (eg. Canine distemper virus fusogenic peptide domain of 25 amino acids), avulavirus fusogenic peptide domain (eg. Newcastle disease virus fusogenic peptide domain of 25 amino acids), henipavirus fusogenic peptide domain (eg. Hendra virus fusogenic peptide domain of 25 amino acids), metapneumovirus fusogenic peptide domain (eg. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a Clostridial toxin $H_{CN}$ domain or a fragment or variant thereof. In more detail, a Clostridial toxin $H_{CN}$ translocation facilitating domain may have a length of at least 200 amino acids, at least 225 amino acids, at least 250 amino acids, at least 275 amino acids. In this regard, a Clostridial toxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin—amino acid residues (872-1110)

Botulinum type B neurotoxin—amino acid residues (859-1097)

Botulinum type C neurotoxin—amino acid residues (867-1111)

Botulinum type D neurotoxin—amino acid residues (863-1098)

Botulinum type E neurotoxin—amino acid residues (846-1085)

Botulinum type F neurotoxin—amino acid residues (865-1105)

Botulinum type G neurotoxin—amino acid residues (864-1105)

Tetanus neurotoxin—amino acid residues (880-1127)

The above sequence positions may vary a little according to serotype/sub-type, and further examples of suitable (reference) Clostridial toxin $H_{CN}$ domains include:

Botulinum type A neurotoxin—amino acid residues (874-1110)

Botulinum type B neurotoxin—amino acid residues (861-1097)

Botulinum type C neurotoxin—amino acid residues (869-1111)

Botulinum type D neurotoxin—amino acid residues (865-1098)

Botulinum type E neurotoxin—amino acid residues (848-1085)

Botulinum type F neurotoxin—amino acid residues (867-1105)

Botulinum type G neurotoxin—amino acid residues (866-1105)

Tetanus neurotoxin—amino acid residues (882-1127)

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a Clostridial toxin $H_{CN}$ translocation facilitating domain may be combined with a non-clostridial translocation domain peptide. Alternatively, a Clostridial toxin $H_{CN}$ facilitating domain may be combined or with a clostridial translocation domain peptide, examples of which include:

Botulinum type A neurotoxin—amino acid residues (449-1110)

Botulinum type B neurotoxin—amino acid residues (442-1097)

Botulinum type C neurotoxin—amino acid residues (450-1111)

Botulinum type D neurotoxin—amino acid residues (446-1098)

Botulinum type E neurotoxin—amino acid residues (423-1085)

Botulinum type F neurotoxin—amino acid residues (440-1105)

Botulinum type G neurotoxin—amino acid residues (447-1105)

Tetanus neurotoxin—amino acid residues (458-1127)

Sequence Homology:

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by iterative Refinement as Assessed by Reference to Structural Alignments, 264(4) J. Mol. Biol. 823838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals; A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{(Total number of identical matches)}}{\begin{array}{c}\text{[length of the longer sequence plus the number of gaps introduced}\\ \text{into the longer sequence in order to align the two sequences]}\end{array}}\times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine
  lysine
  histidine
Acidic: glutamic acid
  aspartic acid
Polar: glutamine
  asparagine
Hydrophobic: leucine
  isoleucine
  valine
Aromatic: phenylalanine
  tryptophan
  tyrosine
Small: glycine
  alanine
  serine
  threonine
  methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for amino acid residues of polypeptides of the present invention. Essential amino acids in the polypeptides of the present invention can be identified according to procedures known in the art, such as site-directed mutagenesis or alanine-scanning mutagenesis (Cunningham and Wells, *Science* 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

SUMMARY OF EXAMPLES

Example 1 Preparation of a Lha Backbone Construct
Example 2 Construction of $LH_N$/A-EGFv1 fusion protein
Example 3 Expression and purification of a $LH_N$/A-CT-EGF v1 fusion protein
Example 4 EGF binding affinity assay
Example 5 EGF binding affinity assay
Example 6 Treatment of a patient suffering from chronic bronchitis
Example 7 Method for treating acromegalic patients resistant to somatostatin analogues
Example 8 Method for suppressing neuroendocrine tumour cells
Example 9 Comparison of EGF and EGF fusion proteins in an EGF receptor activation assay
Example 10 Comparison of EGF, EGF mutein and EGF mutein fusion proteins in an EGF receptor activation assay
Example 11 Treatment of a patient suffering from rhinitis
Example 12 Treatment of a patient suffering from asthma
Example 13 Treatment of a patient suffering from COPD
Example 14 Treatment of a patient suffering from asthma
Example 15 Treatment of a patient suffering from colon cancer
Example 16 Treatment of a patient suffering from psoriasis
Example 17 Treatment of a patient suffering from eczema
Example 18 Treatment of a patient suffering from colorectal cancer
Example 19 Treatment of a patient suffering from prostate cancer
Example 20 Treatment of a patient suffering from nsc lung cancer
Example 21 Treatment of a patient suffering from breast cancer

SUMMARY OF SEQ ID NOS

SEQ ID 1 Amino acid sequence for naturally-occurring, human epidermal growth factor (EGF)
SEQ ID 2 DNA sequence of LHA
SEQ ID 3 DNA sequence of LHB
SEQ ID 4 DNA sequence of LHC
SEQ ID 5 DNA sequence of LHD
SEQ ID 6 Protein sequence of EGF variant H16N
SEQ ID 7 Protein sequence of EGF variant v1
SEQ ID 8 Protein sequence of EGF variant H16Q
SEQ ID 9 Protein sequence of EGF variant v2
SEQ ID 10 Protein sequence of EGF variant W49L
SEQ ID 11 Protein sequence of EGF variant v3
SEQ ID 12 Protein sequence of EGF variant W491
SEQ ID 13 Protein sequence of EGF variant v4
SEQ ID 14 Protein sequence of EGF variant W49V
SEQ ID 15 Protein sequence of EGF variant v5
SEQ ID 16 Protein sequence of EGF variant W49A
SEQ ID 17 Protein sequence of EGF variant v6 (G12Q)
SEQ ID 18 Protein sequence of EGF variant W49G
SEQ ID 19 Protein sequence of EGF variant v7 (H16D)
SEQ ID 20 Protein sequence of EGF variant W49S
SEQ ID 21 Protein sequence of EGF variant v8 (Y13W)
SEQ ID 22 Protein sequence of EGF variant W49T
SEQ ID 23 Protein sequence of EGF variant v9 (Q43A)
SEQ ID 24 Protein sequence of EGF variant W49N
SEQ ID 25 Protein sequence of EGF variant v10 (H16A)
SEQ ID 26 Protein sequence of EGF variant W49Q
SEQ ID 27 Protein sequence of EGF variant v11 (L15A)
SEQ ID 28 Protein sequence of EGF variant $H_{16}N$_W49L
SEQ ID 29 Protein sequence of EGF variant v12 (V19E)
SEQ ID 30 Protein sequence of EGF variant H16Q_W49L
SEQ ID 31 Protein sequence of EGF variant v13 (V34D)
SEQ ID 32 Protein sequence of EGF variant $H_{16}N$_W491
SEQ ID 33 Protein sequence of LHA-EGFv1 (Xa activation)
SEQ ID 34 Protein sequence of EGF variant H16Q_W491
SEQ ID 35 Protein sequence of LHA-EGFv2 (Xa activation)
SEQ ID 36 Protein sequence of EGF variant $H_{16}N$_W50A
SEQ ID 37 Protein sequence of LHA-EGFv3
SEQ ID 38 Protein sequence of EGF variant H16Q_W50A
SEQ ID 39 Protein sequence of LHA-EGFv4

SEQ ID 40 Protein sequence of EGF variant $H_{16}N$_W49L_W50A
SEQ ID 41 Protein sequence of LHA-EGFv5
SEQ ID 42 Protein sequence of EGF variant H16Q_W49L_W50A
SEQ ID 43 Protein sequence of LHA-EGFv6
SEQ ID 44 Protein sequence of EGF variant $H_{16}N$_W49I_W50A
SEQ ID 45 Protein sequence of LHC-EGFv7
SEQ ID 46 Protein sequence of EGF variant H16Q_W49I_W50A
SEQ ID 47 Protein sequence of LHC-EGFv8
SEQ ID 48 Protein sequence of EGF variant $H_{16}N$_W49L_W50A_E24G
SEQ ID 49 Protein sequence of LHC-EGFv9
SEQ ID 50 Protein sequence of EGF variant $H_{16}N$_W49L_W50A_E24G_A25T
SEQ ID 51 Protein sequence of LHC-EGFv10
SEQ ID 52 Protein sequence of EGF variant $H_{16}N$_W49L_W50A_E24G_A25S
SEQ ID 53 Protein sequence of LHC-EGFv11
SEQ ID 54 Protein sequence of EGF variant $H_{16}N$_W49L_W50A_E24G_A25T_K28R
SEQ ID 55 Protein sequence of LHC-EGFv12
SEQ ID 56 Protein sequence of EGF variant $H_{16}N$_W49L_W50A_E24G_A25T_K28R_S4P
SEQ ID 57 Protein sequence of LHC-EGFv13
SEQ ID 58 Protein sequence of EGF variant $H_{16}N$_W49L_W50A_E24G_A25T_K28R_S4P_E5K
SEQ ID 59 Protein sequence of LHB-EGFv1
SEQ ID 60 Protein sequence of EGF variant v3
SEQ ID 61 Protein sequence of LHB-EGFv5
SEQ ID 62 Protein sequence of Tetanus LHN-EGFv1
SEQ ID 63 Protein sequence of LHD-EGFv6 (protease sensitivity site)
SEQ ID 64 Protein sequence of LHD-EGFv3
SEQ ID 65 Protein sequence of LH D-EGFv11
SEQ ID 66 Protein sequence of M26-IgA1-HC-EGFv3
SEQ ID 67 Protein sequence of M26-IgA1-HC-EGFv11
SEQ ID 68 Protein sequence of Tetanus LHN-EGFv3
SEQ ID 69 Protein sequence of LHA-CP-EGFv2
SEQ ID 70 Protein sequence of LHD-EGFv2
SEQ ID 71 Protein sequence of LHC-CP-EGFv2
SEQ ID 72 Protein sequence of LHC-EGFv3
SEQ ID 73 DNA sequence of a EGF variant v3

FIG. 1 illustrates the data generated in Example 10 in which EGF, EGF mutein, or EGF mutein fusion protein is tested for its ability (at increasing concentrations) to activate an EGF receptor. A low $pEC_{50}$ value indicates relatively poor receptor activation.

FIG. 2 illustrates a 3D model of EGF-$EGF^R$ binding, in which Binding Interface 1 (residues 31-40 of EGF), Binding Interface 2 (residues 41-45 of EGF), and the Leading Edge (residues 48-51 in combination with 15-17 of EGF) are identified.

EXAMPLE 1

Preparation of a LHA Backbone Construct

The following procedure creates a clone for use as an expression backbone for multidomain protein expression. This example is based on preparation of a serotype A based clone (SEQ ID 2), though the procedures and methods are equally applicable to other $LH_N$ serotypes such as serotype B (SEQ ID 3), serotype C (SEQ ID 4) and serotype D (SEQ ID 5)

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the pET (Novagen) expression vector which has the desired restriction sequences within the multiple cloning site in the correct orientation for construct insertion (NdeI-BamHI-SalI-PstI-SpeI-XbaI-HindIII). A fragment of the expression vector has been removed to create a non-mobilisable plasmid and a variety of different fusion tags have been inserted to increase purification options.

Preparation of Lca

The DNA sequence is designed by back translation of the LC/A amino acid sequence (obtained from freely available database sources such as GenBank (accession number P10845) using one of a variety of reverse translation software tools (for example Backtranslation tool v2.0 (Entelechon)). BamHI/SalI recognition sequences are incorporated at the 5' and 3' ends respectively of the sequence maintaining the correct reading frame. The DNA sequence is screened (using software such as SeqBuilder, DNASTAR Inc.) for restriction enzyme cleavage sequences incorporated during the back translation. Any cleavage sequences that are found to be common to those required by the cloning system are removed by the Backtranslation tool from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/A open reading frame (ORF) is then commercially synthesized (for example by Entelechon, Geneart or Sigma-Genosys) and is provided in the pCR 4 vector.

Preparation of $H_N$/A Insert

The DNA sequence is designed by back translation of the $H_N$/A amino acid sequence (obtained from freely available database sources such as GenBank (accession number P10845) using one of a variety of reverse translation software tools (for example Back translation tool v2.0 (Entelechon)). A PstI restriction sequence added to the N-terminus and XbaI-stop codon-HindIII to the C-terminus ensuring the correct reading frame in maintained. The DNA sequence is screened (using software such as SeqBuilder, DNASTAR Inc.) for restriction enzyme cleavage sequences incorporated during the back translation. Any sequences that are found to be common to those required by the cloning system are removed by the Backtranslation tool from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Preparation of the Interdomain (LC-$H_N$ Linker)

The LC-$H_N$ linker can be designed from first principle, using the existing sequence information for the linker as the template. For example, the serotype A linker (in this case defined as the inter-domain polypeptide region that exists between the cysteines of the disulphide bridge between LC and $H_N$) has the sequence VRGIIPFKTKSLDEGYNKALNDL (SEQ ID NO: 119). This sequence information is freely available from available database sources such as GenBank (accession number P10845). An alternative linker can be used for example composed of a Glycine-Serine linker ($GGGGS_3$) (SEQ ID NO: 120). For generation of a specific protease cleavage site, the native recognition sequence for Factor Xa (IEGR (SEQ ID NO: 75) or IDGR (SEQ ID NO: 76)) can be used for example in the modified sequence VDGIITSKTKSLIDGR (SEQ ID NO: 121) or GGGGSGGGGSGGGGSIEGRGGGGSGGGGSGGGGS (SEQ ID NO: 122) or GGGGSGGGGSGGGGSIEGR (SEQ ID NO: 123) or the recognition sequence for the Light Chain of Enterokinase (DDDDK (SEQ ID NO: 74)) can be inserted, for example into the activation loop to generate the sequence VDGIITSKTKSLDDDDK (SEQ ID NO: 124) or GGGGSGGGGSGGGGSD-DDDKGGGGSGGGGSGGGGS (SEQ ID NO: 125).

Using one of a variety of reverse translation software tools (for example Backtranslation tool v2.0 (Entelechon), the DNA sequence encoding the linker region is determined. BamHI/SalI and PstI/XbaI/stop codon/HindIII restriction enzyme sequences are incorporated at either end, in the correct reading frames. The DNA sequence is screened (using software such as Seqbuilder, DNASTAR Inc.) for restriction enzyme cleavage sequences incorporated during the back translation. Any sequences that are found to be common to those required by the cloning system are removed by the Backtranslation tool from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector. If it is desired to clone the linker out of pCR 4 vector, the vector is cleaved with either BamHI+SalI or PstI+XbaI combination restriction enzymes. This cleaved vector then serves as the recipient vector for insertion and ligation of either the LC DNA (cleaved with BamHI/SalI) or $H_N$ DNA (cleaved with PstI/XbaI) from (SEQ ID 2). Once the LC or the $H_N$ encoding DNA is inserted upstream or downstream of the linker DNA, the entire LC-linker or linker-$H_N$ DNA fragment can the be isolated and transferred to the backbone clone.

Assembly and Confirmation of the Backbone Clone

The LC-linker or the linker-$H_N$ is cut out from the pCR 4 cloning vector using BamHI/PstI or SalI/XbaI restriction enzymes or XhoI/NotI digests respectively. The pET expression vector containing $LH_N$/A (SEQ ID 2) is digested with the same enzymes but is also treated with antarctic phosphatase as an extra precaution to prevent re-circularisation. The LC-linker or linker-$H_N$ region and the pET vector backbone are gel purified. The purified insert and vector backbone are ligated together using T4 DNA ligase and the product is transformed with TOP10 cells which are then screened for LC-linker or linker-$H_N$ insertion using BamHI/SalI or BamHI/PstI or XhoI/NotI restriction enzymes to ensure the final backbone is correct. The integrity of the ORF DNA is checked by sequencing.

EXAMPLE 2

Construction of $LH_N$/A-EGFv3 Expression Vector

The following procedure creates a clone for use as an expression construct for multidomain fusion expression. This example is based on preparation of an EGFv3 fusion protein (eg. SEQ ID 37), though the procedures and methods are equally applicable to all EGF variants of the present invention, as well as to other $LH_N$ serotypes such as serotype B (SEQ ID 3), serotype C (SEQ ID 4) and serotype D (SEQ ID 5) fusion proteins of the present invention.

Preparation of Spacer-EGFv3 Insert

Activation Spacer

For presentation of EGF variant sequence at the C-terminus of the $H_N$ domain, a DNA sequence is designed to flank the spacer and targeting moiety (TM) regions allowing incorporation into the backbone clone (SEQ ID 1). The DNA sequence can be arranged as BamHI-SalI-PstI-XbaI-spacer-EGFv3-stop codon-HindIII. The DNA sequence can be designed using one of a variety of reverse translation software tools (for example EditSeq best *E. coli* reverse translation (DNASTAR Inc.), or Backtranslation tool v2.0 (Entelechon)). Once the TM DNA is designed, the additional DNA required to encode the preferred spacer is created in silico. It is important to ensure the correct reading frame is maintained for the spacer, EGFv3 and restriction sequences and that the XbaI sequence is not preceded by the bases, TC which would result in DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Insertion of Spacer-EGFv3 into Backbone

In order to create a LC-linker-$H_N$-spacer-EGFv3 construct using the backbone construct (SEQ ID 1) and the newly synthesised pCR 4-spacer-TM vector encoding the EGFv3 ™ (SEQ ID 73), the following two-step method is employed. Firstly, the $H_N$ domain is excised from the backbone clone using restriction enzymes PstI and XbaI and ligated into similarly digested pCR 4-spacer-EGFv3 vector. This creates an $H_N$-spacer-EGFv3 ORF in pCR 4 that can be excised from the vector using restriction enzymes PstI and HindIII for subsequent ligation into similarly cleaved backbone or expression construct. The final construct contains the LC-linker-$H_N$-spacer-EGFv3 ORF for transfer into expression vectors for expression to result in a fusion protein of the sequence (eg. SEQ ID 37).

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

EXAMPLE 3

Expression and Purification of a $LH_N$/A-CT-EGF v3 Fusion Protein

This example is based on preparation of a CT-EGF-A fusion activated by Factor Xa, though the procedures and methods are equally applicable to any other fusion protein of the present invention.

Expression of $LH_N$/A-CT-EGF v3 Fusion Protein

Expression of the CT-EGF v3-A fusion activated by Factor Xa fusion protein is achieved using the following protocol. Inoculate 100 ml of modified TB containing 0.2% glucosamine and 30 μg/ml kanamycin in a 250 ml flask with a single colony from the CT-EGF v3-A fusion. Grow the culture at 37° C., 225 rpm for 16 hours. Inoculate 1 L of modified TB containing 0.2% glucosamine and 30 μg/ml kanamycin in a 2 L flask with 10 ml of overnight culture. Grow cultures at 37° C. until an approximate $OD_{600nm}$ of 0.5 is reached at which point reduce the temperature to 16° C. After 1 hour induce the cultures with 1 mM IPTG and grow at 16° C. for a further 16 hours.

Purification of CT-EGF v3-A Fusion

Defrost falcon tube containing 35 ml 50 mM HEPES pH 7.2, 200 mM NaCl and approximately 10 g of *E. coli* BL21 (DE3) cell paste. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2 200 mM NaCl. Using a step gradient of 40 and 100 mM imidazole, wash away the non-specific bound protein and elute the fusion protein with 200 mM imidazole. Dialyse the eluted fusion protein against 5 L of 50 mM HEPES pH 7.2, 200 mM NaCl at 4° C. overnight and measure the OD of the dialysed fusion protein. Add 10 mg of Factor Xa per 1 mg fusion protein and incubate at 25° C. static overnight. Load onto a 0.1 M $NiSO_4$ charged Chelating column (20-30 ml column is sufficient) equilibrated with 50 mM HEPES pH 7.2 200 mM NaCl. Wash column to baseline with 50 mM HEPES pH 7.2, 200 mM NaCl. Using a step gradient of 40 and 100 mM imidazole, wash away the non-specific bound protein and elute the fusion protein with 200 mM imidazole. Dialyse the eluted fusion protein against 5 L of 50 mM HEPES pH 7.2 150 mM NaCl at 4° C. overnight and concentrate the fusion to about 2 mg/ml, aliquot sample and freeze at −20° C. Test purified protein using OD, BCA and purity analysis.

EXAMPLE 4

EGF Binding Affinity Assay

To compare binding affinity of EGF variants to wtEGF, a cell (NR6, a murine 3T3-derived fibroblast cell line; WT−EGF) that lacks endogenous EGF receptor (ErbB:−EGFR) is stably transfected with wild-type human EGFR to generate WT+EGF. Prior to performing binding assays, confluent WT-EGF cells were dislodged from tissue culture plates with Versene. EGF competition binding was measured in two ways to insure that equilibrium had been reached: $5\times10^4$ NR6WT cells were incubated with Alexa-488 labelled EGF wild-type for 30 min at 4° C. Increasing concentrations of unlabeled EGF wild-type or mutants were added, and samples were incubated for an additional 6 h at 4° C., with constant mixing. Alternatively, increasing concentrations of unlabeled EGF wild-type and mutants were first added to the cells for 30 min at 4° C., and Alexa-488 EGF wild-type was added for an additional 6 h at 4° C. Fluorescence intensity of cell surface Alexa-488 EGF wild-type labeling was measured by flow cytometry. Binding assays were performed in PBS supplemented with 1 mg/ml BSA (pH 7.4), under conditions where ligand depletion was negligible. Competition binding curves were fit using a four-point binding equation. Standard deviation represents replicate binding experiments performed in at least triplicate on different days using two different protein preparations.

EXAMPLE 5

EGF Binding Affinity Assay

To compare binding affinity of EGF variants for the EGF receptor the affinity was determined by measuring its competition with $^{125}$I-rEGF (recombinant EGF) for binding to paraformaldehyde-fixed A431 cells, a system wherein ligand and receptor internalisation processes are thus inhibited. Pure rEGF was used as a standard. A431 cells were grown to confluence in 96-well plates and then fixed on the day of the assay with 3% paraformaldehyde in PBS. The EGF variants and rEGF were serially diluted with 1.0 nM $^{125}$I-rEGF in PBS containing 0.1% BSA. Incubations were then carried out at 37° C. for 2 hours before each well was washed 3 times with PBS containing 0.15 mg/ml BSA. Finally wells were snapped apart and counted directly in a gamma counter.

EXAMPLE 6

Treatment of a Patient Suffering from Chronic Bronchitis

A 62 year old male suffering from chronic bronchitis ($FEV_1$ reduced to 80% of normal predicted value; daily sputum volume of 30 ml) presents at his GP. Despite treatment with inhaled steroids, the patient presents with difficulty in performing everyday tasks due continued shortness of breath. The GP prescribes a 6-month course of an EGF mutein fusion protein according to the present invention in nebuliser form, 80 μg to be taken monthly. Following discussion with the physician, the patient selects the most appropriate nebuliser for their personal situation from a range of suitable devices. After a single dose of EGF-based fusion protein experiences reduced sputum volume (to 15 ml) and an improvement in FEV1 (to 90%).

EXAMPLE 7

Method for Treating Acromegalic Patients Resistant to Somatostatin Analogues After six years' successful control of circulating GH and IGF-1 by somatostatin analogues (SSA), a 60-year-old acromegalic fairground tarot reader reports increasingly obvious oily skin and also prominent body odour as a result of hyperhydrosis. She is found to be glucose-intolerant and to have elevated circulating IGF-1 levels and raising the SSA dosage does not control these. She is treated by localised injection of an EGF mutein fusion protein according to the present invention. Within 14 days the patient reports a significant reduction in sweating. Over the following month her oily skin returns to normal and at this time her GH and IGF-1 levels are both within the normal range. This situation remains over the next five years.

EXAMPLE 8

Method for Suppressing Neuroendocrine Tumour Cells

A 35 year old male member of a regional badminton team undergoes a spinal X-ray for lower back pain. The consultant notices abnormal bone growth and, on questioning, the man reports increasing incidents of sleep apnoea and also increasingly oily skin. The physician recommends measurement of circulating IGF-1 and these are found to be elevated. Subsequent tests also show above-normal circulating GH levels so a cranial MRI scan is carried out. This shows a pituitary tumour of 9 mm diameter. The patient is treated with an EGF mutein fusion protein of the present invention by injection. At intervals of 1 week circulating IGF-1 levels are measured and are seen to be lower at the first measurement and to reduce steadily to 15% above normal over the following six weeks. The level of circulating GH is found to be normal at this time. A further dose of the medication with two-weekly IGF-1 measurements shows this hormone to have stabilised at the upper end of normal. At six weeks after the second treatment a cranial MRI scan reveals shrinkage of the tumour to 6 mm. The therapy is continued at a reduced dosage at two-monthly intervals with IGF-1 and GH levels measured on the seventh week. These are both stable in the normal range and the sleep apnoea and oily skin are now absent. A spinal X-ray at one year following the first treatment shows no increased bone size from the original observation.

EXAMPLE 9

Comparison of EGF and EGF fusion proteins in an EGF receptor activation assay A431 cells ($1\times10^5$) were incubated with increasing concentrations of EGF, SXN100516 ($LH_N$/A-EGF), SXN100988 ($LH_N$/B-EGF) or SXN100501 ($LH_N$/C-EGF) for 20 min at 37° C.

Cells were washed with ice-cold PBS and lysed. Lysates were diluted 1:10 before the level of phosphorylated ErbB1 receptor was measured using a sandwich immunoassay and MSD platform.

$pEC_{50}$ estimates of Syntaxin molecules at the ErbB1 receptor in A431 cells

| Agonist/SXN Chimaera | $pEC_{50}$ ± s.e.mean |
|---|---|
| EGF per se | 9.13 ± 0.13 |
| SXN100501 fusion protein | 7.15 ± 0.11 |
| SXN100516 fusion protein | 7.47 ± 0.16 |
| SXN100988 fusion protein | 7.61 ± 0.19 |

EXAMPLE 10

Comparison of EGF, EGF Mutein and EGF Mutein Fusion Proteins in an EGF Receptor Activation Assay A431 cells ($1\times10^5$) were incubated with increasing concentrations of Syntaxin EGF mutein fusion or EGF for 20 min at 37° C. in triplicate eppendorf tubes. After washing, the cells were lysed and the lysates added to MSD 96 well plates coated with a capture antibody specific for phosphoY1068 of the EGF receptor.

Following incubation, the plates were washed and incubated with an anti-phospho EGF receptor antibody labeled with an electrochemiluminescent MSD SULFO-TAG. MSD Read buffer was added to the plate and the light emitted from each well of the plate (RLU) measured on the MSD sector imager 6000.

Molecules and Syntaxin Chimaeras Tested

| SXN Number/ligand | Batch | Construct |
|---|---|---|
| SXN101181 | LC080805 | pK7-Hx-EGFv3 |
| SXN101784 | OW090711 | pK7-LcA-XA-HnA-EGFv3-10HT |
| SXN101886 | JW090728B | pK7-6HT-Xa-LC-Xa-HC-GS20-EGFv3N16Y |
| SXN101887 | JW090729 | pK7-6HT-Xa-LC-Xa-HC-GS20-EGFv3L49W |

Results (See FIG. 1)

| Ligand/Chimaera | $pEC_{50}$ |
|---|---|
| EGF | 8.74 ± 0.04 |
| EGFv3 | 7.61 |
| SXN101181 | 8.47 ± 0.08 |
| SXN101784 | 8.13 |
| SXN101886 | 7.04 |
| SXN101887 | 7.69 |

There is no significant difference in the $pEC_{50}$ of SXN101181 compared to EGF ($p>0.05$, t-test).

A log-unit difference in potency ($pEC_{50}$) was observed between EGF (8.74±0.04) and EGFv3 (7.61).

EXAMPLE 11

Treatment of a Patient Suffering from Rhinitis

A 24 years old female who presents annually with typical seasonal allergic rhinitis symptoms is treated by local administration (by nasal spray) with an EGF mutein fusion protein of the present invention. Within 2 to 7 days the patient reports a subsidence of symptoms. The effect is sustained for the remainder of the allergy season.

EXAMPLE 12

Treatment of a Patient Suffering from Asthma

A 43 years old female with a reduced quality of life due to chronic asthma is treated with by systemic injection of an EGF mutein fusion protein of the present invention. Within 3 to 7 days the symptoms of the patient have cleared and the patient can breathe more freely. The effect is sustained for 2 to 3 months, whereupon the treatment is repeated and the improvement to the quality of the patient's life is sustained.

EXAMPLE 13

Treatment of a Patient Suffering from COPD

A 64 years old male with chronic obstructive pulmonary disease who has a reduced quality of life due to inability to breath effectively is treated by local administration (by aerosol) of an EGF mutein fusion protein of the present invention. Within 2 to 5 days the patient has cleared most of the excess airway mucus and can breathe more freely. The effect is sustained for 2 to 3 months, whereupon the treatment is repeated and the improvement to the quality of the patient's life is sustained.

EXAMPLE 14

Treatment of a Patient Suffering from Asthma

A 25 years old male with severe exacerbation of his asthmatic symptoms due to a rhinovirus infection is treated by local administration (inhalation by aerosol) with an EGF mutein fusion protein of the present invention. Within 2 to 7 days the patient reports reduced airway mucus and the exacerbation subsides.

EXAMPLE 15

Treatment of a Patient Suffering from Colon Cancer

A 32 years old male patient with jaundice is diagnosed with advanced hepatocellular carcinoma which has spread to the colon. The patient is treated with a systemic injection of an EGF mutein fusion protein of the present invention. Within two to three weeks the growth of the metastasized tumours has been arrested. Two months after the treatment the tumours have decreased in size and the jaundice has gone. A second application of treatment continues the decrease in tumour size and maintains the alleviation of symptoms.

EXAMPLE 16

Treatment of a Patient Suffering from Psoriasis

A 32 years old male patient diagnosed with psoriasis and who is experiencing significant physical discomfort from itching and scratching the affected areas of his back and arms is treated by topical administration with an EGF mutein fusion protein of the present invention. Within 2 to 7 days the symptoms are relieved and the effect lasts for 1 to 2 months. A second application of treatment maintains the alleviation of symptoms.

EXAMPLE 17

Treatment of a Patient Suffering from Eczema

A 45 years old male patient diagnosed with eczema and who is experiencing significant physical discomfort from itching and scratching the affected areas of his buttocks and legs is treated by topical administration with an EGF mutein fusion protein of the present invention. Within 2 to 7 days the symptoms are relieved and the effect lasts for 1 to 2 months. A second application of treatment maintains the alleviation of symptoms.

EXAMPLE 18

Treatment of a Patient Suffering from Colorectal Cancer

A 70 years old male patient is diagnosed with (stage IV) colorectal cancer. Surgery is not recommended. After treatment with a systemic injection of an EGF mutein fusion protein of the present invention the metastasised tumours have stopped increasing in size. Within one month the tumours have decreased in size and the patient reports feeling better. A second application of treatment further reduces the tumour size and maintains the alleviation of symptoms.

EXAMPLE 19

Treatment of a Patient Suffering from Prostate Cancer

A 46 years old male patient is diagnosed with prostate cancer which has metastasized to the vertebrae. He complains of pains in the spine and pelvis. As surgery is inappropriate the patient is treated with a systemic injection of an EGF mutein fusion protein of the present invention. Within two weeks the tumours have decreased in size and the patient reports less pain. A second application of treatment continues the decrease in tumour size and maintains the alleviation of symptoms.

EXAMPLE 20

Treatment of a Patient Suffering from nsc Lung Cancer

A 46 years old female patient is diagnosed with (stage IV) non-small cell lung carcinoma with a prognosis of 2% chance of living two years. The patient is treated with a systemic injection of an EGF mutein fusion protein of the present invention. Within two weeks the growth rate of the metastasized tumours has been arrested. Two months after the treatment the tumours have decreased in size and the patient feels better. A second application of treatment continues to decrease the tumour size and maintains the alleviation of symptoms. The patient increases her chances of survival beyond two years.

EXAMPLE 21

Treatment of a Patient Suffering from Breast Cancer

A 36 years old female patient with jaundice is diagnosed with advanced breast cancer which has spread to the liver. The patient is treated with a systemic injection of an EGF mutein fusion protein of the present invention. Within two weeks the growth rate of the metastasized tumour has been arrested. Two months after the treatment the tumours have decreased in size and the jaundice has gone. A second application of treatment continues the decrease in tumour size and maintains the alleviation of symptoms.

SEQ ID NOS

SEQ ID 1 Amino acid sequence for naturally-occurring, human epidermal growth factor (EGF)

NSDSECPLSHDGYCLHDGVCMYIEALDKYACNCVVGYIGERCQYRDLKWWELR

-continued

| SEQ ID NOS |
|---|
| SEQ ID 2 DNA sequence of LHA<br>ATGGAGTTCGTTAACAAACAGTTCAACTATAAAGACCCAGTTAACGGTGTTGACATTGCTT<br>ACATCAAAATCCCGAACGCTGGCCAGATGCAGCCGGTAAAGGCATTCAAAATCCACAACA<br>AAATCTGGGTTATCCCGGAACGTGATACCTTTACTAACCCGGAAGAAGGTGACCTGAACC<br>CGCCACCGGAAGCGAAACAGGTGCCGGTATCTTACTATGACTCCACCTACCTGTCTACC<br>GATAACGAAAAGGACAACTACCTGAAAGGTGTTACTAAACTGTTCGAGCGTATTTACTCC<br>ACCGACCTGGGCCGTATGCTGCTGACTAGCATCGTTCGCGGTATCCCGTTCTGGGGCGG<br>TTCTACCATCGATACCGAACTGAAAGTAATCGACACTAACTGCATCAACGTTATTCAGCCG<br>GACGGTTCCTATCGTTCCGAAGAACTGAACCTGGTGATCATCGGCCCGTCTGCTGATATC<br>ATCCAGTTCGAGTGTCTGAGCTTTGGTCACGAAGTTCTGAACCTCACCCGTAACGGCTAC<br>GGTTCCACTCAGTACATCCGTTTCTCTCCGGACTTCACCTTCGGTTTTGAAGAATCCCTG<br>GAAGTAGACACGAACCCACTGCTGGGCGCTGGTAAATTCGCAACTGATCCTGCGGTTAC<br>CCTGGCTCACGAACTGATTCATGCAGGCCACCGCCTGTACGGTATCGCCATCAATCCGA<br>ACCGTGTCTTCAAAGTTAACACCAACGCGTATTACGAGATGTCCGGTCTGGAAGTTAGCT<br>TCGAAGAACTGCGTACTTTTGGCGGTCACGACGCTAAATTCATCGACTCTCTGCAAGAAA<br>ACGAGTTCCGTCTGTACTACTATAACAAGTTCAAAGATATCGCATCCACCCTGAACAAAGC<br>GAAATCCATCGTGGGTACCACTGCTTCTCTCCAGTACATGAAGAACGTTTTTAAAGAAAAA<br>TACCTGCTCAGCGAAGACACCTCCGGCAAATTCTCTGTAGACAAGTTGAAATTCGATAAA<br>CTTTACAAAATGCTGACTGAAATTTACACCGAAGACAACTTCGTTAAGTTCTTTAAAGTTCT<br>GAACCGCAAAACCTATCTGAACTTCGACAAGGCAGTATTCAAAATCAACATCGTGCCGAA<br>AGTTAACTACACTATCTACGATGGTTTCAACCTGCGTAACACCAACCTGGCTGCTAATTTT<br>AACGGCCAGAACACGGAAATCAACAACATGAACTTCACAAAACTGAAAAACTTCACTGGT<br>CTGTTCGAGTTTTACAAGCTGCTGTGCGTCGACGGCATCATTACCTCCAAAACTAAATCT<br>GACGATGACGATAAAAACAAAGCGCTGAACCTGCAGTGTATCAAGGTTAACAACTGGGAT<br>TTATTCTTCAGCCCGAGTGAAGACAACTTCACCAACGACCTGAACAAAGGTGAAGAAATC<br>ACCTCAGATACTAACATCGAAGCAGCCGAAGAAAACATCTCGCTGGACCTGATCCAGCAG<br>TACTACCTGACCTTTAATTTCGACAACGAGCCGGAAAACATTTCTATCGAAAACCTGAGCT<br>CTGATATCATCGGCCAGCTGGAACTGATGCCGAACATCGAACGTTTCCCAAACGGTAAAA<br>AGTACGAGCTGGACAAATATACCATGTTCCACTACCTGCGCGCGCAGGAATTTGAACACG<br>GCAAATCCCGTATCGCACTGACTAACTCCGTTAACGAAGCTCTGCTCAACCCGTCCCGTG<br>TATACACCTTCTTCTCTAGCGACTACGTGAAAAAGGTCAACAAAGCGACTGAAGCTGCAA<br>TGTTCTTGGGTTGGGTTGAACAGCTTGTTTATGATTTTACCGACGAGACGTCCGAAGTAT<br>CTACTACCGACAAAATTGCGGATATCACTATCATCATCCCGTACATCGGTCCGGCTCTGA<br>ACATTGGCAACATGCTGTACAAAGACGACTTCGTTGGCGCACTGATCTTCTCCGGTGCG<br>GTGATCCTGCTGGAGTTCATCCCGGAAATCGCCATCCCGGTACTGGGCACCTTTGCTCT<br>GGTTTCTTACATTGCAAACAAGGTTCTGACTGTACAAACCATCGACAACGCGCTGAGCAA<br>ACGTAACGAAAAATGGGATGAAGTTTACAAATATATCGTGACCAACTGGCTGGCTAAGGT<br>TAATACTCAGATCGACCTCATCCGCAAAAAAATGAAAGAAGCACTGGAAAACCAGGCGGA<br>AGCTACCAAGGCAATCATTAACTACCAGTACAACCAGTACACCGAGGAAGAAAAAAACAA<br>CATCAACTTCAACATCGACGATCTGTCCTCTAAACTGAACGAATCCATCAACAAAGCTATG<br>ATCAACATCAACAAGTTCCTGAACCAGTGCTCTGTAAGCTATCTGATGAACTCCATGATCC<br>CGTACGGTGTTAAACGTCTGGAGGACTTCGATGCGTCTCTGAAAGACGCCCTGCTGAAA<br>TACATTTACGACAACCGTGGCACTCTGATCGGTCAGGTTGATCGTCTGAAGGACAAAGTG<br>AACAATACCTTATCGACCGACATCCCTTTTCAGCTCAGTAAATATGTCGATAACCAACGCC<br>TTTTGTCCACT<br><br>SEQ ID 3 DNA sequence of LHB<br>ATGCCGGTTACCATCAACAACTTCAACTACAACGACCCGATCGACAACAACAACATCATTA<br>TGATGGAACCGCCGTTCGCACGTGGTACCGGACGTTACTACAAGGCTTTTAAGATCACC<br>GACCGTATCTGGATCATCCCGGAACGTTACACCTTCGGTTACAAACCTGAGGACTTCAAC<br>AAGAGTAGCGGGATTTTCAATCGTGACGTCTGCGAGTACTATGATCCAGATTATCTGAAT<br>ACCAACGATAAGAAGAACATATTCCTTCAGACTATGATTAAACTCTTCAACCGTATCAAAA<br>GCAAACCGCTCGGTGAAAAACTCCTCGAAATGATTATCAACGGTATCCCGTACCTCGGTG<br>ACCGTCGTGTCCCGCTTGAAGAGTTCAACACCAACATCGCAAGCGTCACCGTCAACAAAC<br>TCATCAGCAACCCAGGTGAAGTCGAACGTAAAAAAGGTATCTTCGCAAACCTCATCATCT<br>TCGGTCCGGGTCCGGTCCTCAACGAAAACGAAACCATCGACATCGGTATCCAGAACCAC<br>TTCGCAAGCCGTGAAGGTTTCGGTGGTATCATGCAGATGAAATTCTGCCCGGAATACGTC<br>AGTGTCTTCAACAACGTCCAGGAAAACAAAGGTGCAAGCATCTTCAACCGTCGTGGTTAC<br>TTCAGCGACCCGGCACTCATCCTCATGCATGAACTCATCCACGTCCTCCACGGTCTCTAC<br>GGTATCAAAGTTGACGACCTCCCGATCGTCCCGAACGAGAAGAAATTCTTCATGCAGAGC<br>ACCGACGCAATCCAGGCTGAGGAACTCTACACCTTCGGTGGCCAAGACCCAAGTATCAT<br>AACCCCGTCCACCGACAAAAGCATCTACGACAAAGTCCTCCAGAACTTCAGGGGTATCGT<br>GGACAGACTCAACAAAGTCCTCGTCTGCATCAGCGACCCGAACATCAATATCAACATATA<br>CAAGAACAAGTTCAAAGACAAGTACAAATTCGTCGAGGACAGCGAAGGCAAATACAGCAT<br>CGACGTAGAAAGTTTCGACAAGCTCTACAAAAGCCTCATGTTCGGTTTCACCGAAACCAA<br>CATCGCCGAGAACTACAAGATCAAGACAAGGGCAAGTTACTTCAGCGACAGCCTCCCGC<br>CTGTCAAAATCAAGAACCTCTTAGACAACGAGATTTACACAATTGAAGAGGGCTTCAACAT<br>CAGTGACAAAGACATGGAGAAGGAATACAGAGGTCAGAACAAGGCTATCAACAAACAGG<br>CATACGAGGAGATCAGCAAAGAACACCTCGCAGTCTACAAGATCCAGATGTGCGTCGAC<br>GGCATCATTACCTCCAAAACTAAATCTGACGATGACGATAAAAACAAAGCGCTGAACCTG<br>CAGTGCATCGACGTTGACAACGAAGACCTGTTCTTCATCGCTGACAAAAACAGCTTCAGT<br>GACGACCTGAGCAAAAACGAACGTATCGAATACAACACCCAGAGCAACTACATCGAAAAC<br>GACTTCCCGATCAACGAACTGATCCTGGACACCGACCTGATAAGTAAAATCGAACTGCCG<br>AGCGAAAACACCGAAAGTCTGACCGACTTCAACGTTGACGTTCCGGTTTACGAAAAACAG<br>CCGGCTATCAAGAAAATCTTCACCGACGAAAACACCATCTTCCAGTACCTGTACAGCCAG<br>ACCTTCCCGCTGGACATCCGTGACATCAGTCTGACCAGCAGTTTCGACGACGCTCTGCT<br>GTTCAGCAACAAAGTTTACAGTTTCTTCAGCATGGACTACATCAAAACCGCTAACAAAGTT<br>GTTGAAGCAGGGCTGTTCGCTGGTTGGGTTAAACAGATCGTTAACGACTTCGTTATCGAA |

-continued

SEQ ID NOS

GCTAACAAAAGCAACACTATGGACAAAATCGCTGACATCAGTCTGATCGTTCCGTACATC
GGTCTGGCTCTGAACGTTGGTAACGAAACCGCTAAAGGTAACTTTGAAAACGCTTTCGAG
ATCGCTGGTGCAAGCATCCTGCTGGAGTTCATCCCGGAACTGCTGATCCCGGTTGTTGG
TGCTTTCCTGCTGGAAAGTTACATCGACAACAAAAACAAGATCATCAAAACCATCGACAAC
GCTCTGACCAAACGTAACGAAAAATGGAGTGATATGTACGGTCTGATCGTTGCTCAGTGG
CTGAGCACCGTCAACACCCAGTTCTACACCATCAAAGAAGGTATGTACAAAGCTCTGAAC
TACCAGGCTCAGGCTCTGGAAGAGATCATCAAATACCGTTACAACATCTACAGTGAGAAG
GAAAAGAGTAACATCAACATCGACTTCAACGACATCAACAGCAAACTGAACGAAGGTATC
AACCAGGCTATCGACAACATCAACAACTTCATCAACGGTTGCAGTGTTAGCTACCTGATG
AAGAAGATGATCCCGCTGGCTGTTGAAAAACTGCTGGACTTCGACAACACCCTGAAAAAG
AACCTGCTGAACTACATCGACGAAAACAAGCTGTACCTGATCGGTAGTGCTGAATACGAA
AAAAGTAAAGTGAACAAATACCTGAAGACCATCATGCCGTTCGACCTGAGTATCTACACC
AACGACACCATCCTGATCGAAATGTTCAACAAATACAACTCT

SEQ ID 4 DNA sequence of LHC
ATGACGTGGCCAGTTAAGGATTTCAACTACTCAGATCCTGTAAATGACAACGATATTCTGT
ACCTTCGCATTCCACAAAATAAACTGATCACCACACCAGTCAAAGCATTCATGATTACTCA
AAACATTTGGGTCATTCCAGAACGCTTTTCTAGTGACACAAATCCGAGTTTATCTAAACCT
CCGCGTCCGACGTCCAAATATCAGAGCTATTACGATCCCTCATATCTCAGTACGGACGAA
CAAAAAGATACTTTCCTTAAAGGTATCATTAAACTGTTTAAGCGTATTAATGAGCGCGATA
TCGGGAAAAAGTTGATTAATTATCTTGTTGTGGGTTCCCCGTTCATGGGCGATAGCTCTA
CCCCCGAAGACACTTTTGATTTTACCCGTCATACGACAAACATCGCGGTAGAGAAGTTTG
AGAACGGATCGTGGAAAGTCACAAACATCATTACACCTAGCGTCTTAATTTTTGGTCCGC
TGCCAAACATCTTAGATTATACAGCCAGCCTGACTTTGCAGGGGCAACAGTCGAATCCGA
GTTTCGAAGGTTTTGGTACCCTGAGCATTCTGAAAGTTGCCCCGGAATTTCTGCTCACTT
TTTCAGATGTCACCAGCAACCAGAGCTCAGCAGTATTAGGAAAGTCAATTTTTTGCATGG
ACCCGGTTATTGCACTGATGCACGAACTGACGCACTCTCTGCATCAACTGTATGGGATCA
ACATCCCCAGTGACAAACGTATTCGTCCCCAGGTGTCTGAAGGATTTTTCTCACAGGATG
GGCCGAACGTCCAGTTCGAAGAGTTGTATACTTTCGGAGGCCTGGACGTAGAGATCATT
CCCCAGATTGAGCGCAGTCAGCTGCGTGAGAAGGCATTGGGCCATTATAAGGATATTGC
AAAACGCCTGAATAACATTAACAAAACGATTCCATCTTCGTGGATCTCGAATATTGATAAA
TATAAGAAAATTTTTAGCGAGAAATATAATTTTGATAAAGATAATACAGGTAACTTTGTGGT
TAACATTGACAAATTCAACTCCCTTTACAGTGATTTGACGAATGTAATGAGCGAAGTTGTG
TATAGTTCCCAATACAACGTTAAGAATCGTACCCATTACTTCTCTCGTCACTACCTGCCGG
TTTTCGCGAACATCCTTGACGATAATATTTACACTATTCGTGACGGCTTTAACTTGACCAA
CAAGGGCTTCAATATTGAAAATTCAGGCCAGAACATTGAACGCAACCCGGCCTTGCAGAA
ACTGTCGAGTGAATCCGTGGTTGACCTGTTTACCAAAGTCTGCGTCGACAAAAGCGAAGA
GAAGCTGTACGATGACGATGACAAAGATCGTTGGGGATCGTCCCTGCAGTGTATTAAAGT
GAAAAACAATCGGCTGCCTTATGTAGCAGATAAAGATAGCATTAGTCAGGAGATTTTCGA
AAATAAAATTATCACTGACGAAACCAATGTTCAGAATTATTCAGATAAATTTTCACTGGACG
AAAGCATCTTAGATGGCCAAGTTCCGATTAACCCGGAAATTGTTGATCCGTTACTGCCGA
ACGTGAATATGGAACCGTTAAACCTCCCTGGCGAAGAGATCGTATTTTATGATGACATTA
CGAAATATGTGGACTACCTTAATTCTTATTACTATTTGGAAAGCCAGAAACTGTCCAATAA
CGTGGAAAACATTACTCTGACCACAAGCGTGGAAGAGGCTTTAGGCTACTCAAATAAGAT
TTATACCTTCCTCCCGTCGCTGGCGGAAAAAGTAAATAAAGGTGTGCAGGCTGGTCTGTT
CCTCAACTGGGCGAATGAAGTTGTCGAAGACTTTACCACGAATATTATGAAAAAGGATAC
CCTGGATAAAATCTCCGACGTCTCGGTTATTATCCCATATATTGGCCCTGCGTTAAATATC
GGTAATAGTGCGCTGCGGGGGAATTTTAACCAGGCCTTTGCTACCGCGGGCGTCGCGTT
CCTCCTGGAGGGCTTTCCTGAATTTACTATCCCGGCGCTCGGTGTTTTTACATTTTACTCT
TCCATCCAGGAGCGTGAGAAAATTATCAAAACCATCGAAAACTGCCTGGAGCAGCGGGT
GAAACGCTGGAAAGATTCTTATCAATGGATGGTGTCAAACTGGTTATCTCGCATCACGAC
CCAATTCAACCATATTAATTACCAGATGTATGATAGTCTGTCGTACCAAGCTGACGCCATT
AAAGCCAAAATTGATCTGGAATATAAAAAGTACTCTGGTAGCGATAAGGAGAACATCAAAA
GCCAGGTGGAGAACCTTAAGAATAGTCTGGATGTGAAAATCTCTGAAGCTATGAATAACA
TTAACAAATTCATTCGTGAATGTTCGGTGACGTACCTGTTCAAGAATATGCTGCCAAAAGT
TATTGATGAACTGAATAAATTTGATCTGCGTACCAAAACCGAACTTATCAACCTCATCGAC
TCCCACAACATTATCCTTGTGGGCGAAGTGGATCGTCTGAAGGCCAAAGTAAACGAGAG
CTTTGAAAATACGATGCCGTTTAATATTTTTTCATATACCAATAACTCCTTGCTGAAAGATA
TCATCAATGAATATTTCAAT SEQ ID 5 DNA sequence of LHD
ATGACGTGGCCAGTTAAGGATTTCAACTACTCAGATCCTGTAAATGACAACGATATTCTGT
ACCTTCGCATTCCACAAAATAAACTGATCACCACACCAGTCAAAGCATTCATGATTACTCA
AAACATTTGGGTCATTCCAGAACGCTTTTCTAGTGACACAAATCCGAGTTTATCTAAACCT
CCGCGTCCGACGTCCAAATATCAGAGCTATTACGATCCCTCATATCTCAGTACGGACGAA
CAAAAAGATACTTTCCTTAAAGGTATCATTAAACTGTTTAAGCGTATTAATGAGCGCGATA
TCGGGAAAAAGTTGATTAATTATCTTGTTGTGGGTTCCCCGTTCATGGGCGATAGCTCTA
CCCCCGAAGACACTTTTGATTTTACCCGTCATACGACAAACATCGCGGTAGAGAAGTTTG
AGAACGGATCGTGGAAAGTCACAAACATCATTACACCTAGCGTCTTAATTTTTGGTCCGC
TGCCAAACATCTTAGATTATACAGCCAGCCTGACTTTGCAGGGGCAACAGTCGAATCCGA
GTTTCGAAGGTTTTGGTACCCTGAGCATTCTGAAAGTTGCCCCGGAATTTCTGCTCACTT
TTTCAGATGTCACCAGCAACCAGAGCTCAGCAGTATTAGGAAAGTCAATTTTTTGCATGG
ACCCGGTTATTGCACTGATGCACGAACTGACGCACTCTCTGCATCAACTGTATGGGATCA
ACATCCCCAGTGACAAACGTATTCGTCCCCAGGTGTCTGAAGGATTTTTCTCACAGGATG
GGCCGAACGTCCAGTTCGAAGAGTTGTATACTTTCGGAGGCCTGGACGTAGAGATCATT
CCCCAGATTGAGCGCAGTCAGCTGCGTGAGAAGGCATTGGGCCATTATAAGGATATTGC
AAAACGCCTGAATAACATTAACAAAACGATTCCATCTTCGTGGATCTCGAATATTGATAAA
TATAAGAAAATTTTTAGCGAGAAATATAATTTTGATAAAGATAATACAGGTAACTTTGTGGT -continued

| SEQ ID NOS |
|---|

TAACATTGACAAATTCAACTCCCTTTACAGTGATTTGACGAATGTAATGAGCGAAGTTGTG
TATAGTTCCCAATACAACGTTAAGAATCGTACCCATTACTTCTCTCGTCACTACCTGCCGG
TTTTCGCGAACATCCTTGACGATAATATTTACACTATTCGTGACGGCTTTAACTTGACCAA
CAAGGGCTTCAATATTGAAAATTCAGGCCAGAACATTGAACGCAACCCGGCCTTGCAGAA
ACTGTCGAGTGAATCCGTGGTTGACCTGTTTACCAAAGTCTGCGTCGACAAAAGCGAAGA
GAAGCTGTACGATGACGATGACAAAGATCGTTGGGGATCGTCCCTGCAGTGTATTAAAGT
GAAAAACAATCGGCTGCCTTATGTAGCAGATAAAGATAGCATTAGTCAGGAGATTTTCGA
AAATAAAATTATCACTGACGAAACCAATGTTCAGAATTATTCAGATAAATTTTCACTGGACG
AAAGCATCTTAGATGGCCAAGTTCCGATTAACCCGGAAATTGTTGATCCGTTACTGCCGA
ACGTGAATATGGAACCGTTAAACCTCCCTGGCGAAGAGATCGTATTTTATGATGACATTA
CGAAATATGTGGACTACCTTAATTCTTATTACTATTTGGAAAGCCAGAAACTGTCCAATAA
CGTGGAAAACATTACTCTGACCACAAGCGTGGAAGAGGCTTTAGGCTACTCAAATAAGAT
TTATACCTTCCTCCCGTCGCTGGCGGAAAAAGTAAATAAAGGTGTGCAGGCTGGTCTGTT
CCTCAACTGGGCGAATGAAGTTGTCGAAGACTTTACCACGAATATTATGAAAAAGGATAC
CCTGGATAAAATCTCCGACGTCTCGGTTATTATCCCATATATTGGCCCTGCGTTAAATATC
GGTAATAGTGCGCTGCGGGGGAATTTTAACCAGGCCTTTGCTACCGCGGGCGTCGCGTT
CCTCCTGGAGGGCTTTCCTGAATTTACTATCCCGGCGCTCGGTGTTTTTACATTTTACTCT
TCCATCCAGGAGCGTGAGAAAATTATCAAAACCATCGAAAACTGCCTGGAGCAGCGGGT
GAAACGCTGGAAAGATTCTTATCAATGGATGGTGTCAAACTGGTTATCTCGCATCACGAC
CCAATTCAACCATATTAATTACCAGATGTATGATAGTCTGTCGTACCAAGCTGACGCCATT
AAAGCCAAAATTGATCTGGAATATAAAAAGTACTCTGGTAGCGATAAGGAGAACATCAAAA
GCCAGGTGGAGAACCTTAAGAATAGTCTGGATGTGAAAATCTCTGAAGCTATGAATAACA
TTAACAAATTCATTCGTGAATGTTCGGTGACGTACCTGTTCAAGAATATGCTGCCAAAAGT
TATTGATGAACTGAATAAATTTGATCTGCGTACCAAAACCGAACTTATCAACCTCATCGAC
TCCCACAACATTATCCTTGTGGGCGAAGTGGATCGTCTGAAGGCCAAAGTAAACGAGAG
CTTTGAAAATACGATGCCGTTTAATATTTTTTCATATACCAATAACTCCTTGCTGAAAGATA
TCATCAATGAATATTTCAAT

SEQ ID6 EGFH16N
NSDSECPLSHDGYCLNDGVCMYIEALDKYACNCVVGYIGERCQYRDLKWWELR

SEQ ID7 Protein sequence of a EGF variant targeting moiety v1
NSDSECPLSHDGYCLHGGVCMYIKAVDRYACNCVVGYIGERCQYRDLTWWGPR

SEQ ID8 EGFH16Q
NSDSECPLSHDGYCLQDGVCMYIEALDKYACNCVVGYIGERCQYRDLKWWELR

SEQ ID9 Protein sequence of a EGF variant targeting moiety v2
SRGSKCPPSHDGYCLQGGVCMYIEALDRYACNCVVGYAGERCQYRDLTWWGRR

SEQ ID10 EGFW49L
NSDSECPLSHDGYCLHDGVCMYIEALDKYACNCVVGYIGERCQYRDLKLWELR

SEQ ID11 Protein sequence of a EGF variant targeting moiety v3
NSDPKCPLSHEGYCLNDGVCMYIGTLDRYACNCVVGYVGERCQYRDLKLAELR

SEQ ID12 EGFW49I
NSDSECPLSHDGYCLHDGVCMYIEALDKYACNCVVGYIGERCQYRDLKIWELR

SEQ ID13 Protein sequence of a EGF variant targeting moiety v4
NSYSECPPSYDGYCLHDGVCRYIEALDSYACNCVVGYAGERCQYRDLRWWGRR

SEQ ID14 EGFW49V
NSDSECPLSHDGYCLHDGVCMYIEALDKYACNCVVGYIGERCQYRDLKVWELR

SEQ ID15 Protein sequence of a EGF variant targeting moiety v5
NSDSGCPSFHDGYCLNGGVCMYIEALDKYACNCVIGYNGDRCQTRDLKWWELR

SEQ ID16 EGFW49A
NSDSECPLSHDGYCLHDGVCMYIEALDKYACNCVVGYIGERCQYRDLKAWELR

SEQ ID17 Protein sequence of a EGF variant targeting moiety v6 (G12Q)
NSDSECPLSHDQYCLHDGVCMYIEALDKYACNCVVGYIGERCQYRDLKWWELR

SEQ ID18 EGFW49G
NSDSECPLSHDGYCLHDGVCMYIEALDKYACNCVVGYIGERCQYRDLKGWELR

SEQ ID19 Protein sequence of a EGF variant targeting moiety v7 (H16D)
NSDSECPLSHDGYCLDDGVCMYIEALDKYACNCVVGYIGERCQYRDLKWWELR

SEQ ID20 EGFW49S
NSDSECPLSHDGYCLHDGVCMYIEALDKYACNCVVGYIGERCQYRDLKSWELR

SEQ ID21 Protein sequence of a EGF variant targeting moiety v8 (Y13W)
NSDSECPLSHDGWCLHDGVCMYIEALDKYACNCVVGYIGERCQYRDLKWWELR

SEQ ID22 EGFW49T
NSDSECPLSHDGYCLHDGVCMYIEALDKYACNCVVGYIGERCQYRDLKTWELR

-continued

| SEQ ID NOS |
|---|

SEQ ID23 Protein sequence of a EGF variant targeting moiety v9 (Q43A)
NSDSECPLSHDGYCLHDGVCMYIEALDKYACNCVVGYIGERCAYRDLKWWELR

SEQ ID24 EGFW49N
NSDSECPLSHDGYCLHDGVCMYIEALDKYACNCVVGYIGERCQYRDLKNWELR

SEQ ID25 Protein sequence of a EGF variant targeting moiety v10 (H16A)
NSDSECPLSHDGYCLADGVCMYIEALDKYACNCVVGYIGERCQYRDLKWWELR

SEQ ID26 EGF_W49Q
NSDSECPLSHDGYCLHDGVCMYIEALDKYACNCVVGYIGERCQYRDLKQWELR

SEQ ID27 Protein sequence of a EGF variant targeting moiety v11 (L15A)
NSDSECPLSHDGYCAHDGVCMYIEALDKYACNCVVGYIGERCQYRDLKWWELR

SEQ ID28 EGF_H16N_W49L
NSDSECPLSHDGYCLNDGVCMYIEALDKYACNCVVGYIGERCQYRDLKLWELR

SEQ ID29 Protein sequence of a EGF variant targeting moiety v12 (V19E)
NSDSECPLSHDGYCLHDGECMYIEALDKYACNCVVGYIGERCQYRDLKWWELR

SEQ ID30 EGF_H16Q_W49L
NSDSECPLSHDGYCLQDGVCMYIEALDKYACNCVVGYIGERCQYRDLKLWELR

SEQ ID31 Protein sequence of a EGF variant targeting moiety v13 (V34D)
NSDSECPLSHDGYCLHDGVCMYIEALDKYACNCDVGYIGERCQYRDLKWWELR

SEQ ID 32 EGF_H16N_W49I
NSDSECPLSHDGYCLNDGVCMYIEALDKYACNCVVGYIGERCQYRDLKIWELR

SEQ ID 33 Protein sequence of LHA-EGFv1 (Xa activation)
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGIITSKTKSIDGRNKALNL
QCIKVNNWDLFFSPSEDNFTNDLNKGEEITSDTNIEAAEENISLDLIQQYYLTFNFDNEPENISI
ENLSSDIIGQLELMPNIERFPNGKKYELDKYTMFHYLRAQEFEHGKSRIALTNSVNEALLNPSR
VYTFFSSDYVKKVNKATEAAMFLGWVEQLVYDFTDETSEVSTTDKIADITIIIPYIGPALNIGNML
YKDDFVGALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLNESINK
AMININKFLNQCSVSYLMNSMIPYGVKRLEDFDASLKDALLKYIYDNRGTLIGQVDRLKDKVNN
TLSTDIPFQLSKYVDNQRLLSTLEGGGGSGGGGSGGGGSALDNSDSECPLSHDQYCLHDGV
CMYIEALDKYACNCVVGYIGERCQYRDLKWWELR

SEQ ID 34 EGF_H16Q_W49I
NSDSECPLSHDGYCLQDGVCMYIEALDKYACNCVVGYIGERCQYRDLKIWELR

SEQ ID 35 Protein sequence of LHA-EGFv2 (Xa activation)
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGIITSKTKSIDGRNKALNL
QCIKVNNWDLFFSPSEDNFTNDLNKGEEITSDTNIEAAEENISLDLIQQYYLTFNFDNEPENISI
ENLSSDIIGQLELMPNIERFPNGKKYELDKYTMFHYLRAQEFEHGKSRIALTNSVNEALLNPSR
VYTFFSSDYVKKVNKATEAAMFLGWVEQLVYDFTDETSEVSTTDKIADITIIIPYIGPALNIGNML
YKDDFVGALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLNESINK
AMININKFLNQCSVSYLMNSMIPYGVKRLEDFDASLKDALLKYIYDNRGTLIGQVDRLKDKVNN
TLSTDIPFQLSKYVDNQRLLSTLEGGGGSGGGGSGGGGSALDSRGSKCPPSHDGYCLQGG
VCMYIEALDRYACNCVVGYAGERCQYRDLTWWGRR

SEQ ID 36 EGF_H16N_W50A
NSDSECPLSHDGYCLNDGVCMYIEALDKYACNCVVGYIGERCQYRDLKWAELR

SEQ ID 37 Protein sequence of LHA-EGFv3 (enhanced mutation
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECLSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY -continued

| SEQ ID NOS |
|---|

DGFNLRNTNLAANFNGQNTEINNMNFTKLKNFTGLFEFYKLLCVDGIITSKTKSDDDDKNKALN
LQCIKVNNWDLFFSPSEDNFTNDLNKGEEITSDTNIEAAEENISLDLIQQYYLTFNFDNEPENISI
ENLSSDIIGQLELMPNIERFPNGKKYELDKYTMFHYLRAQEFEHGKSRIALTNSVNEALLNPSR
VYTFFSSDYVKKVNKATEAAMFLGWVEQLVYDFTDETSEVSTTDKIADITIIIPYIGPALNIGNML
YKDDFVGALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLNESINK
AMININKFLNQCSVSYLMNSMIPYGVKRLEDFDASLKDALLKYIYDNRGTLIGQVDRLKDKVNN
TLSTDIPFQLSKYVDNQRLLSTLEGGGGSGGGGSGGGGSALDNSDPKCPLSHEGYCLNDGV
CMYIGTLDRYACNCVVGYVGERCQYRDLKLAELR

SEQ ID 38 EGF_H16Q_W50A
NSDSECPLSHDGYCLQDGVCMYIEALDKYACNCVVGYIGERCQYRDLKWAELR

SEQ ID 39 Protein sequence of LHA-EGFv4
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGIITSKTKSDDDDKNKALN
LQCIKVNNWDLFFSPSEDNFTNDLNKGEEITSDTNIEAAEENISLDLIQQYYLTFNFDNEPENISI
ENLSSDIIGQLELMPNIERFPNGKKYELDKYTMFHYLRAQEFEHGKSRIALTNSVNEALLNPSR
VYTFFSSDYVKKVNKATEAAMFLGWVEQLVYDFTDETSEVSTTDKIADITIIIPYIGPALNIGNML
YKDDFVGALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLNESINK
AMININKFLNQCSVSYLMNSMIPYGVKRLEDFDASLKDALLKYIYDNRGTLIGQVDRLKDKVNN
TLSTDIPFQLSKYVDNQRLLSTLEGGGGSGGGGSGGGGSALDNSYSECPPSYDGYCLHDGV
CRYIEALDSYACNCVVGYAGERCQYRDLRWWGRR SEQ ID 40 EGF_H16N_W49L_W50A
NSDSECPLSHDGYCLNDGVCMYIEALDKYACNCVVGYIGERCQYRDLKLAELR SEQ ID 41 Protein sequence of LHA-EGFv5
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGIITSKTKSDDDDKNKALN
LQCIKVNNWDLFFSPSEDNFTNDLNKGEEITSDTNIEAAEENISLDLIQQYYLTFNFDNEPENISI
ENLSSDIIGQLELMPNIERFPNGKKYELDKYTMFHYLRAQEFEHGKSRIALTNSVNEALLNPSR
VYTFFSSDYVKKVNKATEAAMFLGWVEQLVYDFTDETSEVSTTDKIADITIIIPYIGPALNIGNML
YKDDFVGALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLNESINK
AMININKFLNQCSVSYLMNSMIPYGVKRLEDFDASLKDALLKYIYDNRGTLIGQVDRLKDKVNN
TLSTDIPFQLSKYVDNQRLLSTLEGGGGSGGGGSGGGGSALDNSDSGCPSFHDGYCLNGG
VCMYIEALDKYACNCVIGYNGDRCQTRDLKWWELR SEQ ID 42 EGF_H16Q_W49L_W50A
NSDSECPLSHDGYCLQDGVCMYIEALDKYACNCVVGYIGERCQYRDLKLAELR SEQ ID 43 Protein sequence of LHA-EGFv6
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGIITSKTKSDDDDKNKALN
LQCIKVNNWDLFFSPSEDNFTNDLNKGEEITSDTNIEAAEENISLDLIQQYYLTFNFDNEPENISI
ENLSSDIIGQLELMPNIERFPNGKKYELDKYTMFHYLRAQEFEHGKSRIALTNSVNEALLNPSR
VYTFFSSDYVKKVNKATEAAMFLGWVEQLVYDFTDETSEVSTTDKIADITIIIPYIGPALNIGNML
YKDDFVGALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLNESINK
AMININKFLNQCSVSYLMNSMIPYGVKRLEDFDASLKDALLKYIYDNRGTLIGQVDRLKDKVNN
TLSTDIPFQLSKYVDNQRLLSTLEGGGGSGGGGSGGGGSALDNSDSECPLSHDQYCLHDGV
CMYIEALDKYACNCVVGYIGERCQYRDLKWWELR SEQ ID 44 EGF_H16N_W49I_W50A
NSDSECPLSHDGYCLNDGVCMYIEALDKYACNCVVGYIGERCQYRDLKIAELR SEQ ID 45 Protein sequence of LHC-EGFv7
MPITINNFNYSDPVDNKNILYLDTHLNTLANEPEKAFRITGNIWVIPDRFSRNSNPNLNKPPRVT
SPKSGYYDPNYLSTDSDKDTFLKEIIKLFKRINSREIGEELIYRLSTDIPFPGNNNTPINTFDFDV
DFNSVDVKTRQGNNWVKTGSINPSVIITGPRENIIDPETSTFKLTNNTFAAQEGFGALSIISISP
RFMLTYSNATNDVGEGRFSKSEFCMDPILILMHELNHAMHNLYGIAIPNDQTISSVTSNIFYSQ -continued

| SEQ ID NOS |
|---|
| YNVKLEYAEIYAFGGPTIDLIPKSARKYFEEKALDYYRSIAKRLNSITTANPSSFNKYIGEYKQKL<br>IRKYRFVVESSGEVTVNRNKFVELYNELTQIFTEFNYAKIYNVQNRKIYLSNVYTPVTANILDDN<br>VYDIQNGFNIPKSNLNVLFMGQNLSRNPALRKVNPENMLYLFTKFCVDADDDDKLYNKTLQCR<br>ELLVKNTDLPFIGDISDVKTDIFLRKDINEETEVIYYPDNVSVDQVILSKNTSEHGQLDLLYPSID<br>SESEILPGENQVFYDNRTQNVDYLNSYYYLESQKLSDNVEDFTFTRSIEEALDNSAKVYTYFP<br>TLANKVNAGVQGGLFLMWANDVVEDFTTNILRKDTLDKISDVSAIIPYIGPALNISNSVRRGNFT<br>EAFAVTGVTILLEAFPEFTIPALGAFVIYSKVQERNEIIKTIDNCLEQRIKRWKDSYEWMMGTW<br>LSRIITQFNNISYQMYDSLNYQAGAIKAKIDLEYKKYSGSDKENIKSQVENLKNSLDVKISEAMN<br>NINKFIRECSVTYLFKNMLPKVIDELNEFDRNTKAKLINLIDSHNIILVGEVDKLKAKVNNSFQNTI<br>PFNIFSYTNNSLLKDIINEYFNLEGGGGSGGGGSGGGGSALDNSDSECPLSHDGYCLDDGVC<br>MYIEALDKYACNCVVGYIGERCQYRDLKWWELR |
| SEQ ID 46 EGF_H16Q_W49I_W50A<br>NSDSECPLSHDGYCLQDGVCMYIEALDKYACNCVVGYIGERCQYRDLKIAELR |
| SEQ ID 47 Protein sequence of LHC-EGFv8<br>MPITINNFNYSDPVDNKNILYLDTHLNTLANEPEKAFRITGNIWVIPDRFSRNSNPNLNKPPRVT<br>SPKSGYYDPNYLSTDSDKDTFLKEIIKLFKRINSREIGEELIYRLSTDIPFPGNNNTPINTFDFDV<br>DFNSVDVKTRQGNNWVKTGSINPSVIITGPRENIIDPETSTFKLTNNTFAAQEGFGALSIISISP<br>RFMLTYSNATNDVGEGRFSKSEFCMDPILILMHELNHAMHNLYGIAIPNDQTISSVTSNIFYSQ<br>YNVKLEYAEIYAFGGPTIDLIPKSARKYFEEKALDYYRSIAKRLNSITTANPSSFNKYIGEYKQKL<br>IRKYRFVVESSGEVTVNRNKFVELYNELTQIFTEFNYAKIYNVQNRKIYLSNVYTPVTANILDDN<br>VYDIQNGFNIPKSNLNVLFMGQNLSRNPALRKVNPENMLYLFTKFCVDADDDDKLYNKTLQCR<br>ELLVKNTDLPFIGDISDVKTDIFLRKDINEETEVIYYPDNVSVDQVILSKNTSEHGQLDLLYPSID<br>SESEILPGENQVFYDNRTQNVDYLNSYYYLESQKLSDNVEDFTFTRSIEEALDNSAKVYTYFP<br>TLANKVNAGVQGGLFLMWANDVVEDFTTNILRKDTLDKISDVSAIIPYIGPALNISNSVRRGNFT<br>EAFAVTGVTILLEAFPEFTIPALGAFVIYSKVQERNEIIKTIDNCLEQRIKRWKDSYEWMMGTW<br>LSRIITQFNNISYQMYDSLNYQAGAIKAKIDLEYKKYSGSDKENIKSQVENLKNSLDVKISEAMN<br>NINKFIRECSVTYLFKNMLPKVIDELNEFDRNTKAKLINLIDSHNIILVGEVDKLKAKVNNSFQNTI<br>PFNIFSYTNNSLLKDIINEYFNLEGGGGSGGGGSGGGGSALDNSDSECPLSHDGYCLDDGVC<br>MYIEALDKYACNCVVGYIGERCQYRDLKWWELR |
| SEQ ID 48 EGF_H16N_W49L_W50A_E24G<br>NSDSECPLSHDGYCLNDGVCMYIGALDKYACNCVVGYIGERCQYRDLKLAELR |
| SEQ ID 49 Protein sequence of LHC-EGFv9<br>MPITINNFNYSDPVDNKNILYLDTHLNTLANEPEKAFRITGNIWVIPDRFSRNSNPNLNKPPRVT<br>SPKSGYYDPNYLSTDSDKDTFLKEIIKLFKRINSREIGEELIYRLSTDIPFPGNNNTPINTFDFDV<br>DFNSVDVKTRQGNNWVKTGSINPSVIITGPRENIIDPETSTFKLTNNTFAAQEGFGALSIISISP<br>RFMLTYSNATNDVGEGRFSKSEFCMDPILILMHELNHAMHNLYGIAIPNDQTISSVTSNIFYSQ<br>YNVKLEYAEIYAFGGPTIDLIPKSARKYFEEKALDYYRSIAKRLNSITTANPSSFNKYIGEYKQKL<br>IRKYRFVVESSGEVTVNRNKFVELYNELTQIFTEFNYAKIYNVQNRKIYLSNVYTPVTANILDDN<br>VYDIQNGFNIPKSNLNVLFMGQNLSRNPALRKVNPENMLYLFTKFCVDADDDDKLYNKTLQCR<br>ELLVKNTDLPFIGDISDVKTDIFLRKDINEETEVIYYPDNVSVDQVILSKNTSEHGQLDLLYPSID<br>SESEILPGENQVFYDNRTQNVDYLNSYYYLESQKLSDNVEDFTFTRSIEEALDNSAKVYTYFP<br>TLANKVNAGVQGGLFLMWANDVVEDFTTNILRKDTLDKISDVSAIIPYIGPALNISNSVRRGNFT<br>EAFAVTGVTILLEAFPEFTIPALGAFVIYSKVQERNEIIKTIDNCLEQRIKRWKDSYEWMMGTW<br>LSRIITQFNNISYQMYDSLNYQAGAIKAKIDLEYKKYSGSDKENIKSQVENLKNSLDVKISEAMN<br>NINKFIRECSVTYLFKNMLPKVIDELNEFDRNTKAKLINLIDSHNIILVGEVDKLKAKVNNSFQNTI<br>PFNIFSYTNNSLLKDIINEYFNLEGGGGSGGGGSGGGGSALDNSDSECPLSHDGYCLHDGVC<br>MYIEALDKYACNCVVGYIGERCAYRDLKWWELR |
| SEQ ID 50 EGF_H16N_W49L_W50A_E24G_A25T<br>NSDSECPLSHDGYCLNDGVCMYIGTLDKYACNCVVGYIGERCQYRDLKLAELR |
| SEQ ID 51 Protein sequence of LHC-EGFv10<br>MPITINNFNYSDPVDNKNILYLDTHLNTLANEPEKAFRITGNIWVIPDRFSRNSNPNLNKPPRVT<br>SPKSGYYDPNYLSTDSDKDTFLKEIIKLFKRINSREIGEELIYRLSTDIPFPGNNNTPINTFDFDV<br>DFNSVDVKTRQGNNWVKTGSINPSVIITGPRENIIDPETSTFKLTNNTFAAQEGFGALSIISISP<br>RFMLTYSNATNDVGEGRFSKSEFCMDPILILMHELNHAMHNLYGIAIPNDQTISSVTSNIFYSQ<br>YNVKLEYAEIYAFGGPTIDLIPKSARKYFEEKALDYYRSIAKRLNSITTANPSSFNKYIGEYKQKL<br>IRKYRFVVESSGEVTVNRNKFVELYNELTQIFTEFNYAKIYNVQNRKIYLSNVYTPVTANILDDN<br>VYDIQNGFNIPKSNLNVLFMGQNLSRNPALRKVNPENMLYLFTKFCVDADDDDKLYNKTLQCR<br>ELLVKNTDLPFIGDISDVKTDIFLRKDINEETEVIYYPDNVSVDQVILSKNTSEHGQLDLLYPSID<br>SESEILPGENQVFYDNRTQNVDYLNSYYYLESQKLSDNVEDFTFTRSIEEALDNSAKVYTYFP<br>TLANKVNAGVQGGLFLMWANDVVEDFTTNILRKDTLDKISDVSAIIPYIGPALNISNSVRRGNFT<br>EAFAVTGVTILLEAFPEFTIPALGAFVIYSKVQERNEIIKTIDNCLEQRIKRWKDSYEWMMGTW<br>LSRIITQFNNISYQMYDSLNYQAGAIKAKIDLEYKKYSGSDKENIKSQVENLKNSLDVKISEAMN<br>NINKFIRECSVTYLFKNMLPKVIDELNEFDRNTKAKLINLIDSHNIILVGEVDKLKAKVNNSFQNTI<br>PFNIFSYTNNSLLKDIINEYFNLEGGGGSGGGGSGGGGSALDNSDSECPLSHDGYCLADGVC<br>MYIEALDKYACNCVVGYIGERCQYRDLKWWELR |
| SEQ ID 52 EGF_H16N_W49L_W50A_E24G_A25S<br>NSDSECPLSHDGYCLNDGVCMYIGSLDKYACNCVVGYIGERCQYRDLKLAELR |
| SEQ ID 53 Protein sequence of LHC-EGFv11<br>MPITINNFNYSDPVDNKNILYLDTHLNTLANEPEKAFRITGNIWVIPDRFSRNSNPNLNKPPRVT<br>SPKSGYYDPNYLSTDSDKDTFLKEIIKLFKRINSREIGEELIYRLSTDIPFPGNNNTPINTFDFDV |

-continued

| SEQ ID NOS |
| --- |

DFNSVDVKTRQGNNWVKTGSINPSVIITGPRENIIDPETSTFKLTNNTFAAQEGFGALSIISISP
RFMLTYSNATNDVGEGRFSKSEFCMDPILILMHELNHAMHNLYGIAIPNDQTISSVTSNIFYSQ
YNVKLEYAEIYAFGGPTIDLIPKSARKYFEEKALDYYRSIAKRLNSITTANPSSFNKYIGEYKQKL
IRKYRFVVESSGEVTVNRNKFVELYNELTQIFTEFNYAKIYNVQNRKIYLSNVYTPVTANILDDN
VYDIQNGFNIPKSNLNVLFMGQNLSRNPALRKVNPENMLYLFTKFCVDADDDDKLYNKTLQCR
ELLVKNTDLPFIGDISDVKTDIFLRKDINEETEVIYYPDNVSVDQVILSKNTSEHGQLDLLYPSID
SESEILPGENQVFYDNRTQNVDYLNSYYYLESQKLSDNVEDFTFTRSIEEALDNSAKVYTYFP
TLANKVNAGVQGGLFLMWANDVVEDFTTNILRKDTLDKISDVSAIIPYIGPALNISNSVRRGNFT
EAFAVTGVTILLEAFPEFTIPALGAFVIYSKVQERNEIIKTIDNCLEQRIKRWKDSYEWMMGTW
LSRIITQFNNISYQMYDSLNYQAGAIKAKIDLEYKKYSGSDKENIKSQVENLKNSLDVKISEAMN
NINKFIRECSVTYLFKNMLPKVIDELNEFDRNTKAKLINLIDSHNIILVGEVDKLKAKVNNSFQNTI
PFNIFSYTNNSLLKDIINEYFNLEGGGGSGGGGSGGGGSALDNSDSECPLSHDGYCAHDGVC
MYIEALDKYACNCVVGYIGERCQYRDLKWWELR

SEQ ID 54 EGF_H16N_W49L_W50A_E24G_A25T_K28R
NSDSECPLSHDGYCLNDGVCMYIGTLDRYACNCVVGYIGERCQYRDLKLAELR

SEQ ID 55 Protein sequence of LHC-EGFv12
MPITINNFNYSDPVDNKNILYLDTHLNTLANEPEKAFRITGNIWVIPDRFSRNSNPNLNKPPRVT
SPKSGYYDPNYLSTDSDKDTFLKEIIKLFKRINSREIGEELIYRLSTDIPFPGNNNTPINTFDFDV
DFNSVDVKTRQGNNWVKTGSINPSVIITGPRENIIDPETSTFKLTNNTFAAQEGFGALSIISISP
RFMLTYSNATNDVGEGRFSKSEFCMDPILILMHELNHAMHNLYGIAIPNDQTISSVTSNIFYSQ
YNVKLEYAEIYAFGGPTIDLIPKSARKYFEEKALDYYRSIAKRLNSITTANPSSFNKYIGEYKQKL
IRKYRFVVESSGEVTVNRNKFVELYNELTQIFTEFNYAKIYNVQNRKIYLSNVYTPVTANILDDN
VYDIQNGFNIPKSNLNVLFMGQNLSRNPALRKVNPENMLYLFTKFCVDADDDDKLYNKTLQCR
ELLVKNTDLPFIGDISDVKTDIFLRKDINEETEVIYYPDNVSVDQVILSKNTSEHGQLDLLYPSID
SESEILPGENQVFYDNRTQNVDYLNSYYYLESQKLSDNVEDFTFTRSIEEALDNSAKVYTYFP
TLANKVNAGVQGGLFLMWANDVVEDFTTNILRKDTLDKISDVSAIIPYIGPALNISNSVRRGNFT
EAFAVTGVTILLEAFPEFTIPALGAFVIYSKVQERNEIIKTIDNCLEQRIKRWKDSYEWMMGTW
LSRIITQFNNISYQMYDSLNYQAGAIKAKIDLEYKKYSGSDKENIKSQVENLKNSLDVKISEAMN
NINKFIRECSVTYLFKNMLPKVIDELNEFDRNTKAKLINLIDSHNIILVGEVDKLKAKVNNSFQNTI
PFNIFSYTNNSLLKDIINEYFNLEGGGGSGGGGSGGGGSALDNSDSECPLSHDGYCLHDGEC
MYIEALDKYACNCVVGYIGERCQYRDLKWWELR SEQ ID 56 EGF_H16N_W49L_W50A_E24G_A25T_K28R_S4P
NSDPECPLSHDGYCLNDGVCMYIGTLDRYACNCVVGYIGERCQYRDLKLAELR SEQ ID 57 Protein sequence of LHC-EGFv13
MPITINNFNYSDPVDNKNILYLDTHLNTLANEPEKAFRITGNIWVIPDRFSRNSNPNLNKPPRVT
SPKSGYYDPNYLSTDSDKDTFLKEIIKLFKRINSREIGEELIYRLSTDIPFPGNNNTPINTFDFDV
DFNSVDVKTRQGNNWVKTGSINPSVIITGPRENIIDPETSTFKLTNNTFAAQEGFGALSIISISP
RFMLTYSNATNDVGEGRFSKSEFCMDPILILMHELNHAMHNLYGIAIPNDQTISSVTSNIFYSQ
YNVKLEYAEIYAFGGPTIDLIPKSARKYFEEKALDYYRSIAKRLNSITTANPSSFNKYIGEYKQKL
IRKYRFVVESSGEVTVNRNKFVELYNELTQIFTEFNYAKIYNVQNRKIYLSNVYTPVTANILDDN
VYDIQNGFNIPKSNLNVLFMGQNLSRNPALRKVNPENMLYLFTKFCVDADDDDKLYNKTLQCR
ELLVKNTDLPFIGDISDVKTDIFLRKDINEETEVIYYPDNVSVDQVILSKNTSEHGQLDLLYPSID
SESEILPGENQVFYDNRTQNVDYLNSYYYLESQKLSDNVEDFTFTRSIEEALDNSAKVYTYFP
TLANKVNAGVQGGLFLMWANDVVEDFTTNILRKDTLDKISDVSAIIPYIGPALNISNSVRRGNFT
EAFAVTGVTILLEAFPEFTIPALGAFVIYSKVQERNEIIKTIDNCLEQRIKRWKDSYEWMMGTW
LSRIITQFNNISYQMYDSLNYQAGAIKAKIDLEYKKYSGSDKENIKSQVENLKNSLDVKISEAMN
NINKFIRECSVTYLFKNMLPKVIDELNEFDRNTKAKLINLIDSHNIILVGEVDKLKAKVNNSFQNTI
PFNIFSYTNNSLLKDIINEYFNLEGGGGSGGGGSGGGGSALDNSDSECPLSHDGYCLHDGVC
MYIEALDKYACNCDVGYIGERCQYRDLKWWELR SEQ ID 58 EGF_H16N_W49L_W50A_E24G_A25T_K28R_S4P_E5K
NSDPKCPLSHDGYCLNDGVCMYIGTLDRYACNCVVGYIGERCQYRDLKLAELR SEQ ID 59 Protein sequence of LHB-EGFv1
MPVTINNFNYNDPIDNNNIIMMEPPFARGTGRYYKAFKITDRIWIIPERYTFGYKPEDFNKSSGI
FNRDVCEYYDPDYLNTNDKKNIFLQTMIKLFNRIKSKPLGEKLLEMIINGIPYLGDRRVPLEEFN
TNIASVTVNKLISNPGEVERKKGIFANLIIFGPGPVLNENETIDIGIQNHFASREGFGGIMQMKF
CPEYVSVFNNVQENKGASIFNRRGYFSDPALILMHELIHVLHGLYGIKVDDLPIVPNEKKFFMQ
STDAIQAEELYTFGGQDPSIITPSTDKSIYDKVLQNFRGIVDRLNKVLVCISDPNININIYKNKFKD
KYKFVEDSEGKYSIDVESFDKLYKSLMFGFTETNIAENYKIKTRASYFSDSLPPVKIKNLLDNEI
YTIEEGFNISDKDMEKEYRGQNKAINKQAYEEISKEHLAVYKIQMCVDEEKLYDDDDKDRWGS
SLQCIDVDNEDLFFIADKNSFSDDLSKNERIEYNTQSNYIENDFPINELILDTDLISKIELPSENTE
SLTDFNVDVPVYEKQPAIKKIFTDENTIFQYLYSQTFPLDIRDISLTSSFDDALLFSNKVYSFFSM
DYIKTANKVVEAGLFAGWVKQIVNDFVIEANKSNTMDAIADISLIVPYIGLALNVGNETAKGNFE
NAFEIAGASILLEFIPELLIPVVGAFLLESYIDNKNKIIKTIDNALTKRNEKWSDMYGLIVAQWLST
VNTQFYTIKEGMYKALNYQAQALEEIIKYRYNIYSEKEKSNINIDFNDINSKLNEGINQAIDNINNF
INGCSVSYLMKKMIPLAVEKLLDFDNTLKKNLLNYIDENKLYLIGSAEYEKSKVNKYLKTIMPFDL
SIYTNDTILIEMFNKYNSLEGGGGSGGGGSGGGGSALDSRGSKCPPSHDGYCLQGGVCMYI
EALDRYACNCVVGYAGERCQYRDLTWWGRR SEQ ID 60 EGFv3
NSDPKCPLSHEGYCLNDGVCMYIGTLDRYACNCVVGYVGERCQYRDLKLAELR -continued

| SEQ ID NOS |
| --- |

SEQ ID 61 Protein sequence of LHB-EGFv5
MPVTINNFNYNDPIDNNNIIMMEPPFARGTGRYYKAFKITDRIWIIPERYTFGYKPEDFNKSSGI
FNRDVCEYYDPDYLNTNDKKNIFLQTMIKLFNRIKSKPLGEKLLEMIINGIPYLGDRRVPLEEFN
TNIASVTVNKLISNPGEVERKKGIFANLIIFGPGPVLNENETIDIGIQNHFASREGFGGIMQMKF
CPEYVSVFNNVQENKGASIFNRRGYFSDPALILMHELIHVLHGLYGIKVDDLPIVPNEKKFFMQ
STDAIQAEELYTFGGQDPSIITPSTDKSIYDKVLQNFRGIVDRLNKVLVCISDPNININIYKNKFKD
KYKFVEDSEGKYSIDVESFDKLYKSLMFGFTETNIAENYKIKTRASYFSDSLPPVKIKNLLDNEI
YTIEEGFNISDKDMEKEYRGQNKAINKQAYEEISKEHLAVYKIQMCVDEEKLYDDDDKDRWGS
SLQCIDVDNEDLFFIADKNSFSDDLSKNERIEYNTQSNYIENDFPINELILDTDLISKIELPSENTE
SLTDFNVDVPVYEKQPAIKKIFTDENTIFQYLYSQTFPLDIRDISLTSSFDDALLFSNKVYSFFSM
DYIKTANKVVEAGLFAGWVKQIVNDFVIEANKSNTMDAIADISLIVPYIGLALNVGNETAKGNFE
NAFEIAGASILLEFIPELLIPVVGAFLLESYIDNKNKIIKTIDNALTKRNEKWSDMYGLIVAQWLST
VNTQFYTIKEGMYKALNYQAQALEEIIKYRYNIYSEKEKSNINIDFNDINSKLNEGINQAIDNINNF
INGCSVSYLMKKMIPLAVEKLLDFDNTLKKNLLNYIDENKLYLIGSAEYEKSKVNKYLKTIMPFDL
SIYTNDTILIEMFNKYNSLEGGGGSGGGGSGGGGSALDNSDSGCPSFHDGYCLNGGVCMYI
EALDKYACNCVIGYNGDRCQTRDLKWWELR SEQ ID 62 Protein sequence of Tetanus LHN-EGFv1
MPITINNFRYSDPVNNDTIIMMEPPYCKGLDIYYKAFKITDRIWIVPERYEFGTKPEDFNPPSSLI
EGASEYYDPNYLRTDSDKDRFLQTMVKLFNRIKNNVAGEALLDKIINAIPYLGNSYSLLDKFDT
NSNSVSFNLLEQDPSGATTKSAMLTNLIIFGPGPVLNKNEVRGIVLRVDNKNYFPCRDGFGSI
MQMAFCPEYVPTFDNVIENITSLTIGKSKYFQDPALLLMHELIHVLHGLYGMQVSSHEIIPSKQE
IYMQHTYPISAEELFTFGGQDANLISIDIKNDLYEKTLNDYKAIANKLSQVTSCNDPNIDIDSYKQ
IYQQKYQFDKDSNGQYIVNEDKFQILYNSIMYGFTEIELGKKFNIKTRLSYFSMNHDPVKIPNLL
DDTIYNDTEGFNIESKDLKSEYKGQNMRVNTNAFRNVDGSGLVSKLIGLCVDGIITSKTKSDDD
DKNKALNLQCIKIKNEDLTFIAEKNSFSEEPFQDEIVSYNTKNKPLNFNYSLDKIIVDYNLQSKITL
PNDRTTPVTKGIPYAPEYKSNAASTIEIHNIDDNTIYQYLYAQKSPTTLQRITMTNSVDDALINST
KIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKA
KWLGTVNTQFQKRSYQMYRSLEYQVDAIKKIIDYEYKIYSGPDKEQIADEINNLKNKLEEKANK
AMININIFMRESSRSFLVNQMINEAKKQLLEFDTQSKNILMQYIKANSKFIGITELKKLESKINKV
FSTPIPFSYSKNLDCWVDNEEDIDVGLEGGGGSGGGGSGGGGSALDNSDSECPLSHDQYCL
HDGVCMYIEALDKYACNCVVGYIGERCQYRDLKWWELR SEQ ID 63 Protein sequence of LHD-EGFv6 (protease sensitivity site)
MTWPVKDFNYSDPVNDNDILYLRIPQNKLITTPVKAFMITQNIWVIPERFSSDTNPSLSKPPRP
TSKYQSYYDPSYLSTDEQKDTFLKGIIKLFKRINERDIGKKLINYLVVGSPFMGDSSTPEDTFDF
TRHTTNIAVEKFENGSWKVTNIITPSVLIFGPLPNILDYTASLTLQGQQSNPSFEGFGTLSILKV
APEFLLTFSDVTSNQSSAVLGKSIFCMDPVIALMHELTHSLHQLYGINIPSDKRIRPQVSEGFFS
LDGRNVQFEELYTFGGLDVEIIPQIERSQLREKALGHYKDIAKRLNNINKTIPSSWISNIDKYKKI
FSEKYNFDKDNTGNFVVNIDKFNSLYSDLTNVMSEVVYSSQYNVKNRTHYFSRHYLPVFANIL
DDNIYTIRDGFNLTNKGFNIENSGQNIERNPALQKLSSESVVDLFTKVCVDKSEEKLYDDDDKD
RWGSSLQCIKVKNNRLPYVADKDSISQEIFENKIITDETNVQNYSDKFSLDESILDGQVPINPEI
VDPLLPNVNMEPLNLPGEEIVFYDDITKYVDYLNSYYYLESQKLSNNVENITLTTSVEEALGYS
NKIYTFLPSLAEKVNKGVQAGLFLNWANEVVEDFTTNIMKKDTLDKISDVSVIIPYIGPALNIGNS
ALRGNFNQAFATAGVAFLLEGFPEFTIPALGVFTFYSSIQEREKIIKTIENCLEQRVKRWKDSY
QWMVSNWLSRITTQFNHINYQMYDSLSYQADAIKAKIDLEYKKYSGSDKENIKSQVENLKNSL
DVKISEAMNNINKFIRECSVTYLFKNMLPKVIDELNKFDLRTKTELINLIDSHNIILVGEVDRLKAK
VNESFENTMPFNIFSYTNNSLLKDIINEYFNLEGGGGSGGGGSGGGGSALDNSDSECPLSHD
QYCLHDGVCMYIEALDKYACNCVVGYIGERCQYRDLKWWELR SEQ ID 64 Protein sequence of LHD-EGFv3
MTWPVKDFNYSDPVNDNDILYLRIPQNKLITTPVKAFMITQNIWVIPERFSSDTNPSLSKPPRP
TSKYQSYYDPSYLSTDEQKDTFLKGIIKLFKRINERDIGKKLINYLVVGSPFMGDSSTPEDTFDF
TRHTTNIAVEKFENGSWKVTNIITPSVLIFGPLPNILDYTASLTLQGQQSNPSFEGFGTLSILKV
APEFLLTFSDVTSNQSSAVLGKSIFCMDPVIALMHELTHSLHQLYGINIPSDKRIRPQVSEGFFS
LDGRNVQFEELYTFGGLDVEIIPQIERSQLREKALGHYKDIAKRLNNINKTIPSSWISNIDKYKKI
FSEKYNFDKDNTGNFVVNIDKFNSLYSDLTNVMSEVVYSSQYNVKNRTHYFSRHYLPVFANIL
DDNIYTIRDGFNLTNKGFNIENSGQNIERNPALQKLSSESVVDLFTKVCVDKSEEKLYDDDDKD
RWGSSLQCIKVKNNRLPYVADKDSISQEIFENKIITDETNVQNYSDKFSLDESILDGQVPINPEI
VDPLLPNVNMEPLNLPGEEIVFYDDITKYVDYLNSYYYLESQKLSNNVENITLTTSVEEALGYS
NKIYTFLPSLAEKVNKGVQAGLFLNWANEVVEDFTTNIMKKDTLDKISDVSVIIPYIGPALNIGNS
ALRGNFNQAFATAGVAFLLEGFPEFTIPALGVFTFYSSIQEREKIIKTIENCLEQRVKRWKDSY
QWMVSNWLSRITTQFNHINYQMYDSLSYQADAIKAKIDLEYKKYSGSDKENIKSQVENLKNSL
DVKISEAMNNINKFIRECSVTYLFKNMLPKVIDELNKFDLRTKTELINLIDSHNIILVGEVDRLKAK
VNESFENTMPFNIFSYTNNSLLKDIINEYFNLEGGGGSGGGGSGGGGSALDNSDPKCPLSHE
GYCLNDGVCMYIGTLDRYACNCVVGYVGERCQYRDLKLAELR SEQ ID 65 Protein sequence of LHD-EGFv11
MTWPVKDFNYSDPVNDNDILYLRIPQNKLITTPVKAFMITQNIWVIPERFSSDTNPSLSKPPRP
TSKYQSYYDPSYLSTDEQKDTFLKGIIKLFKRINERDIGKKLINYLVVGSPFMGDSSTPEDTFDF
TRHTTNIAVEKFENGSWKVTNIITPSVLIFGPLPNILDYTASLTLQGQQSNPSFEGFGTLSILKV
APEFLLTFSDVTSNQSSAVLGKSIFCMDPVIALMHELTHSLHQLYGINIPSDKRIRPQVSEGFFS
QDGPNVQFEELYTFGGLDVEIIPQIERSQLREKALGHYKDIAKRLNNINKTIPSSWISNIDKYKKI
FSEKYNFDKDNTGNFVVNIDKFNSLYSDLTNVMSEVVYSSQYNVKNRTHYFSRHYLPVFANIL
DDNIYTIRDGFNLTNKGFNIENSGQNIERNPALQKLSSESVVDLFTKVCVDKSEEKLYDDDDKD
RWGSSLQCIKVKNNRLPYVADKDSISQEIFENKIITDETNVQNYSDKFSLDESILDGQVPINPEI
VDPLLPNVNMEPLNLPGEEIVFYDDITKYVDYLNSYYYLESQKLSNNVENITLTTSVEEALGYS -continued

| SEQ ID NOS |
| --- |

NKIYTFLPSLAEKVNKGVQAGLFLNWANEVVEDFTTNIMKKDTLDKISDVSVIIPYIGPALNIGNS
ALRGNFNQAFATAGVAFLLEGFPEFTIPALGVFTFYSSIQEREKIIKTIENCLEQRVKRWKDSY
QWMVSNWLSRITTQFNHINYQMYDSLSYQADAIKAKIDLEYKKYSGSDKENIKSQVENLKNSL
DVKISEAMNNINKFIRECSVTYLFKNMLPKVIDELNKFDLRTKTELINLIDSHNIILVGEVDRLKAK
VNESFENTMPFNIFSYTNNSLLKDIINEYFNLEGGGGSGGGGSGGGGSALDNSDSECPLSHD
GYCLDDGVCMYIEALDKYACNCVVGYIGERCQYRDLKWWELR

SEQ ID 66 Protein sequence of M26-IgA1-HC-EGFv3
MESNQPEKNGTATKPENSGNTTSENGQTEPEKKLELRNVSDIELYSQTNGTYRQHVSLDGIP
ENTDTYFVKVKSSAFKDVYIPVASITEEKRNGQSVYKITAKAEKLQQELENKYVDNFTFYLDKK
AKEENTNFTSFSNLVKAINQNPSGTYHLAASLNANEVELGPDERSYIKDTFTGRLIGEKDGKN
YAIYNLKKPLFENLSGATVEKLSLKNVAISGKNDIGSLANEATNGTKIKQVHVDGCVDEEKLYD
DDDKDRWGSSLQCRELLVKNTDLPFIGDISDVKTDIFLRKDINEETEVIYYPDNVSVDQVILSKN
TSEHGQLDLLYPSIDSESEILPGENQVFYDNRTQNVDYLNSYYYLESQKLSDNVEDFTFTRSIE
EALDNSAKVYTYFPTLANKVNAGVQGGLFLMWANDVVEDFTTNILRKDTLDKISDVSAIIPYIG
PALNISNSVRRGNFTEAFAVTGVTILLEAFPEFTIPALGAFVIYSKVQERNEIIKTIDNCLEQRIKR
WKDSYEWMMGTWLSRIITQFNNISYQMYDSLNYQAGAIKAKIDLEYKKYSGSDKENIKSQVE
NLKNSLDVKISEAMNNINKFIRECSVTYLFKNMLPKVIDELNEFDRNTKAKLINLIDSHNIILVGEV
DKLKAKVNNSFQNTIPFNIFSYTNNSLLKDIINEYFNLEGGGGSGGGGSGGGGSALDNSDPKC
PLSHEGYCLNDGVCMYIGTLDRYACNCVVGYVGERCQYRDLKLAELR SEQ ID 67 Protein sequence of M26-IgA1-HC-EGFv11
MESNQPEKNGTATKPENSGNTTSENGQTEPEKKLELRNVSDIELYSQTNGTYRQHVSLDGIP
ENTDTYFVKVKSSAFKDVYIPVASITEEKRNGQSVYKITAKAEKLQQELENKYVDNFTFYLDKK
AKEENTNFTSFSNLVKAINQNPSGTYHLAASLNANEVELGPDERSYIKDTFTGRLIGEKDGKN
YAIYNLKKPLFENLSGATVEKLSLKNVAISGKNDIGSLANEATNGTKIKQVHVDGCVDEEKLYD
DDDKDRWGSSLQCRELLVKNTDLPFIGDISDVKTDIFLRKDINEETEVIYYPDNVSVDQVILSKN
TSEHGQLDLLYPSIDSESEILPGENQVFYDNRTQNVDYLNSYYYLESQKLSDNVEDFTFTRSIE
EALDNSAKVYTYFPTLANKVNAGVQGGLFLMWANDVVEDFTTNILRKDTLDKISDVSAIIPYIG
PALNISNSVRRGNFTEAFAVTGVTILLEAFPEFTIPALGAFVIYSKVQERNEIIKTIDNCLEQRIKR
WKDSYEWMMGTWLSRIITQFNNISYQMYDSLNYQAGAIKAKIDLEYKKYSGSDKENIKSQVE
NLKNSLDVKISEAMNNINKFIRECSVTYLFKNMLPKVIDELNEFDRNTKAKLINLIDSHNIILVGEV
DKLKAKVNNSFQNTIPFNIFSYTNNSLLKDIINEYFNLEGGGGSGGGGSGGGGSALDNSDSEC
PLSHDGYCAHDGVCMYIEALDKYACNCVVGYIGERCQYRDLKWWELR SEQ ID 68 Protein sequence of Tetanus LHN-EGFv3
MPITINNFRYSDPVNNDTIIMMEPPYCKGLDIYYKAFKITDRIWIVPERYEFGTKPEDFNPPSSLI
EGASEYYDPNYLRTDSDKDRFLQTMVKLFNRIKNNVAGEALLDKIINAIPYLGNSYSLLDKFDT
NSNSVSFNLLEQDPSGATTKSAMLTNLIIFGPGPVLNKNEVRGIVLRVDNKNYFPCRDGFGSI
MQMAFCPEYVPTFDNVIENITSLTIGKSKYFQDPALLLMHELIHVLHGLYGMQVSSHEIIPSKQE
IYMQHTYPISAEELFTFGGQDANLISIDIKNDLYEKTLNDYKAIANKLSQVTSCNDPNIDIDSYKQ
IYQQKYQFDKDSNGQYIVNEDKFQILYNSIMYGFTEIELGKKFNIKTRLSYFSMNHDPVKIPNLL
DDTIYNDTEGFNIESKDLKSEYKGQNMRVNTNAFRNVDGSGLVSKLIGLCVDGIITSKTKSDDD
DKNKALNLQCIKIKNEDLTFIAEKNSFSEEPFQDEIVSYNTKNKPLNFNYSLDKIIVDYNLQSKITL
PNDRTTPVTKGIPYAPEYKSNAASTIEIHNIDDNTIYQYLYAQKSPTTLQRITMTNSVDDALINST
KIYSYFPSVISKVNQGAQGILFLQWVRDIIDDFTNESSQKTTIDKISDVSTIVPYIGPALNIVKQG
YEGNFIGALETTGVVLLLEYIPEITLPVIAALSIAESSTQKEKIIKTIDNFLEKRYEKWIEVYKLVKA
KWLGTVNTQFQKRSYQMYRSLEYQVDAIKKIIDYEYKIYSGPDKEQIADEINNLKNKLEEKANK
AMININIFMRESSRSFLVNQMINEAKKQLLEFDTQSKNILMQYIKANSKFIGITELKKLESKINKV
FSTPIPFSYSKNLDCWVDNEEDIDVGLEGGGGSGGGGSGGGGSALDNSDPKCPLSHEGYCL
NDGVCMYIGTLDRYACNCVVGYVGERCQYRDLKLAELR SEQ ID 69 Protein sequence of LHA-CP-EGFv2
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGGGGSGGGGSGGGGSA
DDDDKSRGSKCPPSHDGYCLQGGVCMYIEALDRYACNCVVGYAGERCQYRDLTWWGRRP
LAGGGGSGGGGSGGGGSALVLQCIKVNNWDLFFSPSEDNFTNDLNKGEEITSDTNIEAAEEN
ISLDLIQQYYLTFNFDNEPENISIENLSSDIIGQLELMPNIERFPNGKKYELDKYTMFHYLRAQEF
EHGKSRIALTNSVNEALLNPSRVYTFFSSDYVKKVNKATEAAMFLGWVEQLVYDFTDETSEV
STTDKIADITIIIPYIGPALNIGNMLYKDDFVGALIFSGAVILLEFIPEIAIPVLGTFALVSYIANKVLT
VQTIDNALSKRNEKWDEVYKYIVTNWLAKVNTQIDLIRKKMKEALENQAEATKAIINYQYNQYT
EEEKNNINFNIDDLSSKLNESINKAMININKFLNQCSVSYLMNSMIPYGVKRLEDFDASLKDALL
KYIYDNRGTLIGQVDRLKDKVNNTLSTDIPFQLSKYVDNQRLLSTLEALASG SEQ ID 70 Protein sequence of LHD-EGFv2
MEFVNKQFNYKDPVNGVDIAYIKIPNAGQMQPVKAFKIHNKIWVIPERDTFTNPEEGDLNPPP
EAKQVPVSYYDSTYLSTDNEKDNYLKGVTKLFERIYSTDLGRMLLTSIVRGIPFWGGSTIDTEL
KVIDTNCINVIQPDGSYRSEELNLVIIGPSADIIQFECKSFGHEVLNLTRNGYGSTQYIRFSPDFT
FGFEESLEVDTNPLLGAGKFATDPAVTLAHELIHAGHRLYGIAINPNRVFKVNTNAYYEMSGLE
VSFEELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPKVNYTIY
DGFNLRNTNLAANFNGQNTEINNMNFTKLKNFTGLFEFYKLLCVDGGGGSADDDDKSRGSK
CPPSHDGYCLQGGVCMYIEALDRYACNCVVGYAGERCQYRDLTWWGRRALAGGGGSGGG -continued

| SEQ ID NOS |
|---|
| GSGGGGSALVLQCIKVNNWDLFFSPSEDNFTNDLNKGEEITSDTNIEAAEENISLDLIQQYYLT<br>FNFDNEPENISIENLSSDIIGQLELMPNIERFPNGKKYELDKYTMFHYLRAQEFEHGKSRIALTN<br>SVNEALLNPSRVYTFFSSDYVKKVNKATEAAMFLGWVEQLVYDFTDETSEVSTTDKIADITIIIP<br>YIGPALNIGNMLYKDDFVGALIFSGAVILLEFIPEIAIPVLGTFALVSYIANKVLTVQTIDNALSKRN<br>EKWDEVYKYIVTNWLAKVNTQIDLIRKKMKEALENQAEATKAIINYQYNQYTEEEKNNINFNID<br>DLSSKLNESINKAMININKFLNQCSVSYLMNSMIPYGVKRLEDFDASLKDALLKYIYDNRGTLIG<br>QVDRLKDKVNNTLSTDIPFQLSKYVDNQRLLS |
| SEQ ID 71 Protein sequence of LHC-CP-EGFv2<br>MPITINNFNYSDPVDNKNILYLDTHLNTLANEPEKAFRITGNIWVIPDRFSRNSNPNLNKPPRVT<br>SPKSGYYDPNYLSTDSDKDTFLKEIIKLFKRINSREIGEELIYRLSTDIPFPGNNNTPINTFDFDV<br>DFNSVDVKTRQGNNWVKTGSINPSVIITGPRENIIDPETSTFKLTNNTFAAQEGFGALSIISISP<br>RFMLTYSNATNDVGEGRFSKSEFCMDPILILMHELNHAMHNLYGIAIPNDQTISSVTSNIFYSQ<br>YNVKLEYAEIYAFGGPTIDLIPKSARKYFEEKALDYYRSIAKRLNSITTANPSSFNKYIGEYKQKL<br>IRKYRFVVESSGEVTVNRNKFVELYNELTQIFTEFNYAKIYNVQNRKIYLSNVYTPVTANILDDN<br>VYDIQNGFNIPKSNLNVLFMGQNLSRNPALRKVNPENMLYLFTKFCVDADDDDKSRGSKCPP<br>SHDGYCLQGGVCMYIEALDRYACNCVVGYAGERCQYRDLTWWGRRAALAGGGGSALALQ<br>CRELLVKNTDLPFIGDISDVKTDIFLRKDINEETEVIYYPDNVSVDQVILSKNTSEHGQLDLLYPS<br>IDSESEILPGENQVFYDNRTQNVDYLNSYYYLESQKLSDNVEDFTFTRSIEEALDNSAKVYTYF<br>PTLANKVNAGVQGGLFLMWANDVVEDFTTNILRKDTLDKISDVSAIIPYIGPALNISNSVRRGN<br>FTEAFAVTGVTILLEAFPEFTIPALGAFVIYSKVQERNEIIKTIDNCLEQRIKRWKDSYEWMMGT<br>WLSRIITQFNNISYQMYDSLNYQAGAIKAKIDLEYKKYSGSDKENIKSQVENLKNSLDVKISEAM<br>NNINKFIRECSVTYLFKNMLPKVIDELNEFDRNTKAKLINLIDSHNIILVGEVDKLKAKVNNSFQN<br>TIPFNIFSYTNNSLLKDIINEYF |
| SEQ ID 72 Protein sequence of LHC-EGFv3<br>MPITINNFNYSDPVDNKNILYLDTHLNTLANEPEKAFRITGNIWVIPDRFSRNSNPNLNKPPRVT<br>SPKSGYYDPNYLSTDSDKDTFLKEIIKLFKRINSREIGEELIYRLSTDIPFPGNNNTPINTFDFDV<br>DFNSVDVKTRQGNNWVKTGSINPSVIITGPRENIIDPETSTFKLTNNTFAAQEGFGALSIISISP<br>RFMLTYSNATNDVGEGRFSKSEFCMDPILILMHELNHAMHNLYGIAIPNDQTISSVTSNIFYSQ<br>YNVKLEYAEIYAFGGPTIDLIPKSARKYFEEKALDYYRSIAKRLNSITTANPSSFNKYIGEYKQKL<br>IRKYRFVVESSGEVTVNRNKFVELYNELTQIFTEFNYAKIYNVQNRKIYLSNVYTPVTANILDDN<br>VYDIQNGFNIPKSNLNVLFMGQNLSRNPALRKVNPENMLYLFTKFCVDADDDDKNSDPKCPL<br>SHEGYCLNDGVCMYIGTLDRYACNCVVGYVGERCQYRDLKLAELRAALAGGGGSALALQCR<br>ELLVKNTDLPFIGDISDVKTDIFLRKDINEETEVIYYPDNVSVDQVILSKNTSEHGQLDLLYPSID<br>SESEILPGENQVFYDNRTQNVDYLNSYYYLESQKLSDNVEDFTFTRSIEEALDNSAKVYTYFP<br>TLANKVNAGVQGGLFLMWANDVVEDFTTNILRKDTLDKISDVSAIIPYIGPALNISNSVRRGNFT<br>EAFAVTGVTILLEAFPEFTIPALGAFVIYSKVQERNEIIKTIDNCLEQRIKRWKDSYEWMMGTW<br>LSRIITQFNNISYQMYDSLNYQAGAIKAKIDLEYKKYSGSDKENIKSQVENLKNSLDVKISEAMN<br>NINKFIRECSVTYLFKNMLPKVIDELNEFDRNTKAKLINLIDSHNIILVGEVDKLKAKVNNSFQNTI<br>PFNIFSYTNNSLLKDIINEYF |
| SEQ ID 73 DNA sequence of a EGF variant targeting moiety v3<br>AATAGTGACCCAAAGTGTCCATTAAGCCATGAAGGATATTGTCTAAACGATGGTGTTTGTA<br>TGTACATAGGGACATTGGATAGGTATGCTTGCAATTGCGTAGTGGGATACGTAGGTGAAC<br>GATGCCAATATAGAGACTTAAAACTGGCAGAGCTTAGA |

The invention claimed is:

1. A polypeptide, comprising:

a) a non-cytotoxic protease selected from the group consisting of Clostridial neurotoxin protease and Neisseria IgA protease, wherein the non-cytotoxic protease is capable of cleaving a SNARE, protein;

b) a translocation peptide that is capable of translocating said non-cytotoxic protease from within an endosome of a mammalian cell, across the endosomal membrane thereof and into the cytosol of the mammalian cell, wherein the translocation peptide is selected from the group consisting of: a clostridial neurotoxin translocation domain selected from the group consisting of Botulinum Type A, B, C, D, F, F and G neurotoxin translocation domain and tetanus neurotoxin translocation domain, diphtheria toxin translocation domain, *Pseudomonas* exotoxin type A translocation domain, Anthrax toxin translocation domain, Influenza Virus haemagglutinin translocation domain, Semliki Forest Virus fusogenic protein translocation domain, Semliki Forest Virus E1 protein translocation domain, Vesicular Stomatitis Virus glycoprotein G translocation domain, SER Virus F protein translocation domain, and Foamy Virus envelope glycoprotein translocation domain; and c) an epidermal growth factor (EGF) mutein, wherein said EGF mutein comprises an amino acid sequence having at least 95% sequence identity to the amino acid sequence of SEQ ID NO: 11, and wherein said EGF mutein retains the binding ability of SEQ ID NO: 11 to bind to an EGF receptor.

2. A polypeptide comprising an amino acid sequence having at least 95% sequence identity to an amino acid sequence selected from the group consisting of SEQ ID NOs: 37, 64, 66 and 68;

wherein the amino acid sequence comprises:

a non-cytotoxic protease that is capable of cleaving a snare protein;

a translocation peptide that is capable of translocating the non-cytotoxic protease from within an endosome of a mammalian cell, across the endosomal membrane thereof and into the cytosol of the mammalian cell; and a targeting moiety which is capable of binding to EGF receptor.

3. The polypeptide according to claim 1, wherein the translocation peptide comprises a clostridial neurotoxin translocation domain.

4. The polypeptide according to claim 1, wherein the polypeptide is present as a di-chain polypeptide, wherein the non-cytotoxic protease is linked to the translocation peptide by a disulphide bond.

5. The polypeptide according to claim 1, wherein the polypeptide is an isolated or recombinant polypeptide.

* * * * *

UNITED STATES PATENT AND TRADEMARK OFFICE

CERTIFICATE OF CORRECTION

PATENT NO. : 8,614,069 B2
APPLICATION NO. : 13/059695
DATED : December 24, 2013
INVENTOR(S) : Aimee Cossins et al.

It is certified that error appears in the above-identified patent and that said Letters Patent is hereby corrected as shown below:

In the Claims

Claim 1, Column 217, Line 6, the "," appearing after "SNARE" should be removed.

Claim 1, Column 217, Line 14, the first occurrence of the letter "F" should be changed to "E".

Signed and Sealed this
Twenty-fourth Day of June, 2014

Michelle K. Lee
*Deputy Director of the United States Patent and Trademark Office*

UNITED STATES PATENT AND TRADEMARK OFFICE

CERTIFICATE OF CORRECTION

PATENT NO. : 8,614,069 B2
APPLICATION NO. : 13/059695
DATED : December 24, 2013
INVENTOR(S) : Cossins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this
Twenty-second Day of September, 2015

Michelle K. Lee
*Director of the United States Patent and Trademark Office*